US009512092B2

(12) United States Patent
Cuervo et al.

(10) Patent No.: US 9,512,092 B2
(45) Date of Patent: Dec. 6, 2016

(54) RETINOIC ACID RECEPTOR ANTAGONISTS AS CHAPERONE-MEDIATED AUTOPHAGY MODULATORS AND USES THEREOF

(71) Applicant: ALBERT EINSTEIN COLLEGE OF MEDICINE, INC., Bronx, NY (US)

(72) Inventors: Ana Maria Cuervo, Bronx, NY (US); Evripidis Gavathiotis, Flushing, NY (US); Qisheng Xin, Bronx, NY (US); Bhaskar C. Das, Kansas City, KS (US)

(73) Assignee: ALBERT EINSTEIN COLLEGE OF MEDICINE, INC., Bronx, NY (US)

( * ) Notice: Subject to any disclaimer, the term of this patent is extended or adjusted under 35 U.S.C. 154(b) by 0 days.

(21) Appl. No.: 14/566,762

(22) Filed: Dec. 11, 2014

(65) Prior Publication Data

US 2015/0166492 A1 Jun. 18, 2015

Related U.S. Application Data

(60) Provisional application No. 61/915,063, filed on Dec. 12, 2013.

(51) Int. Cl.
*C07D 265/36* (2006.01)
*C07D 413/10* (2006.01)
*G01N 33/68* (2006.01)
*C07C 279/22* (2006.01)

(52) U.S. Cl.
CPC .......... *C07D 265/36* (2013.01); *C07C 279/22* (2013.01); *C07D 413/10* (2013.01); *C07B 2200/11* (2013.01); *C07C 2101/16* (2013.01); *G01N 2500/04* (2013.01); *G01N 2800/7009* (2013.01)

(58) Field of Classification Search
IPC ..... C07D 265/36,413/10, 279/72; G01N 33/68
See application file for complete search history.

(56) References Cited

U.S. PATENT DOCUMENTS

2007/0149521 A1 6/2007 Crew et al.
2011/0251189 A1 10/2011 Das et al.

FOREIGN PATENT DOCUMENTS

WO 2010068238 A1 6/2010
WO WO 2012139080 A * 10/2012

OTHER PUBLICATIONS

Anguiano et al. (Nature Chemical Biology 9, 374-382 (2013).*
Anguiano, Jaime, et al., "Chemical modulation of chaperone-mediated autophagy by retinoic acid derivatives", Nature Chemical Biology, Published Online: Apr. 14, 2013/ DOI:10.1038/nchembio. 1230, 11 pages, and Supplementary Information, 28 pages.
Anguiano, Jaime, et al., "Chemical modulation of chaperone-mediated autophagy by retinoic acid derivatives", Nature Chemical Biology, Jun. 2013, 9(6): 74-382.
Chioccara, Francesco, et al., "Synthesis of 3-Phenyl-2H-1,4-benzoxazin-2-one, Revision of Some Structural Assignments", J. Heterocyclic Chem. 14:773-775, 1977.
Chioccara, Francesco, et al., "Oxidative Behaviour of 3-Aryl-2H-1,4-Benzoxazines", Tetrahedron 32: 2033-2038, 1976.
Das, Bhaskar C., et al., "Design, Synthesis and Biological Evaluation of 2H-benzo[b][1,4] oxazine derivatives as hypoxia targeted compounds for cancer therapeutics", Bioorganic & Medicinal Chemistry Letters 19:4204-4206, 2009.
Das, Bhaskar C., et al., "Design and Synthesis of Potential New Apoptosis Agents: Hybrid Compounds Containing Perillyl Alcohol and New Constrained Retinoids", Tetrahedron 51(11): 1462-1466, 2010.
Kaushik, Susmita and Cuervo, Ana Maria., "Chaperone-mediated autophagy: a unique way to enter the lysosome world", Trends in Cell Biology, vol. 22, No. 8, 407-417, 2012.
Koga, Hiroshi, et al., "A photoconvertible fluorescent reporter to track chaperone-mediated autophagy", Nature Communications Jul. 12, 2011, 2:386, 1-10.
Kon, Maria et al., "Chaperone-Mediated Autophagy is Required for Tumor Growth", Science Translational Medicine, Nov. 16, 2011, vol. 3, Issue 109, 1-14, and Supplementary Materials 23 pgs.
Sabitha, G. and Rao, A.V. Subba, "Synthesis of 3-Arylcoumarins, 2-Aroylbenzofurans and 3-Aryl-2H-1,4-4-Benzoxazines Under Phase Transfer Catalysis Conditions", Synthetic Communications, 17(3), 341-354, 1987.
Shridhar, D.R., et al., "Synthesis and Anthelmintic Activity of some New Isothiocyanates, Carbamates and N-Furoylthioureas derived from 6-Amino-3-aryl/heteroaryl-2H-1, 4-benzoxazines", J. Indian Chem. Soc., Aug. 1986, vol. LXIII, 761-763.
Shridhar, D.R., et al., "Potential Hypolipidemic Agents: Part IV—Synthesis & Hypolipidemic Activities of Some New Ethyl 3-Aryl-2H-1,4-benzoxazin-7-yloxyalkanoates", Indian Journal of Chemistry, Aug. 1986, vol. 25B, 883-885.
Shridhar, D.R. et al., "A Convenient One-Step Synthesis of 3-Aryl-2H-1,4-benzoxazines", Synthesis, 1981, 11: 912-913.
Xin, Qisheng et al., "Chemical Modulation of Chaperone-Mediated Autophagy for Protection Against Neurodegeneration", poster presented at 8th Annual Drug Discovery for Neurodegeneration Conference, Feb. 2-4, 2014, Miami FL.
Yue, Zhenyu and Yang, X William, "Dangerous duet: LRRK2 and α-synuclein jam at CMA", Nature Neuroscience, Apr. 2013, vol. 16(4): 375-377.
Martin, Laetitia, et al., "Safe and Reliable Synthesis of Diazoketones and Quinoxalines in a Continuous Flow Reactor", Organic Letters, 2011, vol. 13(2): 320-323.
Ali, Iftikhar et, al., "Regioselective Suzuki-Miyaura Cross-Coupling Reactions of 2,6-Dichloroquinoxaline", Synthesis, 2012, 44: 1637-1646.
Li, Leping, et al., "Antitumor Agents 155. Synthesis and Biological Evaluation of 3',6,7-Substituted 2-Phenyl-4-quinolones as Antimicrotubule Agents", J. Med. Chem., 1994, 37: 3400-3407.
Ward, Timothy R., et al., "Synthesis of a Quinolone Library from Ynones", Tetrahedron Letters, 2009, 50: 6494-6497.
Burguete, Asuncion, et al., "Synthesis and Biological Evaluation of New Quinoxaline Derivatives as Antioxidant and Anti-Inflammatory Agents", Chem Biol. Drug Des, 2011, 77: 255-267.

* cited by examiner

*Primary Examiner* — Shirley V Gembeh
(74) *Attorney, Agent, or Firm* — Amster, Rothstein & Ebenstein LLP

(57) ABSTRACT

Compounds, compositions and methods are provided for selectively activating chaperone-mediated autophagy (CMA), protecting cells from oxidative stress, proteotoxicity and lipotoxicity, and/or antagonizing activity of retinoic acid receptor alpha (RARα) in subjects in need thereof.

20 Claims, 21 Drawing Sheets

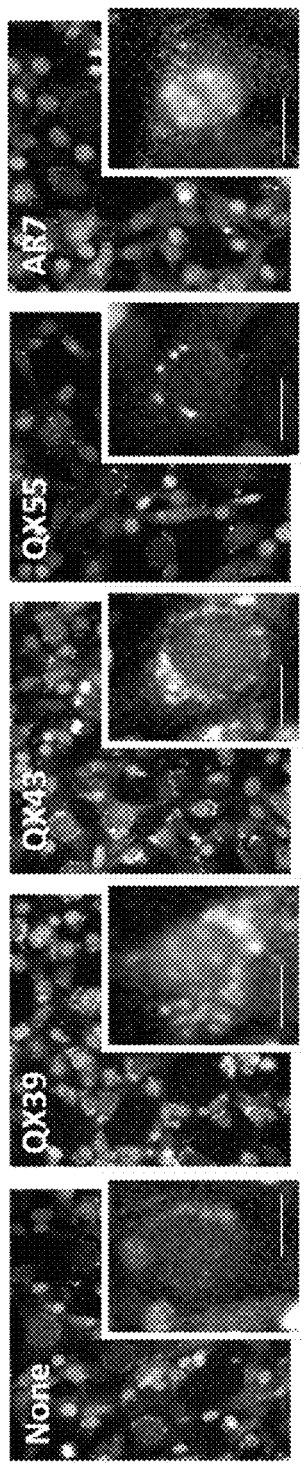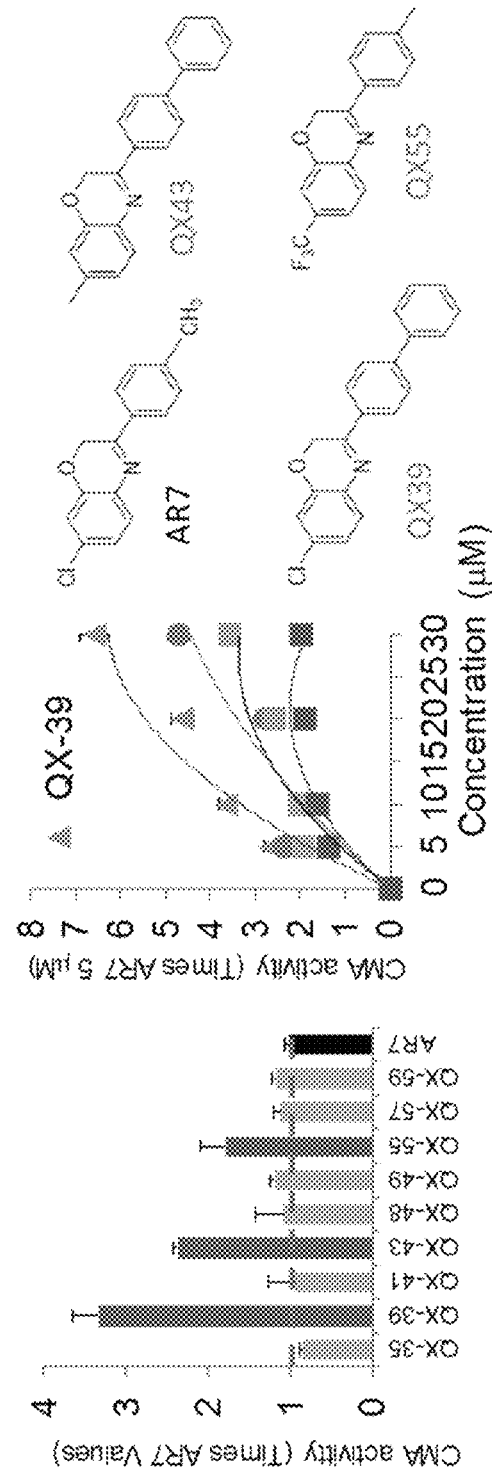
Fig. 9A
Fig. 9B
Fig. 9C
Fig. 9D

RETINOIC ACID RECEPTOR ANTAGONISTS AS CHAPERONE-MEDIATED AUTOPHAGY MODULATORS AND USES THEREOF

CROSS-REFERENCE TO RELATED APPLICATION

This application claims the benefit of U.S. Provisional Patent Application No. 61/915,063, filed Dec. 12, 2013, the contents of which are incorporated herein by reference in their entirety.

STATEMENT OF GOVERNMENT SUPPORT

This invention was made with government support under grant numbers AG021904, AG031782, HL095929 and AA020630 awarded by the National Institutes of Health. The government has certain rights in the invention.

FIELD OF THE INVENTION

The present invention relates to retinoic acid receptor antagonists as chaperone-mediated autophagy (CMA) modulators and uses thereof for treatment of diseases and disorders such as neurodegenerative diseases and diabetes and other diseases that could benefit by protecting cells from oxidative stress, proteotoxicity, and lipotoxicity.

BACKGROUND OF THE INVENTION

Throughout this application various publications are referred to in superscripts. Citations for these references may be found at the end of the specification immediately preceding the claims. The disclosures of these publications are hereby incorporated by reference in their entireties into the subject application to more fully describe the art to which the subject application pertains.

Autophagy is the process by which intracellular components undergo degradation in lysosomes[1,2], contributing in this way to the maintenance of cellular homeostasis and to cellular quality control. In addition, autophagy is upregulated as a mechanism of cellular defense against aggressors or to allow cellular adaptation to changing environmental conditions[3]. Alterations of the autophagic process have been described in multiple pathological conditions and underlie the pathogenesis of severe human diseases such as neurodegeneration, cancer and metabolic disorders[1,4].

The best characterized autophagic pathways are macroautophagy and chaperone-mediated autophagy (CMA)[1]. The distinctive characteristic of CMA is that the specific subset of cytosolic proteins degraded by this pathway are directly translocated across the lysosomal membrane into the lysosomal lumen for degradation[5]. Substrates for this pathway all bear in their amino acid sequence a targeting motif[6] that once recognized by the cytosolic chaperone hsc70, mediates substrate delivery to the surface of lysosomes[7]. Once there, substrates bind to the lysosome-associated membrane protein type 2A (LAMP-2A) and promote its multimerization into a high molecular weight complex, required for substrate translocation[8]. A variant of hsc70 resident in the lysosomal lumen assists substrates to achieve complete translocation inside lysosomes.

CMA is maximally activated in response to stressors such as prolonged nutritional deprivation, oxidative stress, hypoxia or exposure to different toxic compounds[5]. Malfunctioning of CMA has been described in neurodegenerative conditions such as familial forms of Parkinson's disease[9,10] and certain tauopathies[11], in metabolic disorders such as diabetes[12] and in different lysosomal storage disorders[13]. Furthermore, the gradual decline in the activity of this pathway with age has been proposed to act as an aggravating factor in different age-related disorders[14]. In fact, if the reduction in CMA activity with age is prevented in vivo, through genetic manipulation in a mouse model, cellular homeostasis and organ function can be preserved until late in life[15]. These findings, along with the growing number of connections between CMA and human diseases, justify the growing interest in developing efficient chemical modulators of this autophagic pathway.

Chemical compounds shown to have an effect on CMA until now lack selectivity for this pathway[16]. For example, inhibition of protein synthesis or of lysosomal proteases results in reduced CMA degradation, but it also affects many other intracellular processes[16]. Inhibition of glucose-6-phosphate dehydrogenase or of the cytosolic chaperone hsp90 lead to higher CMA activity in some cell types but not in others[16]; and in fact, later studies demonstrated that the effect was not direct but a consequence of compensatory upregulation of other CMA components[8]. One of the limitations for the future development of CMA modulators has been the lack of information on the cellular signaling mechanisms that activate this pathway.

Retinoic acid receptors (RARs) act as transcriptional activators and repressors of a broad subset of genes, contributing thus to modulate cellular processes in which CMA has also been involved, such as differentiation, proliferation and control of cellular homeostasis[17]. Furthermore, RAR loss or aberrant function has been described in many oncogenic processes, where CMA upregulation is a common feature required to sustain cancer cell growth[18]. The three types of RARs identified in mammals, RARα, RARβ and RARγ, are coded by three different genes[17]. In contrast to the complex tissue-dependent expression of RARβ and RARγ, RARα is ubiquitously expressed.

RAR are attractive druggable targets because their natural substrates, all-trans-retinoic acid (ATRA) and similar retinoids have been well characterized[19]. Their efficient trafficking across lipid bilayers, due to their small size and hydrophobic character[20], along with the growing understanding of the chemical modifications that the different regions of retinoid derivatives can undergo intracellularly[21,22] explains why ATRA by-products and derivatives are being already explored for therapeutic purposes.

The present invention address the need for compounds that affect retinoic acid receptor (RAR) signaling and CMA activity and the use of these compounds in treatment of diseases and conditions associated with loss of CMA activity.

SUMMARY OF THE INVENTION

The present invention provides compounds of formula (I):

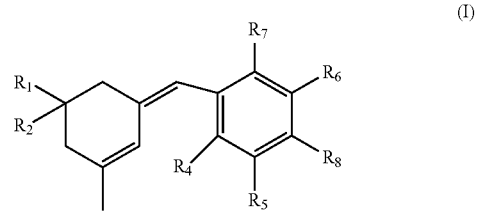

wherein R1-R8 of formula (I) are defined herein below.

The invention also provides methods of selectively activating chaperone-mediated autophagy (CMA) in a subject in need thereof comprising administering to the subject a compound of formula (I), or a compound of formula (II), or a combination of a compound of formula (I) and a compound of formula (II), in an amount effective to activate CMA, wherein formula (II) is

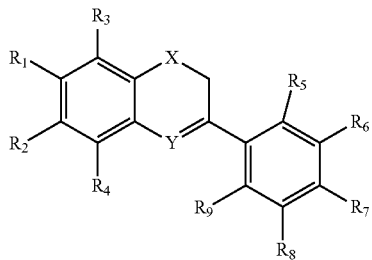

wherein R1-R9, X and Y of formula (II) are defined herein below.

The invention also provides methods of protecting cells from oxidative stress, proteotoxicity and/or lipotoxicity in a subject in need thereof comprising administering to the subject any of the compounds disclosed herein, or a combination of a compound of formula (I) and a compound of formula (II), in an amount effective to protect cells from oxidative stress, proteotoxicity and/or lipotoxicity.

The invention further provides methods of antagonizing activity of retinoic acid receptor alpha (RARα) in a subject in need thereof comprising administering to the subject any of the compounds disclosed herein, or a combination of a compound of formula (I) and a compound of formula (II), in an amount effective to act as a RARα antagonist.

The invention also provides methods of screening for a compound that activates CMA without affecting macroautophagy, the methods comprising identifying a compound that binds to α-helices H12, H3 and H10 of retinoic acid receptor alpha (RARα), wherein a compound that binds to the α-helices H12, H3 and H10 of RARα is a candidate compound for activating CMA without affecting macroautophagy.

The invention further provides methods of screening for a compound that protects cells from oxidative stress, proteotoxicity and/or lipotoxicity, the methods comprising identifying a compound that binds to α-helices H12, H3 and H10 of retinoic acid receptor alpha (RARα), wherein a compound that binds to the α-helices H12, H3 and H10 of RARα is a candidate compound for protecting cells from oxidative stress, proteotoxicity and/or lipotoxicity.

Also provided are pharmaceutical compositions comprising a combination of a compound of formula (I) and a compound of formula (II) and a pharmaceutically acceptable carrier or diluent.

BRIEF DESCRIPTION OF THE DRAWINGS

FIG. 9A-9D. Medicinal chemistry refinement for novel a typical retinoid antagonists (ARA). CMA reporter assay in cells treated with AR7 derivatives (20 mM for 12 h). (A) High content microscopy images. Nuclei are highlighted with DAPI. (B) Quantification of number of puncta per cell relative to AR7 treatment. Compounds with higher CMA activity than AR7 are marked. (C,D) Dose-dependence (C) and structure (D) of three preferred compounds.

DETAILED DESCRIPTION OF THE INVENTION

Figure 1A:
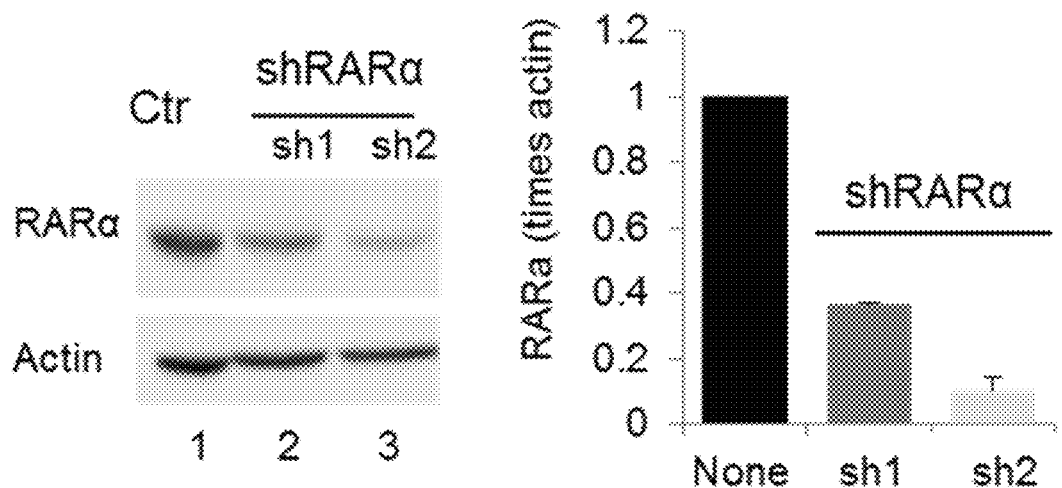
FIG. 1A-1D. Effect of knock-down of RARα on intracellular turnover of long-lived proteins. (a) Knock-down of RARα in NIH3T3 mouse fibroblasts was conducted using two different shRNA (c1 and c2). Ctr: control. Left: Representative immunoblot. Actin is shown as loading control. Right: Levels of RARα in control and knock-down cells determined by densitometric quantification of immunoblots as the one shown on the left. Values are normalized for actin and expressed as times control (none) values. (n=3) (b) Rates of degradation of long-lived proteins in control and RARα knock-down cells maintained in the presence or absence of serum for 12 h. Values are expressed as percentage of proteolysis. (n=3) (c, d) Percentage of lysosomal (c) and macroautophagy (d) degradation in cells assayed as in B, but treated with inhibitors of lysosomal proteolysis (c) or with 3-methyladenine to block macroautophagy (d). Values are expressed as percentage of total protein degradation sensitive to the lysosomal inhibitors (n=3). All values are mean+S.E. and differences with control are significant for * $p<0.05$.

The invention provides a compound having the structure of formula (I)

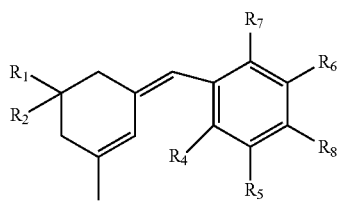

wherein
R1 and R2 of formula (I) are independently H or methyl;
R4, R5, R6 and R7 of formula (I) are independently, H, hydroxyl, halogen or alkyl, or R8 and R5 or R6 of formula (I) together form a 5- or 6-membered heteroaryl; and
R8 of formula (I) is C≡N, 5- or 6-membered heteroaryl,

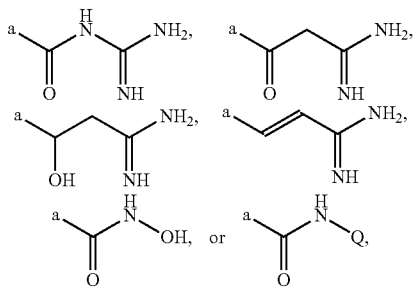

where "a" represents the point of attachment of R8 to the 6-membered ring, and Q is a 5- or 6-membered heteroaryl or Q and C=O of R8 together form a 5- or 6-membered heteroaryl, or R8 and R5 or R6 of formula (I) together form a 5- or 6-membered heteroaryl, where each heteroaryl can be optionally substituted with one or more of CN, =O, $NH_2$ and phenyl; or a pharmaceutically acceptable salt thereof. Preferably, the halogen is Br, Cl, F or I. Preferably, the alkyl is C1-C3 alkyl.

Pharmaceutically acceptable salts that can be used with compounds of the present invention are non-toxic salts derived, for example, from inorganic or organic acids including, but not limited to, salts derived from hydrochloric, sulfuric, phosphoric, acetic, lactic, fumaric, succinic, tartaric, gluconic, citric, methanesulphonic and p-toluenesulphonic acids.

Preferred compounds include those having a structure selected from the group consisting of:

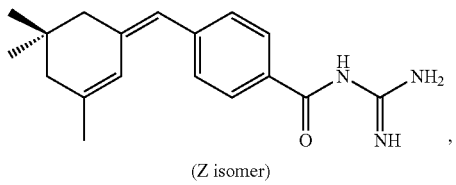
(Z isomer)

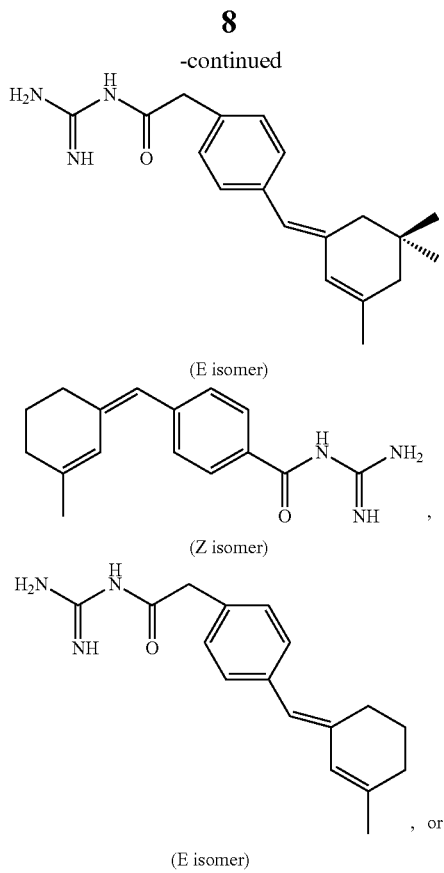
(E isomer)

(Z isomer)

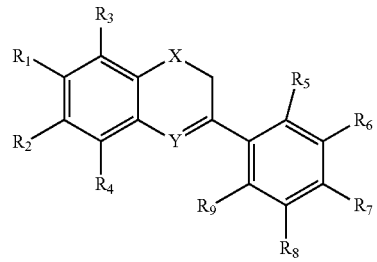
(E isomer)

or a combination thereof, or a pharmaceutically acceptable salt thereof.

Also provided is a pharmaceutical composition comprising any of the compounds disclosed herein, or a combination of any compounds disclosed herein, and a pharmaceutically acceptable carrier or diluent. Examples include a combination of a compound of formula (I) and a compound of formula (II) and a pharmaceutically acceptable carrier or diluent, wherein formula (II) is wherein R1, R2, R3, R4, R5, R6, R8 and R9 of formula (II) are independently H, hydroxyl, halogen, SH, $NO_2$, $CF_3$, COOH, COOR10, CHO, CN, $NH_2$, NHR10, $NHCONH_2$, NHCONHR10, NHCOR10, $NHSO_2R10$, OCR10, COR10, $CH_2R10$, CON(R10,R11), CH=N—OR10, CH=NR10, OR10, SR10, SOR10, $SO_2R10$, COOR10, $CH_2N(R10,R11)$, N(R10,R11), or optionally substituted lower alkyl, alkenyl, alkynyl, cycloalkyl, heterocycloalky, aryl, heteroaryl, aralkyl, or heteroaralkyl; wherein the optional substituent is one or more of F, Cl, Br, I, OH, SH, $NO_2$, COOH, COOR10, R10, CHO, CN, $NH_2$, NHR10, $NHCONH_2$, NHCONHR10, NHCOR10, $NHSO_2R10$, HOCR10, COR10, $CH_2R10$, CON (R10, R11), CH=N—OR10, CH=NR10, OR10, SR10, SOR10, SO₂R10, COOR10, CH₂N(R10, R11), N(R10, R11);

wherein R7 of formula (II) is H, hydroxyl, halogen, CF₃, CN, OCF₃, COOH, COOCH₃, COOR10, COO(CH₂)₂Si (CH₃)₃, COOR10Si(CH₃)₃, NHCOCH₃, C≡C—CH₂OH, C≡C—R10-OH or optionally substituted alkyl, aryl, heteroaryl, aralkyl, heteroaralkyl, cyclic or heterocyclic; wherein the optional substituent is one or more of F, Cl, Br, I, OH, SH, NO₂, CH₃, R10, COOH, COOR10, CHO, CN, NH₂, NHR10, NHCONH₂, NHCONHR10, NHCOR10, NHSO₂R10, HOCR10, COR10, CH₂R10, CON(R10, R11), CH=N—OR10, CH=NR10, OR10, SR10, SOR10, SO₂R10, COOR10, CH₂N(R10, R11), N(R10, R11);

wherein R10 and R11 are independently H or C1-C6 alkyl; wherein X is C, C=O, N, O, S or S=O; and Y is N, NH or C; or a pharmaceutically acceptable salt thereof.

Synthesis of compounds of formula (II) is described below and in U.S. Patent Application Publication No. 2011/0251189, published Oct. 13, 2011, the contents of which is herein incorporated by reference in its entirety.

Pharmaceutically acceptable carriers and diluents that can be used herewith encompasses any of the standard pharmaceutical carriers or diluents, such as, for example, a sterile isotonic saline, phosphate buffered saline solution, water, and emulsions, such as an oil/water or water/oil emulsions.

The invention also provides a method of selectively activating chaperone-mediated autophagy (CMA) in a subject in need thereof comprising administering to the subject any of the compounds disclosed herein, or a compound of formula (II), or a combination of a compound of formula (I) and a compound of formula (II), in an amount effective to activate CMA, wherein formula (II) is

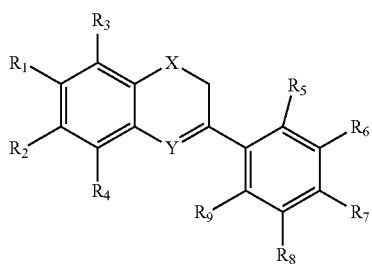

wherein R1, R2, R3, R4, R5, R6, R8 and R9 of formula (II) are independently H, hydroxyl, halogen, SH, NO₂, CF₃, COOH, COOR10, CHO, CN, NH₂, NHR10, NHCONH₂, NHCONHR10, NHCOR10, NHSO₂R10, OCR10, COR10, CH₂R10, CON(R10,R11), CH=N—OR10, CH=NR10, OR10, SR10, SOR10, SO₂R10, COOR10, CH₂N(R10,R11), N(R10,R11), or optionally substituted lower alkyl, alkenyl, alkynyl, cycloalkyl, heterocycloalky, aryl, heteroaryl, aralkyl, or heteroaralkyl; wherein the optional substituent is one or more of F, Cl, Br, I, OH, SH, NO₂, COOH, COOR10, R10, CHO, CN, NH₂, NHR10, NHCONH2, NHCONHR10, NHCOR10, NHSO₂R10, HOCR10, COR10, CH₂R10, CON (R10, R11), CH=N—OR10, CH=NR10, OR10, SR10, SOR10, SO₂R10, COOR10, CH₂N(R10, R11), N(R10, R11);

wherein R7 of formula (II) is H, hydroxyl, halogen, CF₃, CN, OCF₃, COOH, COOCH₃, COOR10, COO(CH₂)₂Si (CH₃)₃, COOR10Si(CH₃)₃, NHCOCH₃, C≡C—CH₂OH, C≡C—R10-OH or optionally substituted alkyl, aryl, heteroaryl, aralkyl, heteroaralkyl, cyclic or heterocyclic; wherein the optional substituent is one or more of F, Cl, Br, I, OH, SH, NO₂, CH₃, R10, COOH, COOR10, CHO, CN, NH₂, NHR10, NHCONH₂, NHCONHR10, NHCOR10, NHSO₂R10, HOCR10, COR10, CH₂R10, CON(R10, R11), CH=N—OR10, CH=NR10, OR10, SR10, SOR10, SO₂R10, COOR10, CH₂N(R10, R11), N(R10, R11);

wherein R10 and R11 are independently H or C1-C6 alkyl; and wherein X is C, C=O, N, O, S or S=O; and Y is N, NH or C; or a pharmaceutically acceptable salt thereof. The subject can have, for example, a neurological disease or disorder, a neurodegenerative disease, a tauopathy, Parkinson's Disease, Alzheimer's Disease, Huntington's Disease, frontotemporal dementia, retinal degeneration, multiple sclerosis, diabetes, a lysosomal storage disorder, a retinal disease, a cardiovascular disease, myocardial infarction, cardiac hypertrophy or a cardiomyopathy. The subject can have reduced CMA compared to a normal subject prior to administering the compound. Preferably, the compound does not affect macroautophagy or other autophagic pathways. In macrophagy, proteins and organelles are sequestered in double-membrane vesicles and delivered to lysosomes for degradation. In CMA, protein substrates are selectively identified and targeted to the lysosome via interactions with a cytosolic chaperone.

The invention also provides a method of protecting cells from oxidative stress, proteotoxicity and/or lipotoxicity in a subject in need thereof comprising administering to the subject any of the compounds disclosed herein, or a combination of a compound of formula (I) and a compound of formula (II), in an amount effective to protect cells from oxidative stress, proteotoxicity and/or lipotoxicity. The subject can have, for example, one or more of the chronic conditions that have been associated with increased oxidative stress and oxidation and a background of propensity to proteotoxicity. The subject can have, for example, one or more of a neurological disease or disorder, a neurodegenerative disease, a tauopathy, Parkinson's Disease, Alzheimer's Disease, Huntington's Disease, frontotemporal dementia, retinal degeneration, multiple sclerosis, diabetes, a lysosomal storage disorder, a cardiovascular disease, myocardial infarction, cardiac hypertrophy and a cardiomyopathy. The cells being protected can comprise, for example, cardiac cells, liver cells, neurons, myocytes, fibroblasts and/or immune cells. The compound can, for example, selectively activate chaperone-mediated autophagy (CMA). In one embodiment, the compound does not affect macroautophagy. The compound can, for example, antagonize activity of retinoic acid receptor alpha (RARα).

The invention also provides a method of antagonizing activity of retinoic acid receptor alpha (RARα) in a subject in need thereof comprising administering to the subject any of the compounds disclosed herein, or a combination of a compound of formula (I) and a compound of formula (II), in an amount effective to act as a RARα antagonist.

Preferred embodiments include those where the compound of formula (II) has the formula

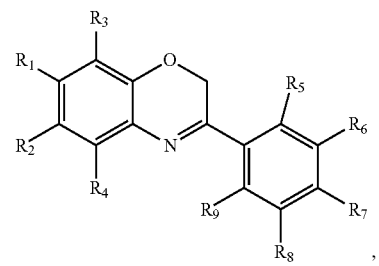

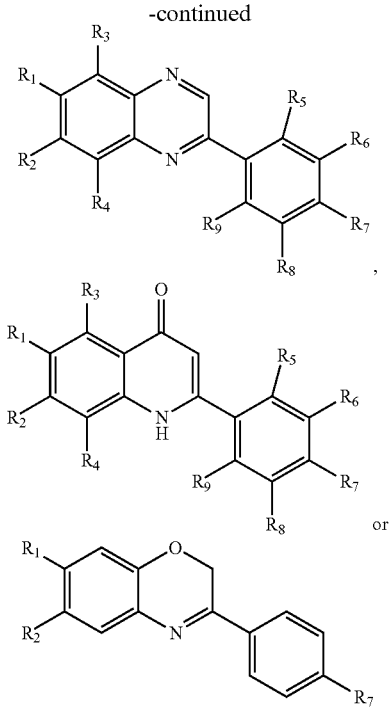

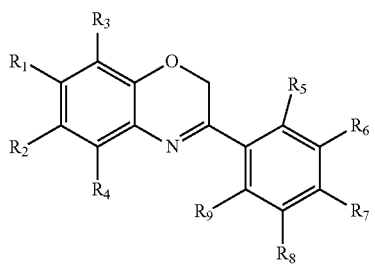

or a pharmaceutically acceptable salt thereof.

Also provided is a compound having the structure wherein
R1, R2, R3, R4, R5, R6, R8 and R9 are independently H, hydroxyl, halogen, CF$_3$, COOH, or COOCH$_3$, SH, NO$_2$, COOR10, CHO, CN, NH$_2$, NHR10, NHCONH$_2$, NHCONHR10, NHCOR10, NHSO$_2$R10, OCR10, COR10, CH$_2$R10, CON(R10,R11), CH=N—OR10, CH=NR10, OR10, SR10, SOR10, SO$_2$R10, COOR10, CH$_2$N(R10,R11), N(R10,R11), or optionally substituted lower alkyl, alkenyl, alkynyl, cycloalkyl, heterocycloalky, aryl, heteroaryl, aralkyl, or heteroaralkyl; wherein the optional substituent is one or more of F, Cl, Br, I, OH, SH, NO$_2$, COOH, COOR10, R10, CHO, CN, NH$_2$, NHR10, NHCONH$_2$, NHCONHR10, NHCOR10, NHSO$_2$R10, HOCR10, COR10, CH$_2$R10, CON (R10, R11), CH=N—OR10, CH=NR10, OR10, SR10, SOR10, SO$_2$R10, COOR10, CH$_2$N(R10, R11), N(R10, R11);
R7 is CF$_3$, CN, OCF$_3$, COOH, COOCH$_3$, COOR10, COO(CH$_2$)$_2$Si(CH$_3$)$_3$, COOR10Si(CH$_3$)$_3$, NHCOCH$_3$, C≡C—CH$_2$OH, C≡C—R10-OH or optionally substituted aryl, heteroaryl, aralkyl, heteroaralkyl, cyclic or heterocyclic; wherein the optional substituent is one or more of F, Cl, Br, I, OH, SH, NO$_2$, CH$_3$, R10, COOH, COOR10, CHO, CN, NH$_2$, NHR10, NHCONH$_2$, NHCONHR10, NHCOR10, NHSO$_2$R10, HOCR10, COR10, CH$_2$R10, CON(R10, R11), CH=N—OR10, CH=NR10, OR10, SR10, SOR10, SO$_2$R10, COOR10, CH$_2$N(R10, R11), N(R10, R11); and
R10 and R11 are independently H or C1-C6 alkyl; or a pharmaceutically acceptable salt thereof.

In any of the methods or compounds or compositions disclosed herein, any one or more halogen can be Br, Cl, F or I independently of any other halogen. In any of the methods or compounds disclosed herein, any one or more alkyl can be, e.g., C1-C6 alkyl or C1-C3 alkyl independently of any other alkyl. In any of the methods or compounds disclosed herein, any one or more aralkyl can contain C1-C3 alkyl independently of any other aralkyl. An alkyl can be, for example, methyl, ethyl, propyl, butyl, pentyl, or hexyl, independently of any other alkyl.

In any of the methods or compounds or compositions disclosed herein, the optionally substituted aryl or heteroaryl can be

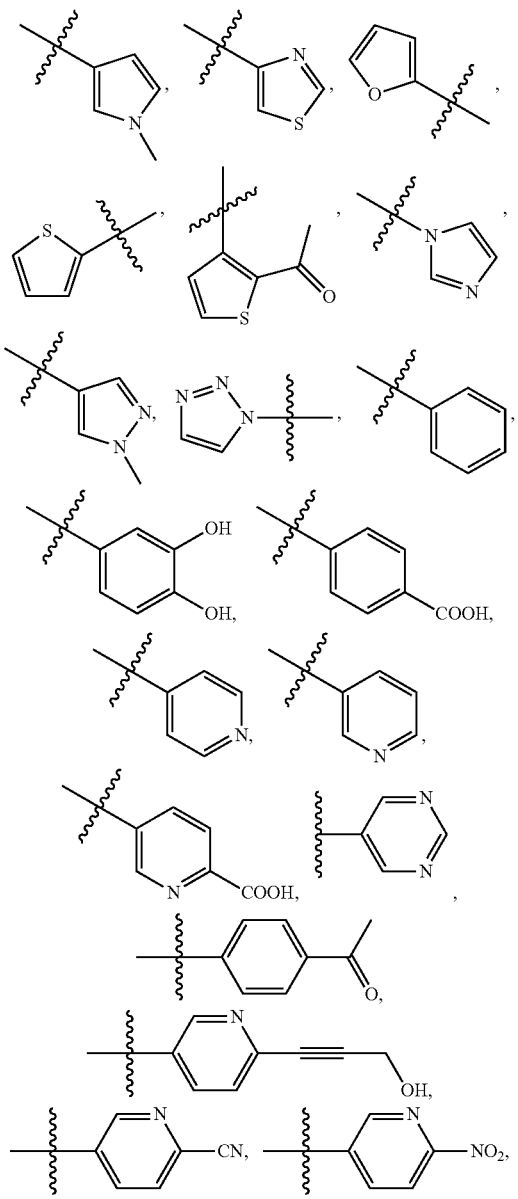

where the wavy line indicates the point of the optionally substituted aryl or heteroaryl to the main structure.

Preferred compounds include the following compounds:

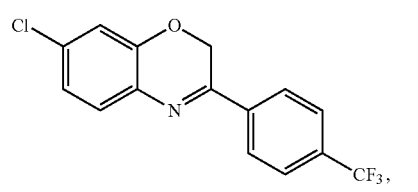
QX-61
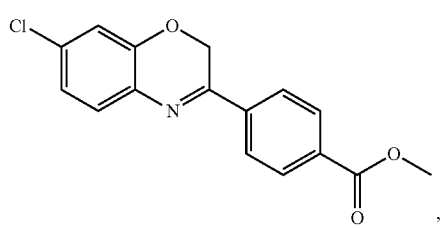
QX-67
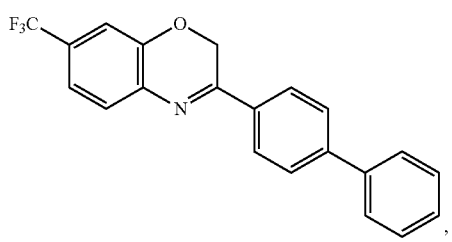
QX-69
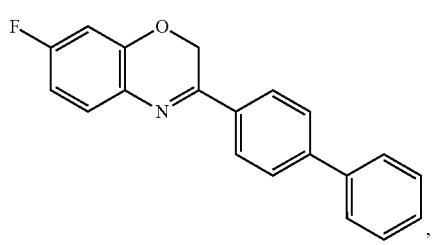
QX-70
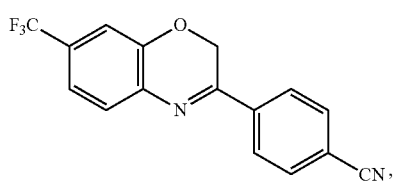
QX-71
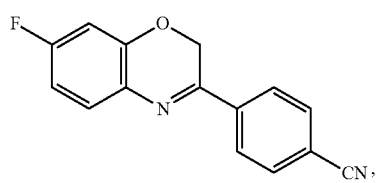
QX-73
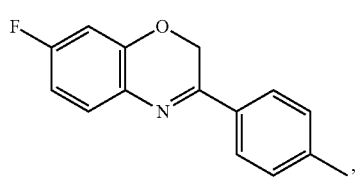
QX-75
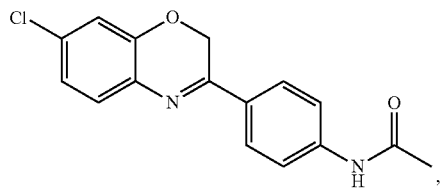
QX-77
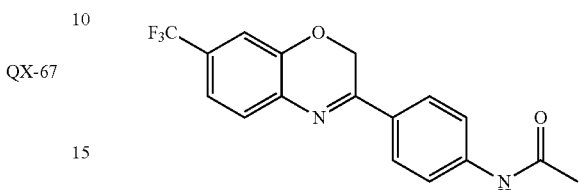
QX-79
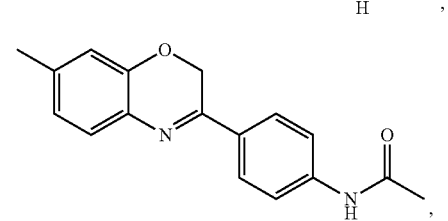
QX-51
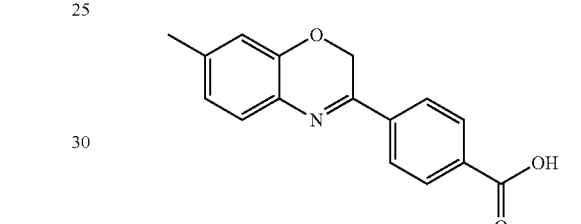
QX-81
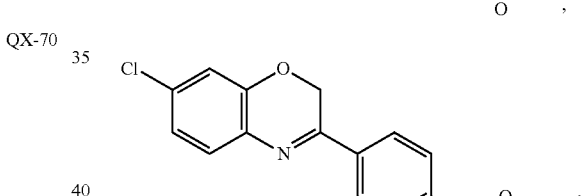
QX-89
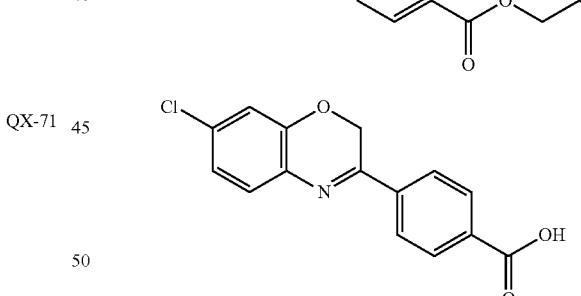
QX-90
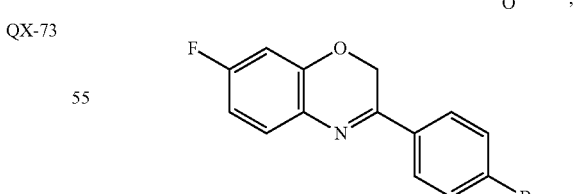
QX-94
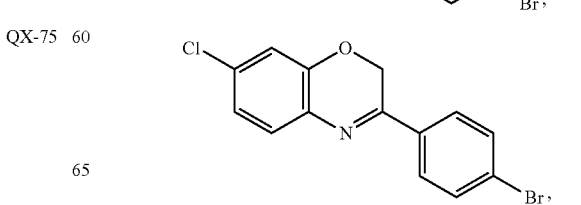
QX-95

QX-98
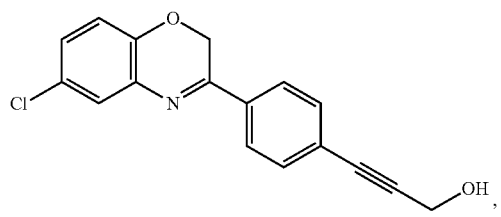

QX-115
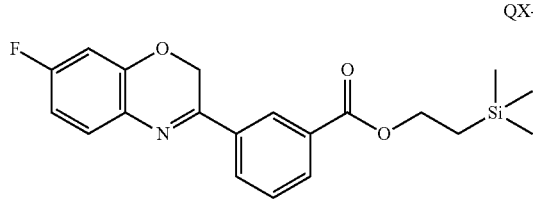

QX-119
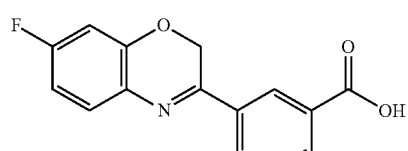

QX-107
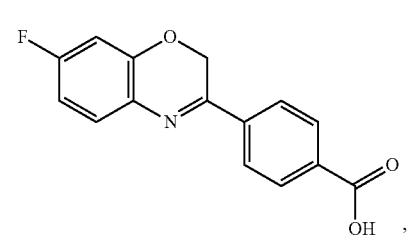

QX-112
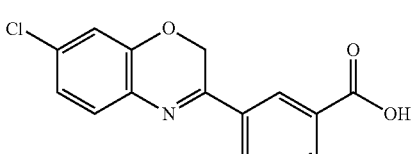

QX-129
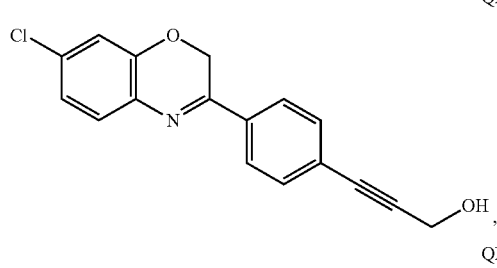

QX-134
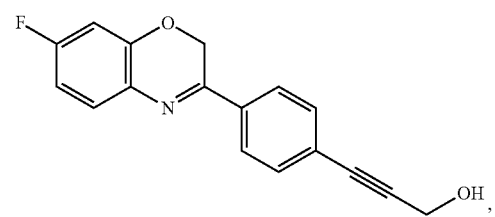

QX-136
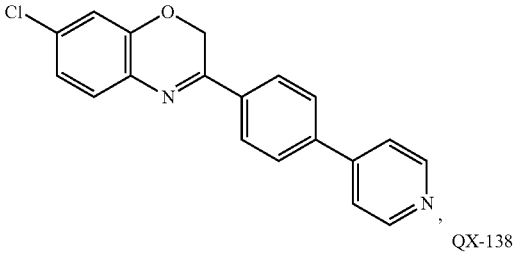

QX-138
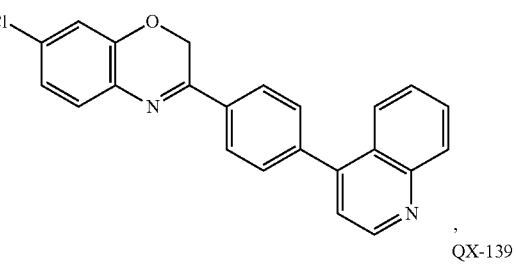

QX-139
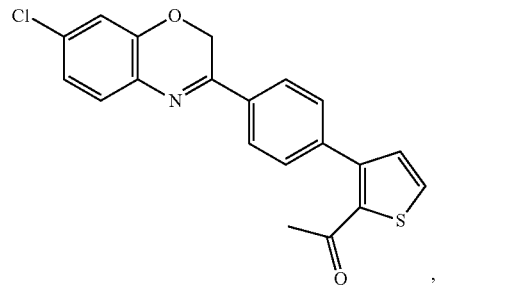

QX-2-52
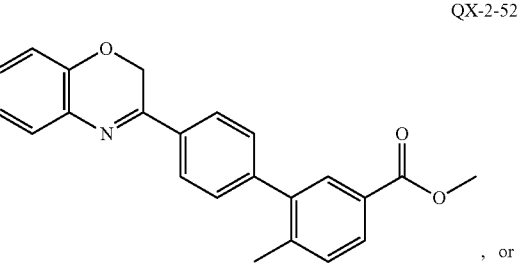

QX-2-85
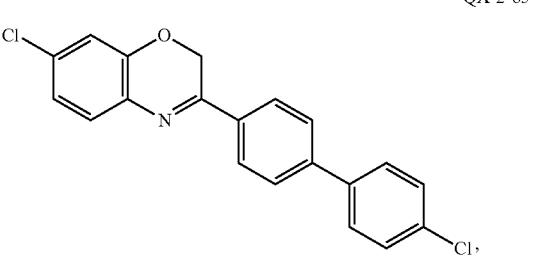

or a combination thereof, or a pharmaceutically acceptable salt thereof.

The invention also provides a method of screening for a compound that activates CMA without affecting macroautophagy, the method comprising identifying a compound that binds to α-helices H12, H3 and H10 of retinoic acid receptor alpha (RARα), wherein a compound that binds to the α-helices H12, H3 and H10 of RARα is a candidate compound for activating CMA without affecting macroautophagy. A photoconvertible fluorescent reporter assay to track CMA has been described.[30]

The invention further provides a method of screening for a compound that protects cells from oxidative stress, proteotoxicity and/or lipotoxicity, the method comprising identifying a compound that binds to α-helices H12, H3 and H10 of retinoic acid receptor alpha (RARα), wherein a compound that binds to the α-helices H12, H3 and H10 of RARα is a candidate compound for protecting cells from oxidative stress, proteotoxicity and/or lipotoxicity. The compound can protect cells from oxidative stress, proteotoxicity and/or lipotoxicity through activation of CMA.

H3, H10 and H12 of human RARα have the following amino acid sequences: H3: DIDLWDKFSELSTKCIIKT-VEFAK (SEQ ID NO:1), H10: DLRSISAKGAERVITLK-MEIP (SEQ ID NO:2) and H12: GSMPPLIQEMLEN (SEQ ID NO:3).

In either of the above two screening methods, the compound can be, e.g., a retinoic acid receptor α (RARα) antagonist.

The compounds and compositions of the present invention can be administered to subjects using routes of administration known in the art. The administration can be systemic or localized to a specific site. Routes of administration include, but are not limited to, intravenous, intramuscular, intrathecal or subcutaneous injection, oral or rectal administration, and injection into a specific site.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example A

Overview

The effect of retinoic acid receptor (RAR) signaling on CMA activity was investigated by taking advantage of expertise in the design and synthesis of novel retinoid derivatives with different biological activities[23,24] to generate novel RARα modulators that could be used to modify CMA activity. Structure-based chemical design was used to mimic the critical regions of all-trans-retinoic acid (ATRA), and modifications were introduced that allow these novel retinoids to selectively modulate different RARα downstream effects. These compounds were demonstrated to lead to selective activation of CMA without noticeable changes in other autophagic pathways. Furthermore, it was demonstrated that chemical enhancement of CMA by treatment of cells with these novel compounds renders cells more resistant to oxidative stress and proteotoxicity. These findings highlight the therapeutic applicability of these and related compounds in the treatment of chronic diseases that associate with loss of CMA activity.

Methods

Animals, Cells and Reagents.

Adult male Wistar rats (Charles River Laboratories) fasted for 48 h before sacrifice were used for isolation of lysosomes from liver. All animal work was approved and performed according to the guidelines set by the Albert Einstein College of Medicine Institutional Animal Care and Use Committee. Mouse fibroblasts (NIH3T3) from the American Type Culture Collection were cultured in Dulbecco's Modified Eagle's Medium (Sigma) in the presence of 10% newborn calf serum. Serum removal was performed by thoroughly washing the cells with Hanks' Balanced Salt Solution (Invitrogen) and placing them in serum-free complete medium. Where indicated, cells were treated with the macroautophagy inhibitor 3-methyladenine (Sigma) at a final concentration of 10 mM or with 20 mM $NH_4Cl$ and 100 μM leupeptin (Fisher BioReagents) to inhibit lysosomal proteolysis. Where indicated, paraquat was added directly to the culture media to induce oxidative stress. Stable knockdown of LAMP-2A, LAMP-2B or RARα was obtained using vector-mediated stable RNA interference (RNAi) directed specifically against the LAMP-2A or LAMP-2B exon as described previously[33] or against the two following regions of human RARα: GAAAGTCTACGTCCGGAAA (SEQ ID NO:4) and GCAGCAGTTCCGAAGAGAT (SEQ ID NO:5). The plasmid encoding for mCherry-GFP-LC3 was from Addgene and for α-synuclein was a generous gift from Dr. Esther Wong (Nanyang Technological University, Singapore). Sources of chemicals and antibodies were as described previously[8,9,30,35]. ATRA was purchased from Sigma, BMS614 and AM580 were from Tocris Bioscience and the antibody against RARα was from Cell Signaling.

Autophagic Measurements.

Intracellular protein degradation was measured by metabolic labeling and pulse chase experiments as described before[39]. Autophagic flux was measured as changes in levels of LC3-II upon inhibition of lysosomal proteolysis[29] and as the ratio mcherry-positive puncta to double labelled (mCherry-GFP) puncta in cells transfected with the mCherry-GFP-LC3 reporter[40]. CMA activity was determined using the photoactivable KFERQ-PA-mCherry1 reporter that allows visualization of CMA activation as an increase in the number of fluorescent puncta per cell[30]. Analysis of CMA in isolated lysosomes was performed using a previously developed in vitro assay to measure the ability of intact lysosomes to take up and degrade well-characterized CMA substrate proteins[39]. Lysosomes active for CMA were isolated from rat liver using differential centrifugation and floatation in discontinuous density metrizamide gradients following a previously optimized procedure[41]. Lysosomes from cultured cells were isolated by similar procedures but using instead discontinuous metrizamide/percoll gradients after rupture of the plasma membrane through nitrogen cavitation[33].

Design and Synthesis of Novel-Retinoid Derivatives. Preparation of Guanidine Retinoids (GR1) and (GR2) (FIG. 4b and Table 1):

Solid sodium chloride obtained from reacting guanidine hydrochloride in DMF:dioxane and sodium tert-butoxide under nitrogen (g) at 50-55° C. for 30 min was filtered and the filtrate was added to a solution of retinoid and CDI in DMF. The progress of the reaction was monitored by TLC, the solid product was collected by filtration and washed to remove excess guanidine.

Preparation of A typical Retinoid AR7 (FIG. 4b and Table 1):

The 2H-benzo[b][1,4]oxazines were synthesized by modifying the existing methods[42]. 2-bromo-4-chloroacetophenone (0.01 mol) in dichloromethane was added dropwise to a solution of 2-aminophenol in dichloromethane, aqueous potassium carbonate (20% w/v) and tetrabutylammonium hydrogen sulphate. The resultant mixture was refluxed till completion for 4-6 h and the organic layer was extracted with dichloromethane and dried over sodium sulphate evaporated in vacuum to give a crude solid product. The solid was then recrystallized with hot ethanol to obtain pure yield 87-95%. In the NOE analysis, E/Z isomers of GR1 were assigned based on a pair of weak vinyl peaks at 6.4 ppm and 6.12 ppm (Z-isomer) and another pair of strong vinyl peaks at 6.27 ppm and 5.98 ppm (E-isomer). For GR2, E/Z isomers were assigned based on a pair of weak vinyl peaks at 6.43 ppm and 6.12 ppm (Z-isomer) and another pair of strong vinyl peaks at 6.19 ppm and 6.00 ppm (E-isomer).

In Silico Docking.

AR7, GR1 and GR2 structures were drawn in ChemDraw Ultra 12.0 and converted to three-dimensional all-atom structures from sdf format using LigPrep (Version 2.5, Schrödinger, LLC, New York, N.Y., 2011). For each ligand a maximum of 4 stereoisomers were generated, ionization states and tautomers were generated for pH 7 and pH 2 and geometries optimized and energy minimized before for docking. The structure of the RARα-RXR hetero-dimer in complex with the small molecule antagonist BM614 (PDB ID: 1DKF), was used for docking and molecular dynamics. The RARα-RXR structure was prepared using MAESTRO protein preparations module (Version 9.2, Schrödinger, LLC, New York, N.Y., 2011). The structure of the antagonist was removed from the RARα site, water molecules at a distance of more than 5 Å from heteroatoms were removed, all missing protons were generated, hydrogens were optimized for best hydrogen bonding network bonds and formal charges were assigned and structure was gently minimized by restrained energy minimization. The ligand-binding pocket was defined within 5 Å of the BMS614 pose and receptor grid size and center was generated based on the position and the size of the BMS614. To account for receptor flexibility in docking, scaling of van der Waals' radii of non polar atoms with the absolute value of the partial atomic charge less than or equal to 0.25 for protein atoms was set to 1 and for ligand non polar atoms with partial atomic charges less than or equal to 0.15 was set to 0.8. Docking was performed in ligand flexible mode using Glide[43-45] (Version 5.8, Schrödinger) using the extra precision (XP) mode. All three molecules were docked into the BMS614 binding site with and without rotatable binding site hydroxyl-groups. Structures were analyzed using MAESTRO and PyMOL (The PyMOL Molecular Graphics System, Version 1.5.0.4 Schrödinger, LLC.)

Molecular Dynamics Simulations.

The lowest-energy docked structures for each ligand were minimized using the Desmond molecular dynamics system[46-48] (Version 3.0, D. E. Shaw Research, New York, N.Y., 2011. Maestro-Desmond Interoperability Tools, version 3.1, Schrödinger, New York, N.Y., 2012). All minimization and simulation systems were set up using MAESTRO tools. The minimization protocol was performed using an OPLS-2005 force field with a cubic-TIP3P water-box, 150 mM NaCl and water-box boundaries set to a minimum of 10 Å from the proteins surface in all directions. Minimization was performed with a maximum of 2000 iterations with a convergence threshold of 1 kcal/mol/Å, a steepest descent method was used initially until a gradient threshold of 25 kcal/mol/Å is reached. Simulated annealing and molecular dynamics in explicit water were performed on the refined lowest energy docked structures, using the Desmond molecular dynamics system and OPLS-2005 force field. A five stage simulated annealing protocol was performed with 40 ps intervals where the temperature was linearly interpolated between each time point with temperature steps of 10, 100, 300, 400, and 300 K. An NVT ensemble class was employed with a Berendsen thermostat with a relaxation time of 1 ps. A 6 ns molecular dynamics simulation was performed with and without simulated annealing for each of the minimized lowest-energy docking posses. Molecular dynamics simulations were performed using an NPT ensemble class at 300 K and 1.01325 bar. A Nose-Hoover chain thermostat method with a 1 ps relaxation time and a Martyna-Tobias-Klein Barostat Method with a 2 ps relaxation time were used. All docking and molecular dynamic simulations were analyzed using tools within MAESTRO and figures were prepared using PyMOL.

Measurement of RARα and RXR Activity.

A RAR-responsive luciferase construct was utilized to monitor the activity of RARα in cultured cells. Cells were co-transfected with pCMX-Gal-L-hRARα and a construct encoding the firefly luciferase reporter gene under the control of a minimal promoter and tandem repeats of the retinoic-acid response element (tk-px3-luc). Co-transfection with a renilla luciferase reporter plasmid was performed to control for efficiency of transfection. RXR activity was measured by similar procedures using co-transfection with pCMX-mRXR and tk-apoA1-luc. Compounds were added 24 h after transfection and 48 h later cells were lysed and assayed for luciferase activity using the Dual-Luciferase Reporter Assay System (Progmega). Luciferase values were normalized to the renilla luciferase reporter.

Intracellular Protein Degradation.

Confluent cells labelled with [$^3$H]leucine (2 Ci/ml) (NEN-PerkinElmer Life Sciences) for 48 h were extensively washed and maintained in medium with an excess of unlabeled leucine[49]. Aliquots of the medium taken at different times were precipitated in trichloroacetic acid and proteolysis measured as the amount of acid-precipitable radioactivity transformed in acid-soluble radioactivity at each time. The amount of lysosomal proteolysis was calculated by treating parallel wells with 20 mM $NH_4Cl$ and 100 µM leupeptin during the chase period.

CMA Reporter Assay.

The photoactivable CMA reporter was constructed by inserting a sequence of 21 amino acids of Ribonuclease A bearing the CMA-targeting motif in the N-terminus multicloning site of the photoactivable protein mCherry1 (PA-mCherry1)[30]. Cells transduced with a lentivirus carrying the KFERQ-bearing constructs were photoactivated by exposure to a 3.5 mA (current constant) light emitting diode (LED: Norlux, 405 nm) for 10 min and at the desired times fixed in 3% formaldehyde and images were captured with an Axiovert 200 fluorescence microscope (Zeiss) with apotome and equipped with a 63× 1.4 NA oil objective lens and red (ex. 570/30 nm, em. 615/30 nm), cyan (ex. 365/50 nm and em. 530/45 nm) and green (ex. 475/40 nm and em. 535/45 nm) filter sets (Chroma). All images were acquired with a high-resolution CCD camera after optical sectioning through the apotome. Images were prepared using Adobe Photoshop 6.0 software (Adobe Systems). Quantification was performed in individual frames after deconvolution and thresholding using ImageJ software (NIH) in a minimum of 50 cells.

Lysosomal In Vitro Uptake Assay.

Transport of purified proteins into isolated lysosomes was analyzed using a previously described in vitro system[41]. Briefly, intact lysosomes treated or not with a pool of protease inhibitors for 10 min on ice, were incubated with glyceraldhyeyde-3-phosphate dehydrogenase (GAPDH) for 20 min at 37° C. At the end of the incubation, lysosomes were recovered by centrifugation, washed, and subjected to SDS-PAGE and immunoblot for GAPDH. Binding was calculated after densitometric analysis as the amount of GAPDH recovered in the lysosomes not treated with protease inhibitors, and uptake as the difference in the amount of GAPDH recovered in treated minus untreated lysosomes.

Lentivirus-Mediated shRNA.

Lentiviral particles were generated by co-transfection with the lentiviral transfer vector carrying the hairpin sequence against the desired mRNA and the third-generation packaging constructs pMDLg/pRRE and pRSV-REV, and as envelope the G glycoprotein of the VSV (pMD2.G) into HEK293T cells as described before[33]. Cultured cells were transduced by addition of packed virus at a titter of $2.63 \times 10^6$ units/ml.

General Procedure for Preparation of Guanidine Retinoids (GR1 and GR2)[23] (FIG. 4b and Table 1):

A solution of guanidine hydrochloride (2 mmol) in DMF:dioxane (1:1; 5 ml) was added sodium tert-butoxide (2 mmol) and the reaction mixture was heated under nitrogen at 50-55° C. for 30 min. The mixture was cooled to room temperature, the solid sodium chloride was filtered and the filtrate was added to the 1 h stirred solution of retinoid and CDI in DMF at room temperature. The progress of the reaction was monitored by TLC. After completion of the reaction, water (10 ml) was added, the solid product was collected by filtration and the solid was washed with cold water to remove excess guanidine.

Compound GR1: N-[4-(3,5,5-trimethyl-cyclohex-2-enylidenemethyl)-benzoyl]-guanidine. 1H NMR (300 MHz, CDCl3): d 0.88 (s, 6H), 1.78 (s, 3H), 1.91 (s, 2H), 2.33 (s, 2H), 2.48-2.53 (m, 4H), 2.74 (s, 1H), 2.90 (s, 1H), 3.52 (s, 1H), 6.01 (s, 1H), 6.32 (s, 1H), 7.24-7.28 (d, J=12 Hz, 2H), 8.01-8.05 (d, J=12 Hz, 2H); 13C NMR (75 MHz, CDCl3): d 25.0, 29.1, 31.2, 45.1, 126.0, 127.3, 128.8, 129.5, 137.6, 137.9, 138.0, 140.6, 163.2, 176.5; HR-MS: (C18H24N3O) calcd ([M+H]+) 298.1921. found 298.1928.

Compound GR2: N-[4-(3-methyl-cyclohex-2-enylidenemethyl)-benzoyl]-guanidine. 1H NMR (300 MHz, CDCl3): d 1.57-1.1.70 (m, 2H), 1.80 (s, 3H), 2.03-2.13 (m, 2H), 2.48-2.60 (m, 6H), 6.01 (s, 1H), 6.20 (s, 1H), 7.23-7.27 (d, J=12 Hz, 2H), 7.98-7.02 (d, J=12 Hz, 2H); 13C NMR (75 MHz, CDCl3): d 23.2, 24.7, 26.8, 30.7, 124.5, 127.9, 128.8, 129.3, 137.4, 139.3, 140.2, 140.7, 142.7, 163.8, 176.4; HR-MS: (C17H20N3O) calcd ([M+H]+) 270.1606. found 270.1614.

General Procedure for the Preparation of A typical Retinoids (AR1-AR10)[50] (FIG. 4b and Table 1):

The 2H-benzo[b][1,4]oxazines were synthesized by modifying the existing methods. To a solution of 2-aminophenol (0.001 mol) in dichloromethane (40 ml) aqueous potassium carbonate (20% w/v) and tetrabutylammonium hydrogen sulfate (0.0005 mol) was added and mixture was stirred for 2 h at room temperature. After 2 h, 2-bromo-4-chloroacetophenone (0.01 mol) in 20 ml dichloromethane was added drop-wise through a course of 15 min and the resultant mixture was refluxed till completion for 4-6 h. The organic layer was extracted with dichloromethane and dried over sodium sulfate evaporated in vacuum to give crude solid product. The solid was then recrystallized with hot ethanol to get pure yield 87-95%.

General Procedure for the Preparation of α-Aminonitrile Functionalized Novel Constrained Retinoids (αAmR1-αAmR11)[32] (Table 1):

Into a 10-mL round-bottomed flask were added β-cyclocitral (1.0 mmol), amine (1.0 mmol), TMSCN (1.2 mmol), H₂O (2 mL), and InCl₃ (0.1 mmol) sequentially. The reaction mixture was stirred vigorously at room temperature and the progress of the reaction was monitored by TLC. After stirring for 4-6 h at room temperature the solid that was obtained was filtered and washed with water and hexane to yield the desired product retinoids (αAmR1-αAmR11).

General Procedure for the Preparation of Boron-α-Aminonitrile Functionalized Novel Constrained Retinoids (BAmR1-BamR6) (Table 1):

Into a 10-mL round-bottomed flask were added aldehyde (1.0 mmol), amine (1.0 mmol), TMSCN (1.2 mmol), H₂O (2 mL), and InCl₃ (0.1 mmol) sequentially. The reaction mixture was stirred vigorously at room temperature and the progress of the reaction was monitored by TLC. After stirring for 4-6 h at room temperature the solid that was obtained was filtered and washed with water and hexane to yield the desired product retinoids (BAmR1-BamR6).

General Methods.

Protein concentration was measured by the Lowry method using bovine serum albumin as a standard. Cell viability was determined using the CellTiterBlue® Kit (Promega). Carbonyl groups were detected with the OxyBlot Oxidized Protein Detection Kit (Chemicon International). Apoptosis was determined with Annexin V-PE apoptosis detection kit (BD Pharmingen). After SDS-PAGE and immunoblotting, the proteins recognized by the specific antibodies were visualized by chemiluminescence methods (Western Lightning; PerkinElmer) using peroxidase-conjugated secondary antibodies. Densitometric quantification of the immunoblotted membranes was performed using Image J (NIH). Quantitative real time PCR was used to determine changes in mRNA levels using the TaqMan One-Step RT-PCR Master Mix reagent (Applied Biosystem). Fluorescence was performed using conventional procedures and all images were captured with an Axiovert 200 fluorescence microscope (Zeiss) with apotome.

Statistical Analysis.

All numerical results are reported as mean±s.e.m. and represent data from a minimum of three independent experiments unless otherwise stated. Statistical significance of difference between groups was determined in instances of single comparisons by the two-tailed unpaired Student's t-test of the means. In instances of multiple means comparisons, we used one-way analysis of variance (ANOVA) followed by the Bonferroni post hoc test to determine statistical significance. Statistic analysis was performed in all of the assays, and significant differences are noted in the graphical representations.

Results

RAR Signaling has Opposite Effects in Different Autophagic Pathways.

Recent studies have described that retinoic acid exerts a cell-type dependent stimulatory effect on macroautophagy via Beclin-1 upregulation and inhibition of the mTOR pathway[25-27] or by enhancing autophagosome maturation[28]. The effects of these interventions on CMA have not been explored until now. To directly analyze the effect of RAR signaling on different autophagic pathways, RARα was knocked down in mouse fibroblasts, the most abundant type of RAR in these cells. Lentiviral transduction with two different shRNA against RARα resulted in 75-90% stable knock-down of this receptor (FIG. 1a).

Figure 1B:
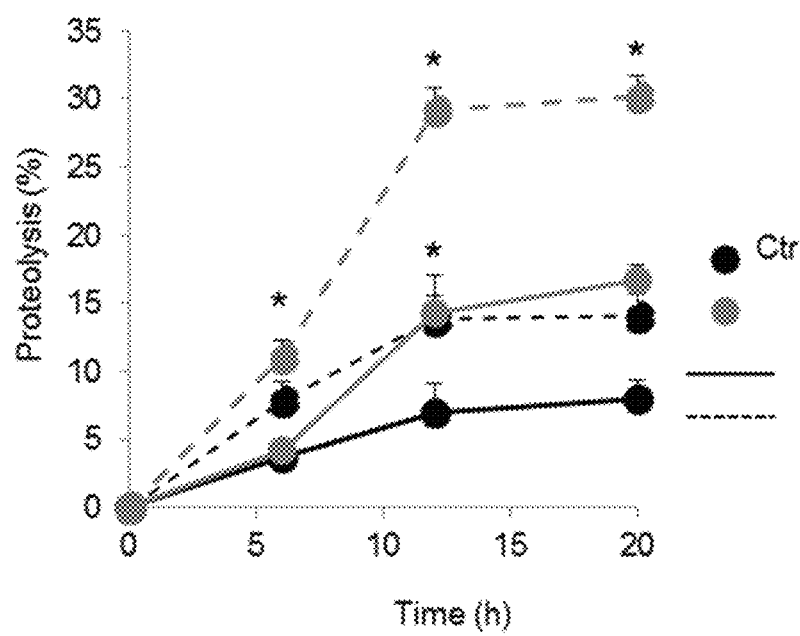
Figure 1C:
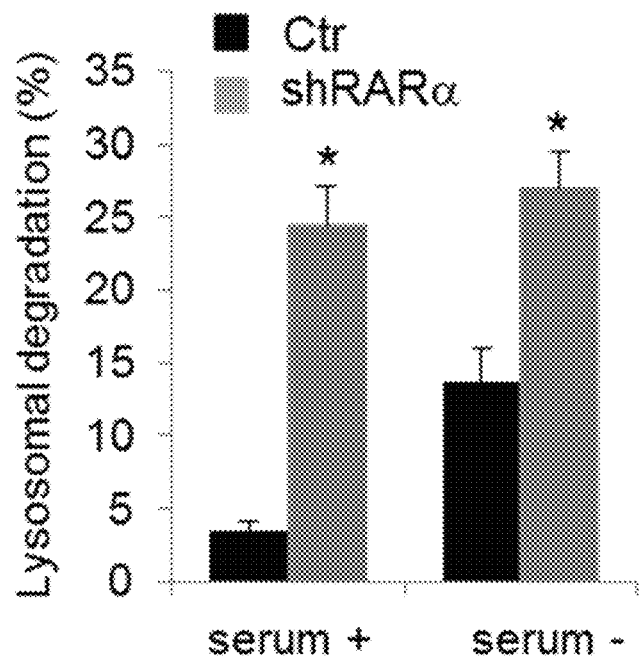
Figure 1D:
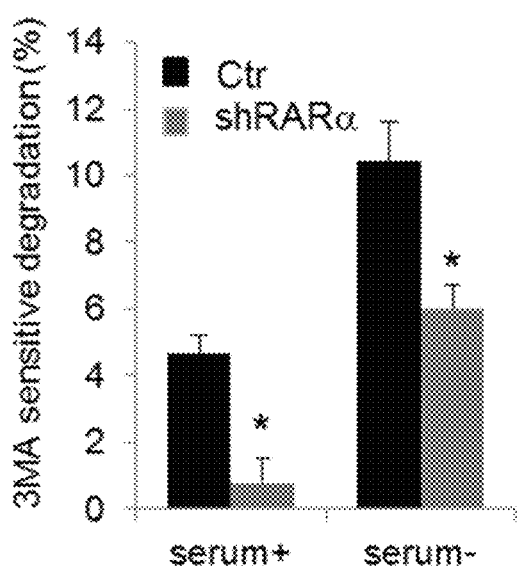

Analysis of the rates of degradation of long-lived proteins, typical autophagy substrates, in control and knock-down cells revealed an increase in protein degradation in RARα (−) cells, when compared to control mouse fibroblasts (FIG. 1b). This increase was evident both under basal conditions and when serum was removed from the culture media to upregulate autophagy. Addition of lysosomal inhibitors demonstrated that most of the increase in both basal and inducible protein degradation in RARα (−) cells was of lysosomal origin (FIG. 1c). However, the percentage of protein degradation sensitive to 3-methyladenine, a well-characterized inhibitor of macroautophagy, was significantly reduced in RARα(−) cells (FIG. 1d), suggesting that the observed increase in lysosomal degradation was not attributable to upregulation of macroautophagy.

Figure 2A:
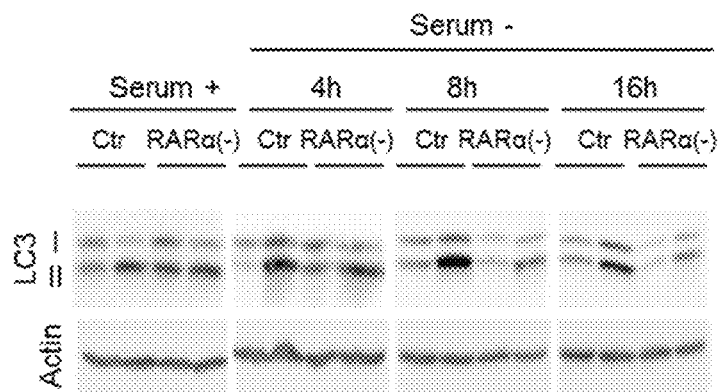
FIG. 2A-2C. Effect of knock-down of RARα on macroautophagy. (a) Immunoblot for LC3-II of mouse fibroblasts control (ctr) or knocked-down for RARα (RARα (−)) maintained in the presence or absence of serum for the indicated times. Where indicated protease inhibitors (PI) against lysosomal proteolysis were added. Actin is shown as loading control. (b) Levels of LC3-II determined by densitometric quantification of immunoblots. Values are expressed as folds values in serum supplemented control cells (n=4). (c) Ratio of levels of LC3-II in cells treated with PI compared to untreated cells. Values are expressed as fold untreated (n=4). All values are mean+S.E. Differences with control (*) cells are significant for *$p<0.05$.
Figure 2B:
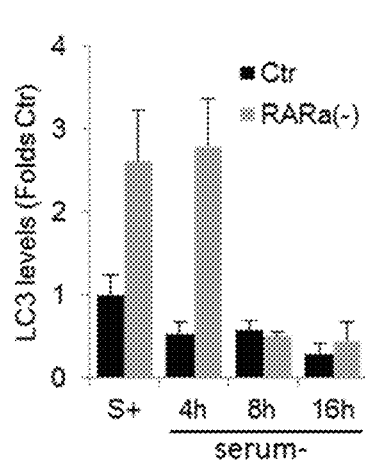
Figure 2C:
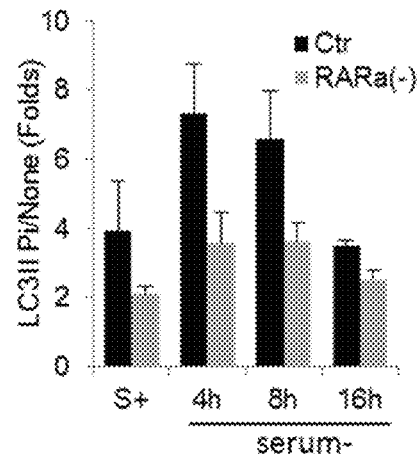

To directly analyze macroautophagy, a widely accepted assay was used to measure activity of this pathway based on the analysis of the intracellular levels and degradation of the lipid-conjugated form of the light chain protein type 3 (LC3-II), a constitutive component of autophagosomes[29]. Steady-state levels of LC3-II provide information on the amount of autophagosomes present in a cell at a given time, whereas the amount of LC3-II that accumulates upon blockage of lysosomal proteolysis allows measuring the efficiency of fusion and degradation of autophagic vacuoles by lysosomes (autophagic flux). RARα(−) cells displayed significantly higher levels of LC3-II both under basal and inducible conditions when compared with control cells (FIGS. 2a and b). Immunofluorescence for LC3 in these cells confirmed the presence of higher content of LC3-positive vesicles in the cells defective for RARα. These vesicles were confirmed to be autophagosomes using a double tagged form of LC3 (mCherry-GPF-LC3) that due to quenching of GFP fluorescence at low pH highlights autophagosomes in yellow and lysosomes in red. The content of double labeled vesicles was significantly higher in RARα(−) cells when compared with control cells. An increase in autophagosome content can result from increased formation of these organelles (autophagosome induction) or from reduced clearance of autophagosomes by lysosomes. To differentiate between both possibilities, the autophagic flux was compared in control and RARα(−) cells. Immunoblot (FIGS. 2a and c) and immunofluorescence for endogenous LC3 revealed significantly reduced increase in levels of the autophagosome-associated form of this protein upon blockage of lysosomal degradation and a reduction in the number of single labeled vesicles (lysosomes) when using the double tagged form of LC3. These results support that elimination of signaling through the RARα receptor reduces macroautophagy activity, in agreement with the previously described stimulatory effect of retinoic acid on this autophagic pathway[25,27,28].

Because the observed downregulation of macroautophagy upon RARα knock-down cannot explain the increase in lysosomal degradation observed in these cells (FIG. 1c), the effect of this intervention on CMA was measured. Activation of this selective autophagic pathway can be determined using a photoactivable (PA) reporter fused to the CMA-targeting motif (KFERQ-PA-mcherry1)[30]. Activation of CMA favors mobilization of this artificial CMA substrate from the cytosol to lysosomes, which can be tracked as a change in the reporter fluorescence from a diffuse to a punctate pattern[30]. Fluorescence analyses of cells transfected with the CMA reporter revealed a significantly higher number of fluorescent puncta per cell in RARα(−) cells, both in the presence or absence of serum when compared to control cells. These results suggest that the increase in lysosomal degradation observed upon RARα blockage was, for the most part, a consequence of CMA upregulation, and support an inhibitory effect of RARα signaling on both basal and inducible CMA.

Figure 3A:
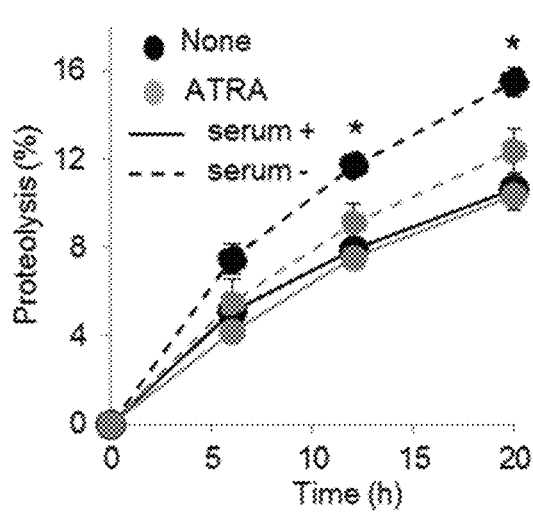
FIG. 3A-3C. Effect of all-trans-retinoic acid (ATRA) on autophagy. (a) Rates of degradation of long-lived proteins in mouse fibroblasts untreated (None) or treated with (40 μM) ATRA and maintained in the presence or absence of serum. Values are expressed as percentage of proteolysis. (n=3) (b) Percentage of lysosomal degradation calculated after treatment with inhibitors of lysosomal proteolysis for 12 h (n=3). (c) Immunoblot for LC3-II of the same cells maintained in the presence or absence of serum and protease inhibitors (PI). Left: representative immunoblot. Actin is shown as loading control. Bottom: Ratio of levels of LC3-II in cells treated with PI compared to untreated cells. Values are expressed as fold untreated (n=4). All values are mean+S.E. and differences with untreated cells are significant for * $p<0.01$.
Figure 3B:
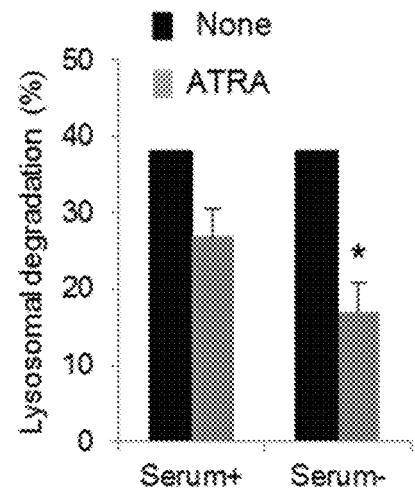
Figure 3C:
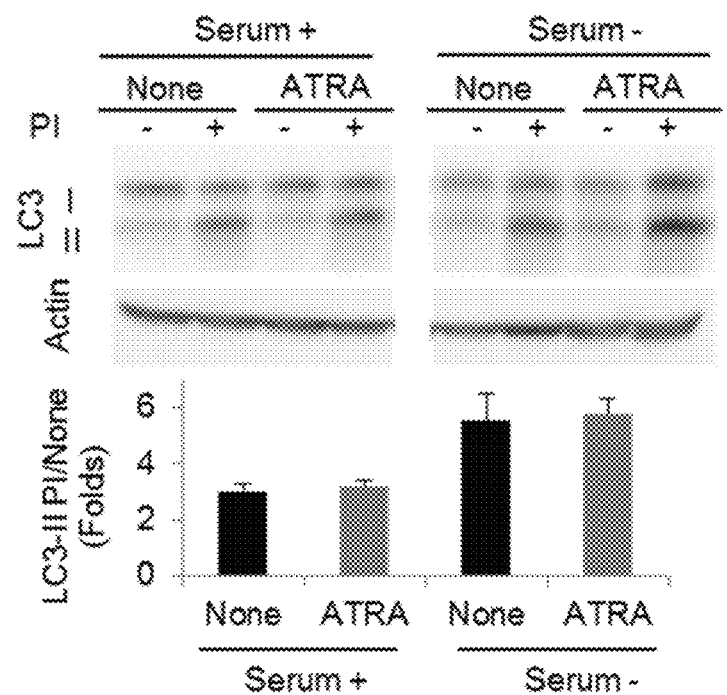

To further confirm the opposite effect of RARα signaling on different autophagic pathways and the possible inhibitory effect of signaling through this receptor on CMA, similar experiments were performed in cells treated or not with all-trans-retinoic acid (ATRA), a potent activator of RARα signaling. ATRA supplementation of mouse fibroblasts did not affect total rates of protein degradation under basal conditions, but significantly reduced the increase in protein degradation normally observed in these cells in response to prolonged serum removal (FIG. 3a). Addition of inhibitors of lysosomal proteolysis confirmed that both basal and inducible lysosomal degradation were significantly compromised after ATRA supplementation (FIG. 3b). In contrast to the reports in other cell types[25,27,28], there were no significant changes in steady state levels of LC3 or in its lysosomal flux analyzed by immunoblot (FIG. 3c) or with the more dynamic mcherry-GFP-LC3 reporter, supporting the previously proposed cell-type dependent stimulatory effect of retinoids on macroautophagy. Analysis of CMA using the CMA reporter revealed that treatment with ATRA did not have a noticeable effect on basal CMA but significantly reduced the activation of this pathway in response to serum removal. Overall these findings support that ATRA and RARα signaling exert an inhibitory effect on CMA activity.

Design and Synthesis of RARα Antagonist with Selective Effect on CMA.

Previous reports have revealed that the effect of ATRA on macroautophagy was not exerted through RAR signaling, as it was independent of the presence or absence of these receptors[28]. Signaling through RARα was not behind the observed inhibitory effect on autophagic degradation of cytosolic proteins, because it was still detectable when RARα(−) cells were supplemented with ATRA. In contrast, the inhibitory effect of ATRA on CMA was dependent on the RARα, as ATRA treatment no longer inhibited CMA activity in RARα(−) cells. The marked upregulation of CMA observed when RARα was eliminated, the opposite effects of this intervention on macroautophagy activity, and the fact that part of the effect of ATRA on autophagy was not mediated through RARα signaling led to the present proposal that it may be possible to design RARα-targeted compounds capable of upregulating CMA activity without affecting other autophagic pathways. Furthermore, since RARα has the capability to activate and repress target-gene transcription, and the molecular determinants of this repression have been recently identified[31], the aim was to identify antagonist molecules selective for this repressor activity of RARα. To this effect, structure-based chemical design strategies and novel chemistry were used to generate a small library of retinoic acid derivatives.

Figure 4A:
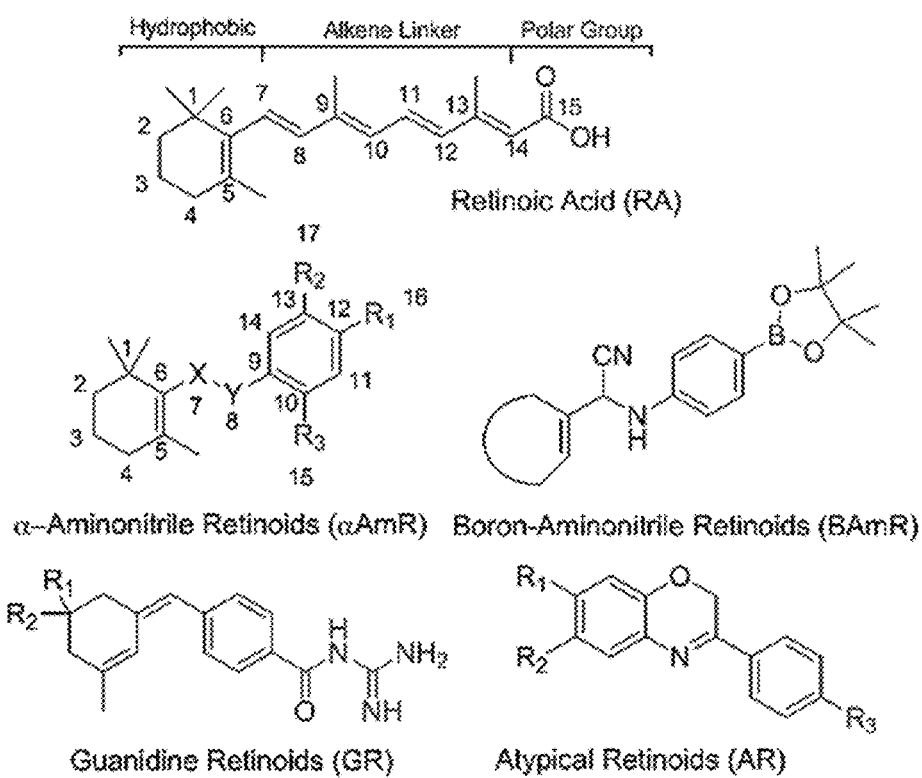
FIG. 4A-4D. Design, Synthesis and molecular docking of RARα Targeting Compounds. (a) Molecular structure of all-trans-retinoic acid (left) highlighting three different regions: the hydrophobic ring, the polyene linker "connector", and the carboxylic acid moiety. The basic structure of the four families of compounds generated through modifications of ATRA using structure-based chemical design strategies are shown. Numbering is shown in the retinoic acid and the α-aminonitrile retinoid backbone to indicate how these positions have been conserved in the new molecules. (b) Synthetic reaction schemes for the two novel guanidine retinoids (GR1 and GR2) and the a typical retinoid (AR7). (c-e) Molecular docking of the AR7 (c), GR1 (d) and GR2 (e) compounds in the RARα binding pocket. A close view of the RARα binding pocket in ribbon and interacting residues in stick for each compound docked in the lowest-energy docking pose I is shown. Compounds are docked to a hydrophobic region of the RARα binding pocket formed by α-helices H3, H10 and H12, which is associated with antagonism and blocking of the active RARα conformation. All compounds form extensive hydrophobic interactions with hydrophobic residues of the RARα binding pocket. Hydrogen bonds are formed from the guanidinium group of GR1 and GR2 to side-chain hydroxyls of Ser229 and Thr233, and backbone carbonyl oxygen of Pro407.
Figure 4B:
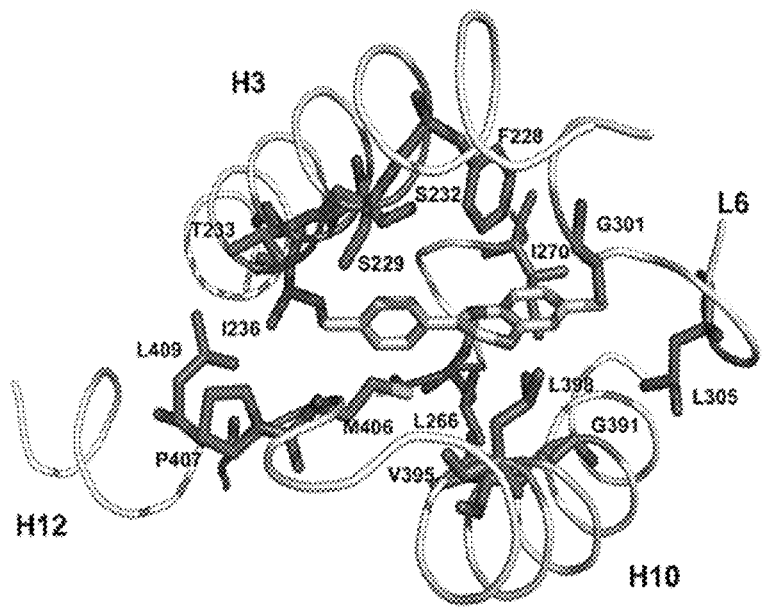

Using the structure of ATRA, chemical changes were introduced to protect the regions of this molecule most prone to intracellular modifications and to enhance ATRA reactive properties with RARα. FIG. 4a depicts the three basic domains common to all retinoid molecules: a hydrophobic component, an all-trans-configured alkene linker, and a polar group (the carboxylic acid moiety)[22]. The alkene linker region is sensitive to photochemical changes[21] and to oxidation at the allylic C4 position in the trimethylcyclohexyl ring by enzymes such as cellular isomerases and cytochrome P450[22].

Through chemical modifications using structure-based chemical design approach, a library of 29 retinoic acid-related compounds was generated that was grouped in four different families: α-aminonitrile retinoids (αAmR), boron-aminonitrile retinoids (BAmR), guanidine retinoids (GR), and atypical retinoids (AR) protected in specific positions (FIG. 4a)[32]. These families contain modifications at the C4 position of the hydrophobic ring, to protect it from possible oxidation to 4-oxo, and in general shortened alkene linkers, which are susceptible to photoisomerization (FIG. 4a; the portions of the molecules where the compounds differ are highlighted and the conserved typical retinoid regions are highlighted). The new designed alkene linker conserves its aromaticity in the ring-constrained form. In addition, groups such as —CN, —NH or the boron atom were incorporated with the aim of enhancing ATRA-reactive properties (for example, $sp^2/sp^3$ hybridization of the boron group can facilitate formation of hydrogen or covalent bonds). The structures of all the compounds generated for the library and their synthetic schemes are shown in Table 1.

Before analyzing the effect of the library compounds on CMA, the effect of increasing concentrations of each of them on cellular viability was determined. Except for four compounds that showed toxic effects at all concentrations tested (data not shown), for most compounds toxicity was not clearly manifested until concentrations ≥50 µM. Consequently, for all subsequent testing, compounds were used at 20 µM, which resulted in less than 20% decrease in cellular viability and no evidence of apoptosis induction in using annexin V labeling in serum deprived cells. The effect of all the compounds in the library on CMA was screened using mouse fibroblasts expressing the CMA reporter. For those compounds showing a positive effect with the CMA reporter (increase in the number of fluorescent puncta in cells maintained in the presence of serum higher than 2.5-fold), changes in total protein degradation were validated using metabolic labeling. This combined analyses identified marked activation of CMA activity in cells treated with compounds AR7, GR1, and GR2 in a dose-dependent manner. The schemes of the synthetic reactions for the generation of these three compounds are shown in FIG. 4$b^{32}$. NMR data show that GR1 compound had a mixture of isomers with E- and Z-stereoselectivity in 2:1 ratio whereas in GR2 the major isomer was E and the minor Z in a 1:0.2 ratio.

Figure 5A:
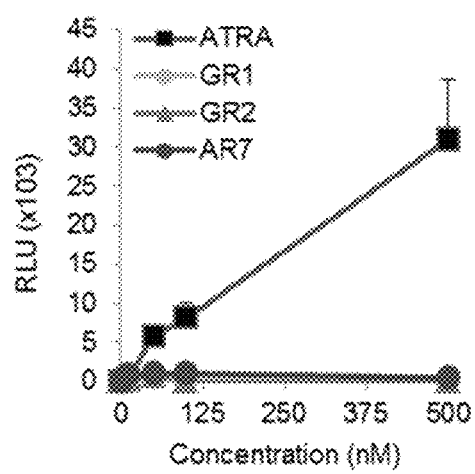
FIG. 5A-5E. Effect of novel retinoid derivates activators of CMA on RARα activity. (a-d) Mouse fibroblasts were co-transfected with the hRARα receptor construct (a, b) or the hRXR receptor (c,d), a relevant reporter luciferase plasmid and the non-retinoid regulated renilla reporter to control for transfection. Values show luciferase units detected in cells subjected to: (a, c) the indicated concentrations of ATRA and the three retinoid-derivatives for 12 h. (b, d) 100 nM (b) or 10 μM (d) ATRA alone (ATRA) or in the presence of the indicated concentrations of the three retinoid derivatives or the antagonist BMS614. Values show luciferase intensity expressed as percentage of that in cells treated only with ATRA and Ki are shown on the right (n=4-6). (e) Immunoblot for LC3 of cells treated with 20 μM of the retinoid derivatives and protease inhibitors (PI), as labeled. Actin is shown as loading control. Levels of LC3-II in untreated cells (left) and increase after PI treatment (LC3-II flux) (right) were calculated from the densitometric quantification of immunoblots. Values are mean+S.E. (n=3).
Figure 5B:
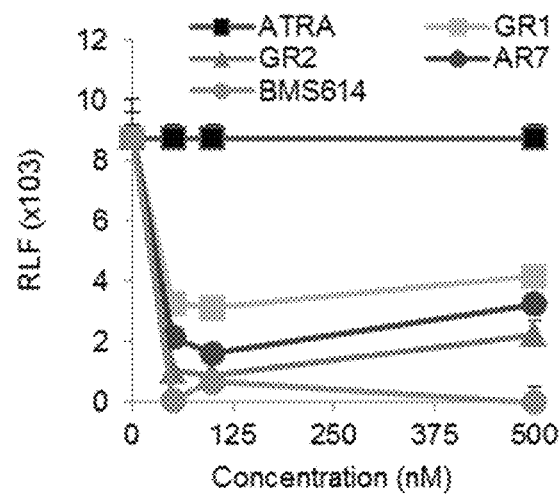
Figure 5C:
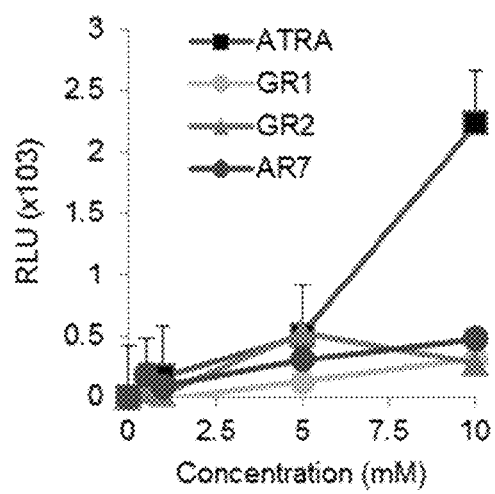
Figure 5D:
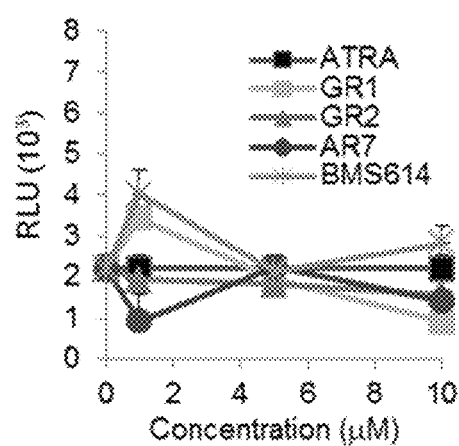

To determine the effect of these molecules on RARα signaling, cells were co-transfected cells with a plasmid coding for RARα fused to the Gal4 DNA-binding domain and a Gal4-dependent luciferase reporter. In contrast to the dose-dependent activation observed in cells treated with ATRA, similar doses of the three compounds that activate CMA did not have any effect on luciferase activity (FIG. 5a), whereas some compounds in the other families in the library (αAmR and BAmR) displayed discrete activity. When administered in combination with ATRA, these compounds had a marked inhibitory effect on the ATRA-dependent activation of luciferase (FIG. 5b). In fact, GR2 and AR7 were among the most potent antagonist compounds in the library. Using a similar luciferase-based reporter for RXR, although some compounds in the library (αAmR family) exhibited activity through this receptor, none of the three leading compounds had significant agonist or antagonist activity on this receptor (FIG. 5c,d).

Figure 5E:
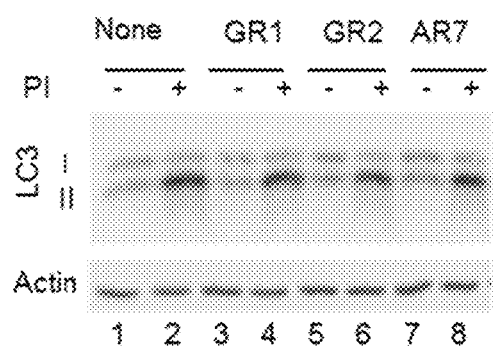

The RAR antagonistic potency of the three leading molecules was close to that of the bona fide antagonist BMS614 (FIG. 5b). In fact, BMS614 also enhanced CMA activity, but whereas this antagonist inhibited macroautophagy, none of the compounds significantly affected autophagosome content or their clearance by lysosomes (FIG. 5e). These results confirm that the novel retinoid derivatives act as RARα antagonists and are capable of upregulating CMA without affecting macroautophagy.

Stimulatory Effect of the Novel Retinoid Derivatives on CMA.

Figure 6A:
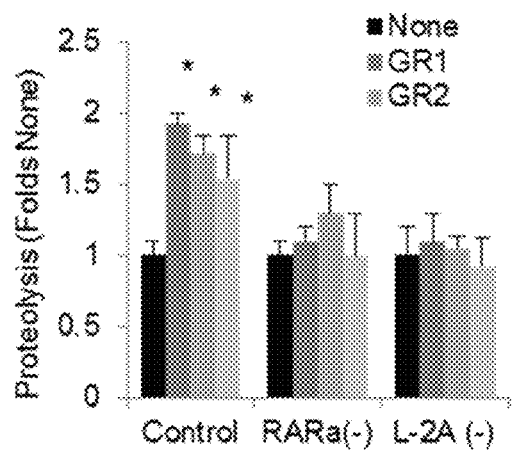
FIG. 6A-6C. Characterization of the effect of the novel retinoid derivates on CMA. (a) Rates of degradation of long-lived proteins in mouse fibroblasts control or knocked-down (−) for RARα or for LAMP-2A and left untreated (None) or treated with (20 μM) the indicated compounds. Values are expressed as folds the proteolytic rate in untreated cells for each group. (n=3) (b-c) Mouse fibroblasts control (Ctr) knocked-down (−) for RARα, LAMP-2A or LAMP-2B were transfected with the KFERQ-mcherry1 photoactivable reporter and supplemented or not with the indicated compounds (20 μM). Average number of fluorescent puncta per cell quantified in >50 cells in at least 4 different fields. No puncta was detected in LAMP-2A(−) cells. All values are mean+S.E. Differences with untreated samples (*) are significant for * p<0.01.
Figure 6B:
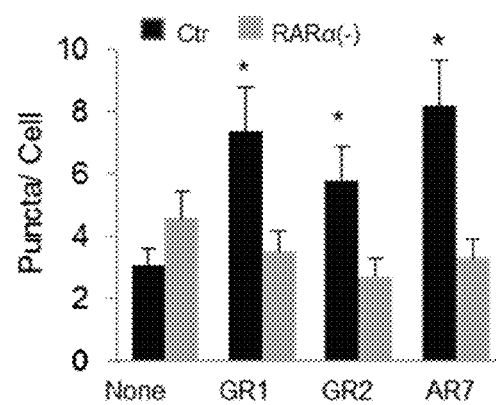
Figure 6C:
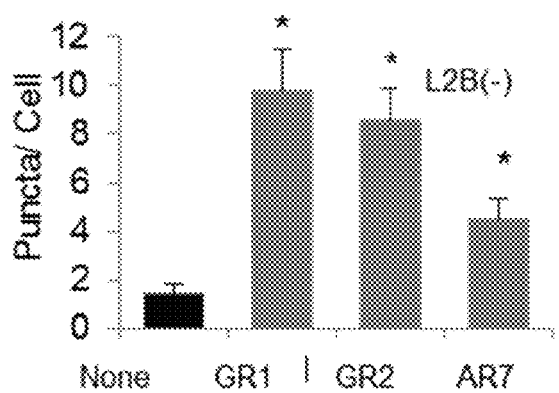

The effect on autophagy of the three novel RARα antagonist compounds generated in this study was further characterized. Using RARα knock-down cells, the stimulatory effect of the new derivatives on total protein degradation (FIG. 6a) and on CMA (FIG. 6b) was confirmed to be dependent on the presence of RARα. Thus, although both activities were higher in the RARα(−) cells, addition of the retinoid derivatives no longer had a stimulatory effect. The increase in protein degradation (FIG. 6a) and in the amount of CMA-positive puncta per cell (FIG. 6b) induced by the retinoid derivates was also confirmed to be a result of activation of CMA, as their effect was abolished in cells knocked down for the lysosomal CMA receptor, and consequently incapable of carrying on CMA[33]. In contrast, these compounds were still capable of effectively activating CMA in cells knocked-down for LAMP-2B, a protein with 85% homology to LAMP-2A but that does not participate in CMA (FIG. 6c).

To start elucidating the basis for the differences in the antagonistic effect on RARα activity of the new retinoid derivatives when compared with other well characterized antagonist molecules, molecular docking and molecular dynamics simulations were performed with the three leading compounds. Molecular docking studies of the compounds were performed with the RARα X-ray crystal structure in the inactive coformation[31]. Docking studies revealed that the three leading compounds may bind with two different orientations (pose I and pose II) in the ligand-binding site of the RARα receptor. Both docking orientations demonstrate that AR7, GR1 or GR2 do not interact or are in close distance with the catalytic Arg272, a feature that is common to ATRA and other known agonists and antagonists. The binding site in docking pose I is formed by residues of helices H3, H10 and H12 and in pose II by residues of helices H3, H10 and H5. As a result, the compounds adopt opposite orientation in poses I and II and have a small overlap of interacting residues. Docking also revealed that both E- and Z-isomers of GR1 and GR2 can bind with the two different poses I and II and that E- and Z-isomerization have a minimal impact on the docked structure of these compounds suggesting that both isomers can be active RARα antagonists.

Figure 4C:
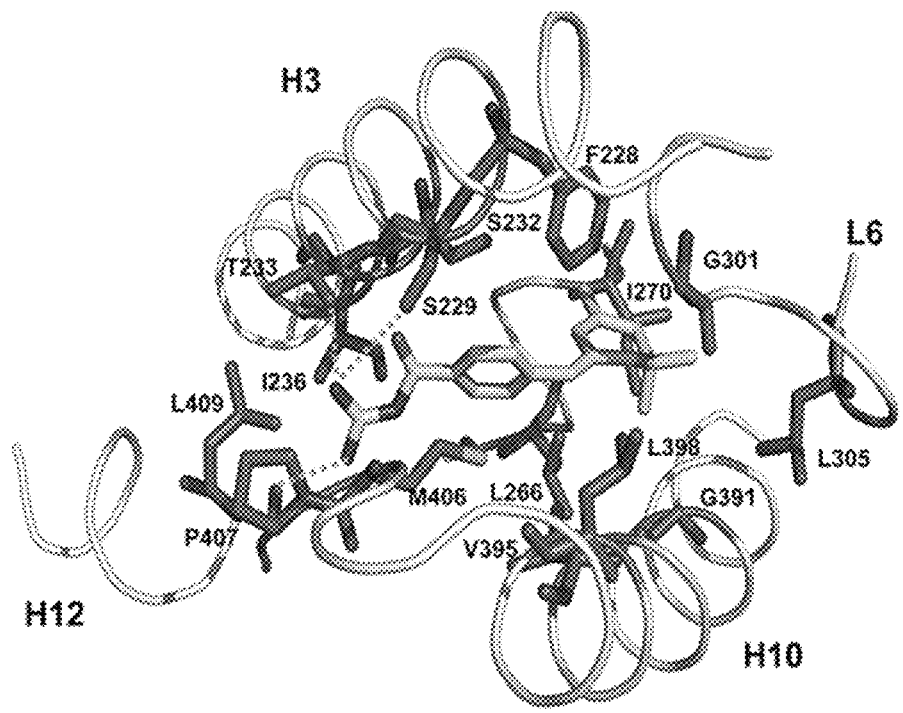

Analysis of docking and molecular dynamics simulations favorably suggests that the compounds adopt a binding mode, as shown in FIGS. 4c and d. In this docking orientation, the compounds are placed at the junction of α-helices H12, H3 and H10. This is an interesting docking orientation that is consistent with the functional activity of the compounds and mimics a portion of the known antagonist BMS614 when is bound to RARα[13]. The compounds form extensive hydrophobic interactions with the hydrophobic residues of the site suggesting stabilizing-interactions with the open conformation of the α-helix H12 that regulates recruitment of RARα co-regulators. Compounds would have steric clashes with the α-helix H12 in the closed conformation when RARα is in active mode. Additionally, docking suggests that the guanidinium group of compounds GR1 and GR2 can form hydrogen bonds with the carbonyl backbone of Pro407 in α-helix H12 and the hydroxyl group of Thr233 in α-helix H3. Thus, docking positions the compounds in a critical region of the RARα binding site to stabilize its inactive conformation. This binding region is geographically distinct from the ATRA binding site and may account for the selectivity of the compounds for RARα.

The result of the two possible docking orientations can be explained by the small size of the lead molecules compared to the RARα binding site and the high complementarity of hydrophobic interactions between the compounds and the RARα residues in the two docking orientations. It was hypothesized that it would be possible that AR7 and the GR compounds could bind simultaneously to the RARα binding site. To experimentally test this possibility, the effect on CMA of AR7 and GR1 added alone or in combination was analyzed. A marked increase in their CMA activating potency was found when the same final concentration was reached by combining both molecules, supporting a cooperative effect of these two compounds when added together. Thus, the potential ability of the AR7 and GR compounds to bind in two orientations, that are still different from the bound pose of ATRA and other known RARα modulators, along with the complexity of ligand-induced changes already described for this receptor—that affect RARα-DNA binding but also modulate dissociation/association of several co-regulatory complexes—could contribute to the different downstream consequences of their antagonistic effect on RARα.

Figure 8:
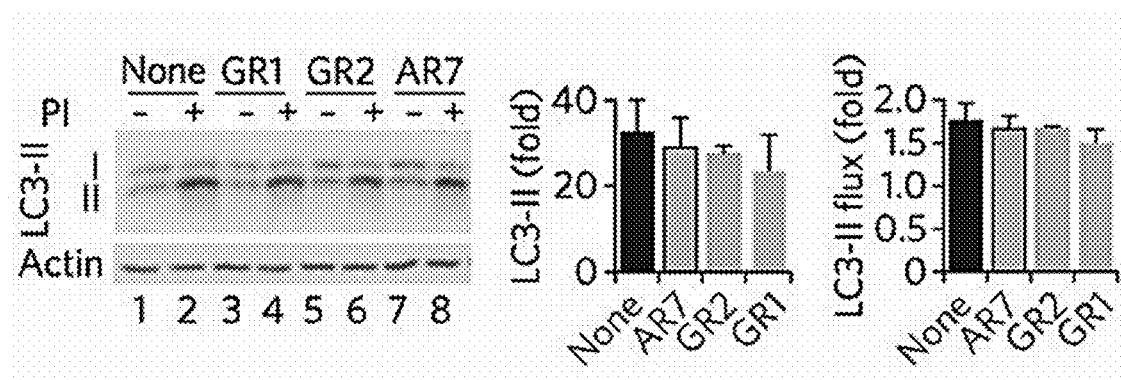
FIG. 8. Immunoblot for LC3 of cells treated with 20 mM of the retinoid derivatives and protease inhibitors (PI), as labeled. Levels of LC3-II in untreated cells (left) and increase after PI treatment (LC3-II flux) (right) were calculated from the densitometric quantification of immunoblots. Values are mean±S.E. (n=3).
Figure 10A:
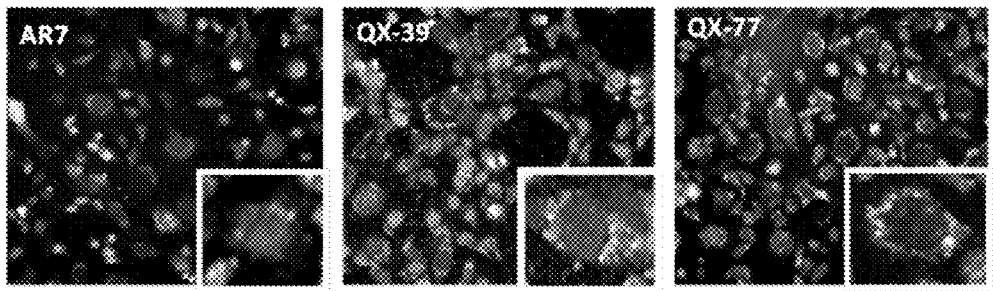
FIG. 10A-10D. Medicinal chemistry refinement for novel a typical retinoid antagonists (ARA). CMA reporter assay in cells treated with AR7 derivatives (20 mM for 12 h). (A) High content microscopy images. Nuclei are highlighted with DAPI. (B) Quantification of number of puncta per cell relative to AR7 treatment. (C) Structure of the original molecule (AR7) and two preferred compounds regarding potency and selectivity. (D) Dose-dependence of the original molecule and two preferred compounds. Values are mean+s.e.m. n=3 experiments with triplicate replica.
Figure 10B:
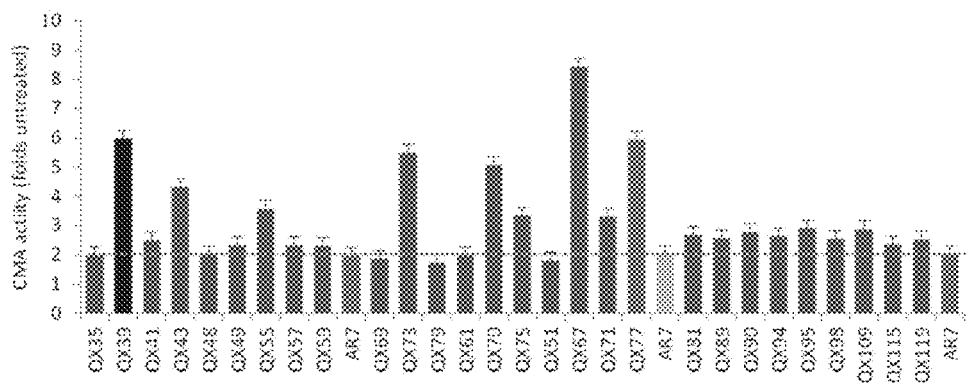
Figure 10C:
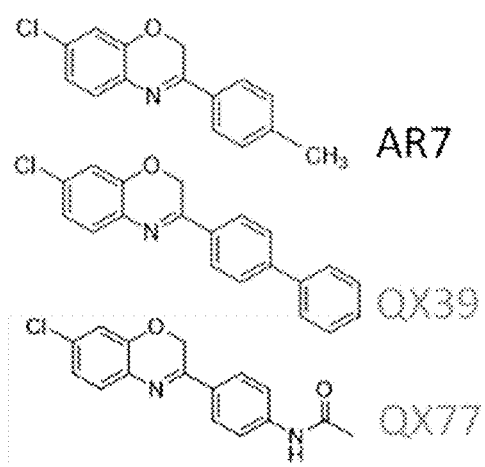
Figure 10D:
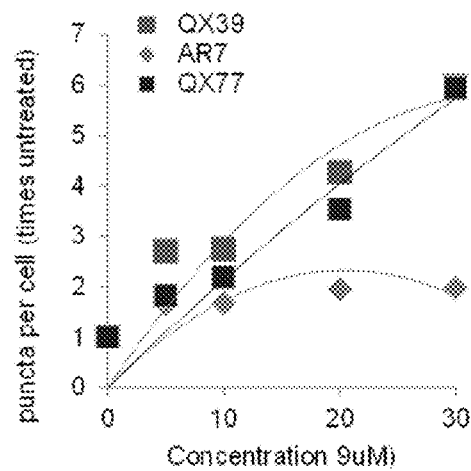
Figure 11:
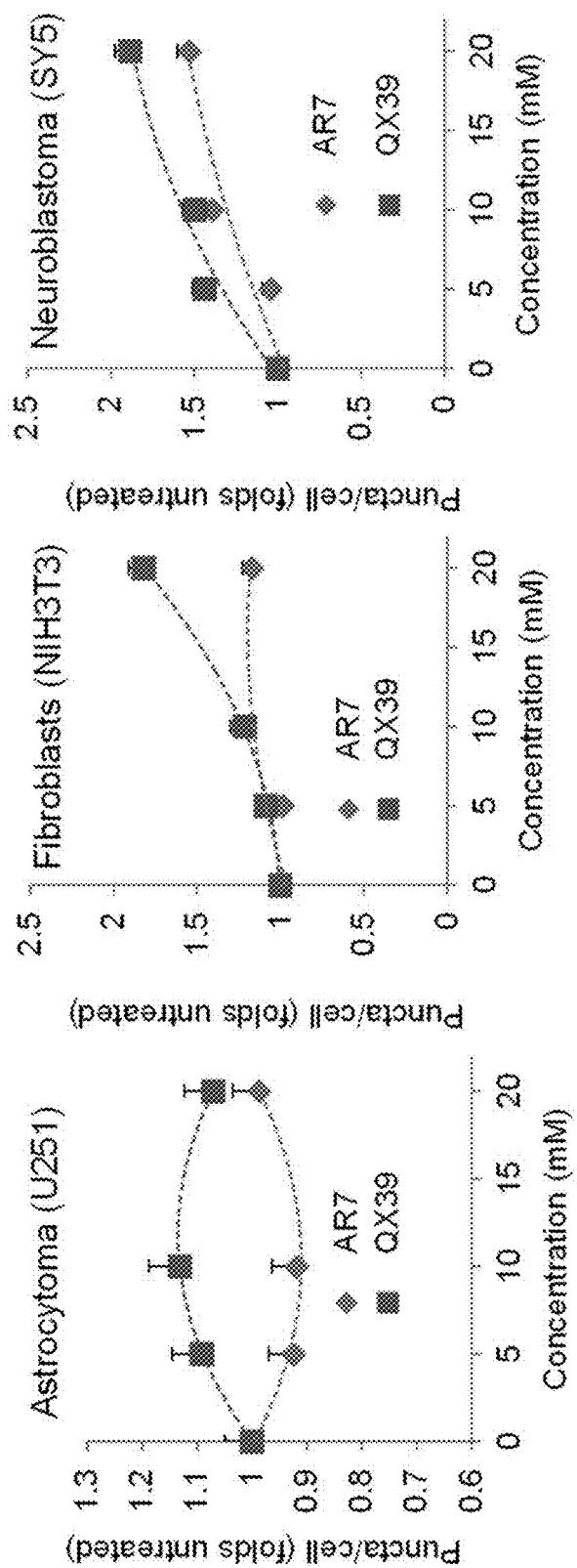
FIG. 11. CMA activation in different cell types by a typical retinoid antagonists (ARA). CMA reporter assay in the indicated cell lines treated with AR7 and its derivative QX39 (20 mM for 12 h). Values are mean+s.e.m. n=3 experiments with triplicate replica.
Figure 12A:
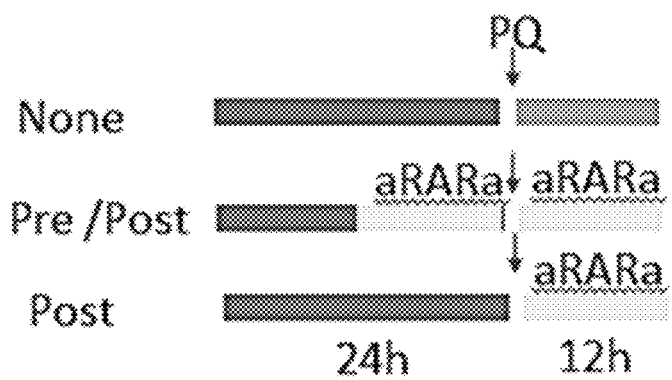
FIG. 12A-12C. Protective effect of a typical retinoid antagonists (ARA). (A) Experimental design: NIH3T3 cells were exposed to increasing concentrations of paraquat (PQ) to induce oxidative stress. ARA where added in conjunction with the stressor or where indicated, also before the stressor. (B-C) Analysis of cell viability in the two experimental paradigms shown in (A), to show that whereas the original ARA need to be added before the insult to have maximal protective effect, the new ARA show protection even without pre-treatment. Values are mean+s.e.m. n=3 independent experiments with triplicate wells. *p<0.01
Figure 12B:
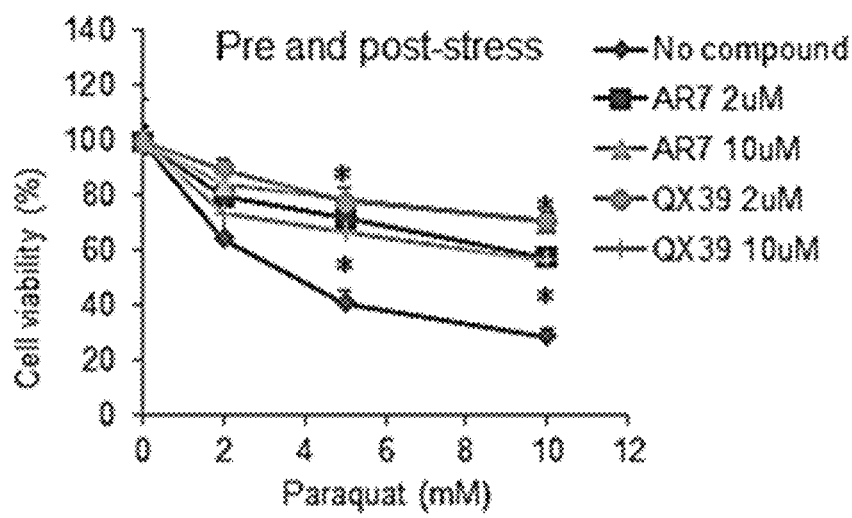
Figure 12C:
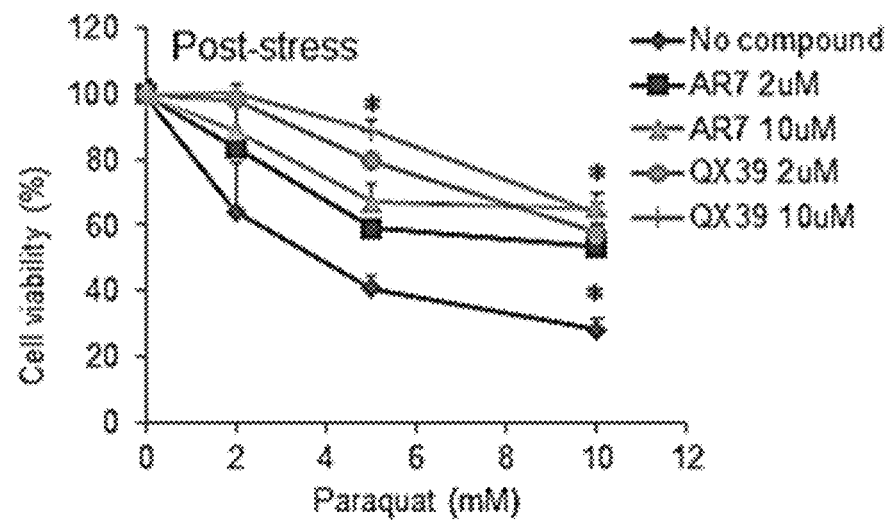
Figure 13A:
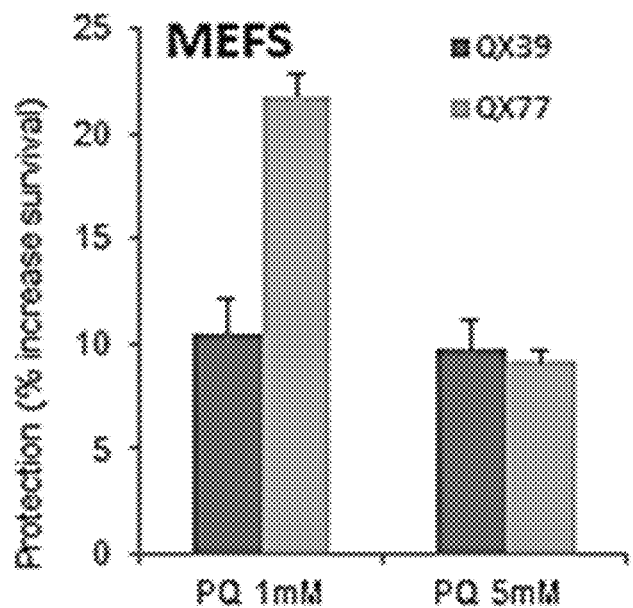
FIG. 13A-13B. Protective effect of a typical retinoid antagonists (ARA) against different stressors in different cell types. Mouse embryonic fibroblasts (A) or neuroblastoma cell lines (B) were subjected to the indicated stressors in the presence or not of the two ARA. Viability was measure at 24 h of the treatment and the protective effect was calculated as the increase in cell viability compared to untreated cells. Values are mean+s.e.m. of n=3 independent experiments with triplicate samples. All values were significantly different (p<0.01) to values in untreated samples.
Figure 13B:
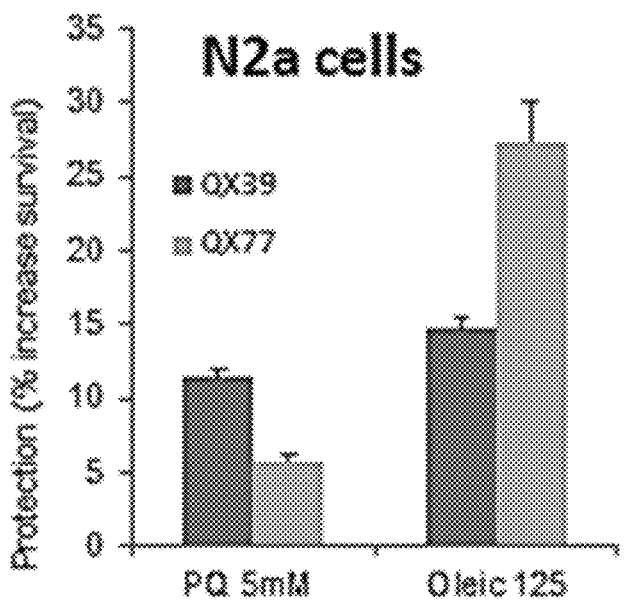
Figure 14:
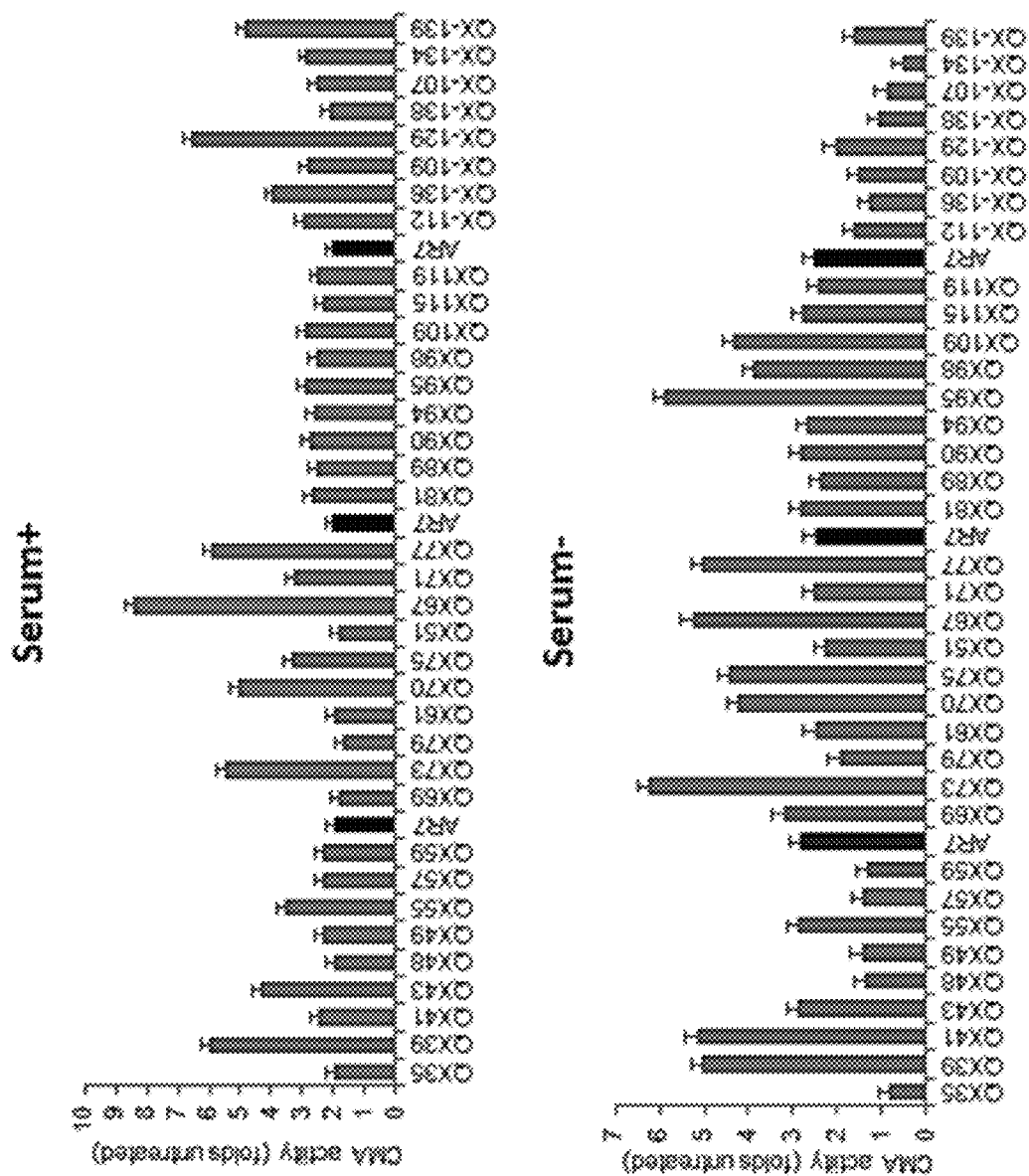
FIG. 14. Medicinal chemistry refinement for a typical retinoid antagonists (ARA). CMA reporter assay in cells maintained in the presence (top) or absence (bottom) of serum and treated with AR7 derivatives (20 mM for 12 h). Quantification of number of puncta per cell relative to AR7.
Figure 15A:
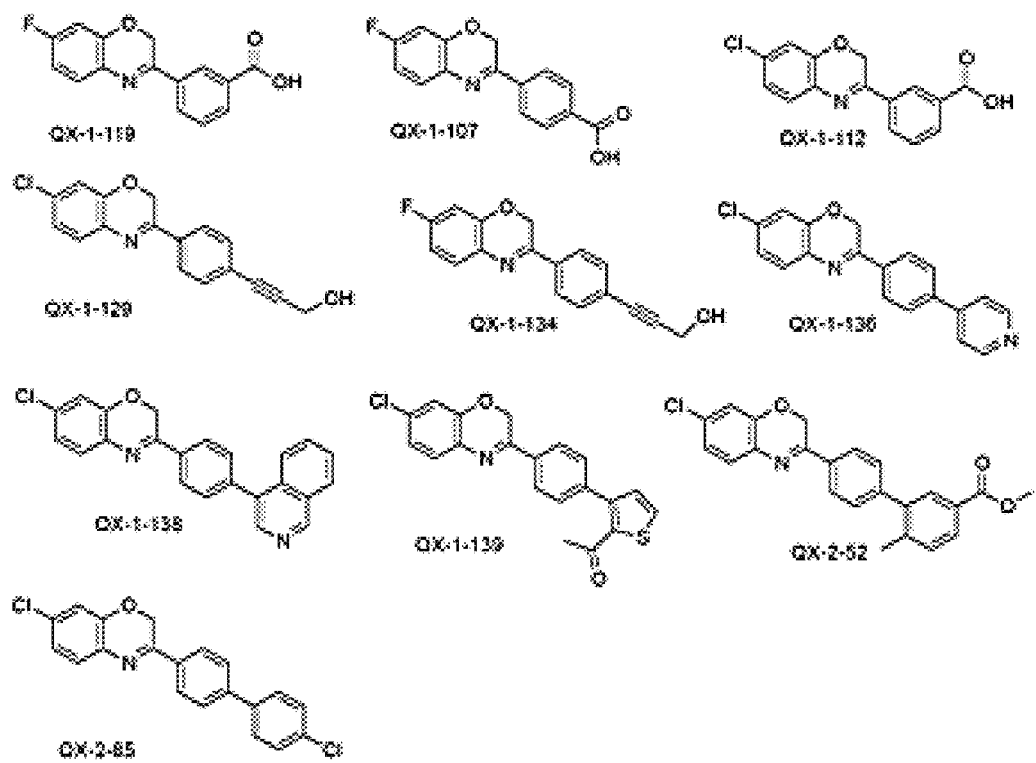
FIG. 15A-15C. Medicinal chemistry refinement for a typical retinoid antagonists (ARA). (A) Structure of ARA. (B-C) CMA reporter assay in cells treated with AR7 derivatives (20 mM for 12 h) while maintained in the presence (B) or absence (C) of serum. Values are mean+s.e.m. n=3 experiments with triplicate replica.
Figures 15B, 15C:
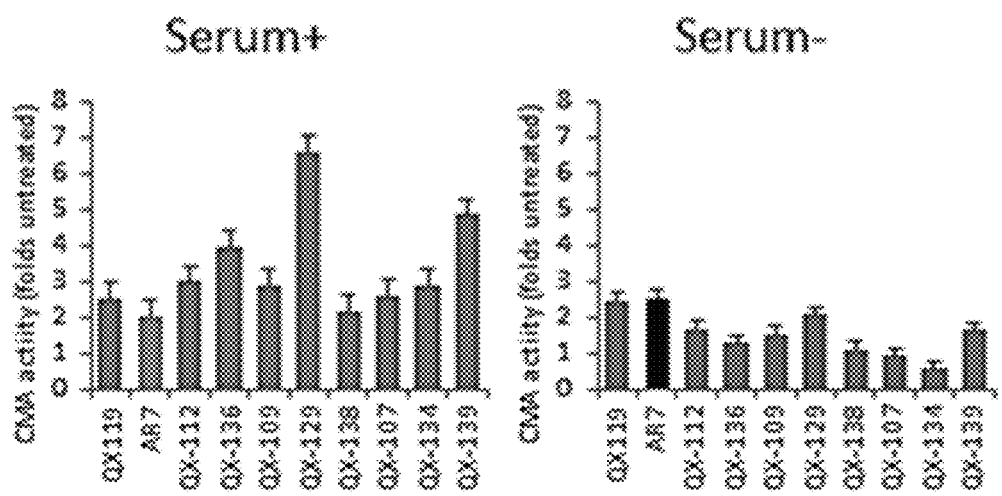
Figure 16A:
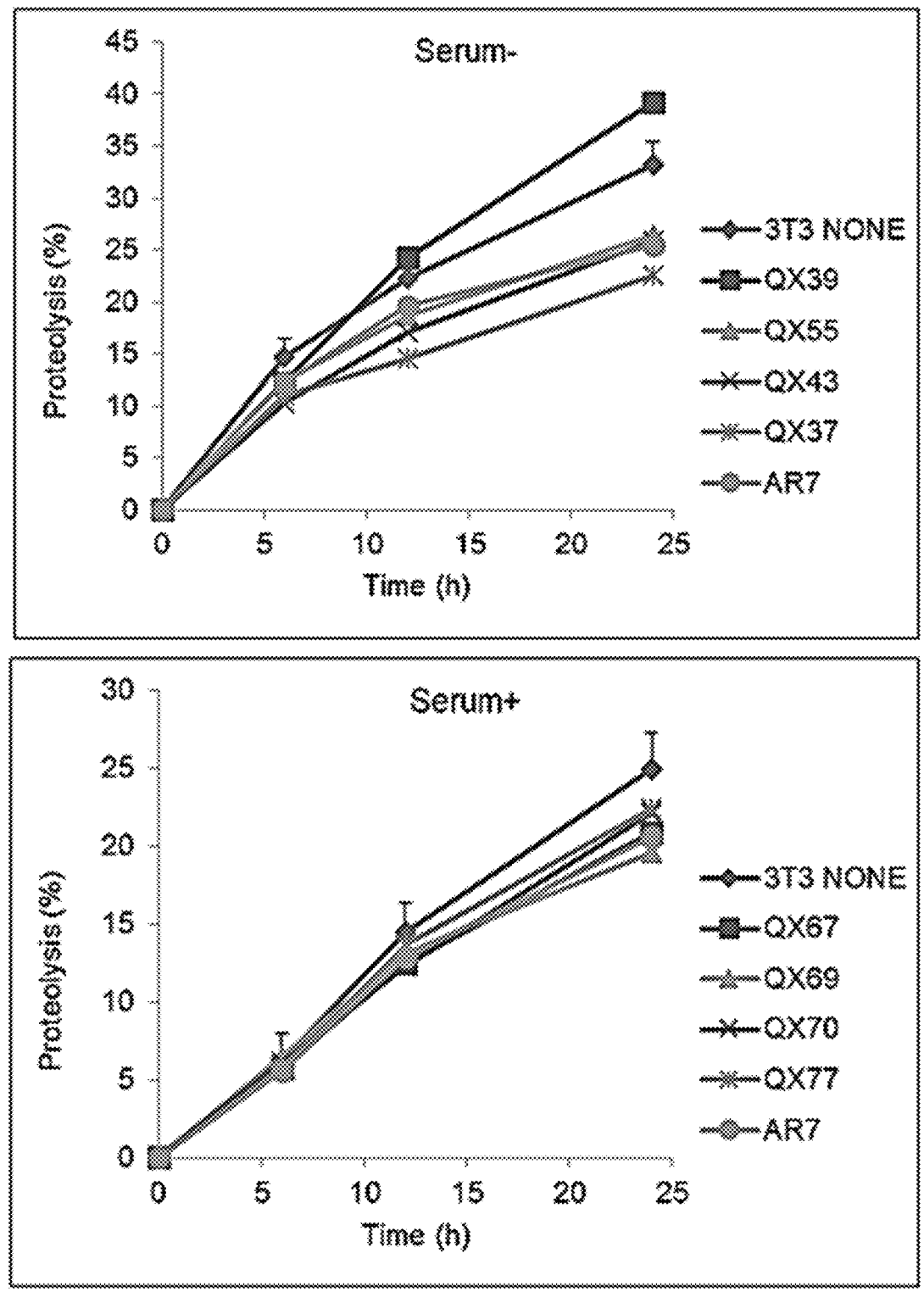
FIG. 16A-16B. Effect of a typical retinoid antagonists (ARA) on total proteolysis and lysosomal degradation measured at difference time points (6 h, 12, and 24 h) in the presence or absence of serum. Values are mean+s.e.m. of n=3 independent experiments with triplicate samples.
Figure 16B:
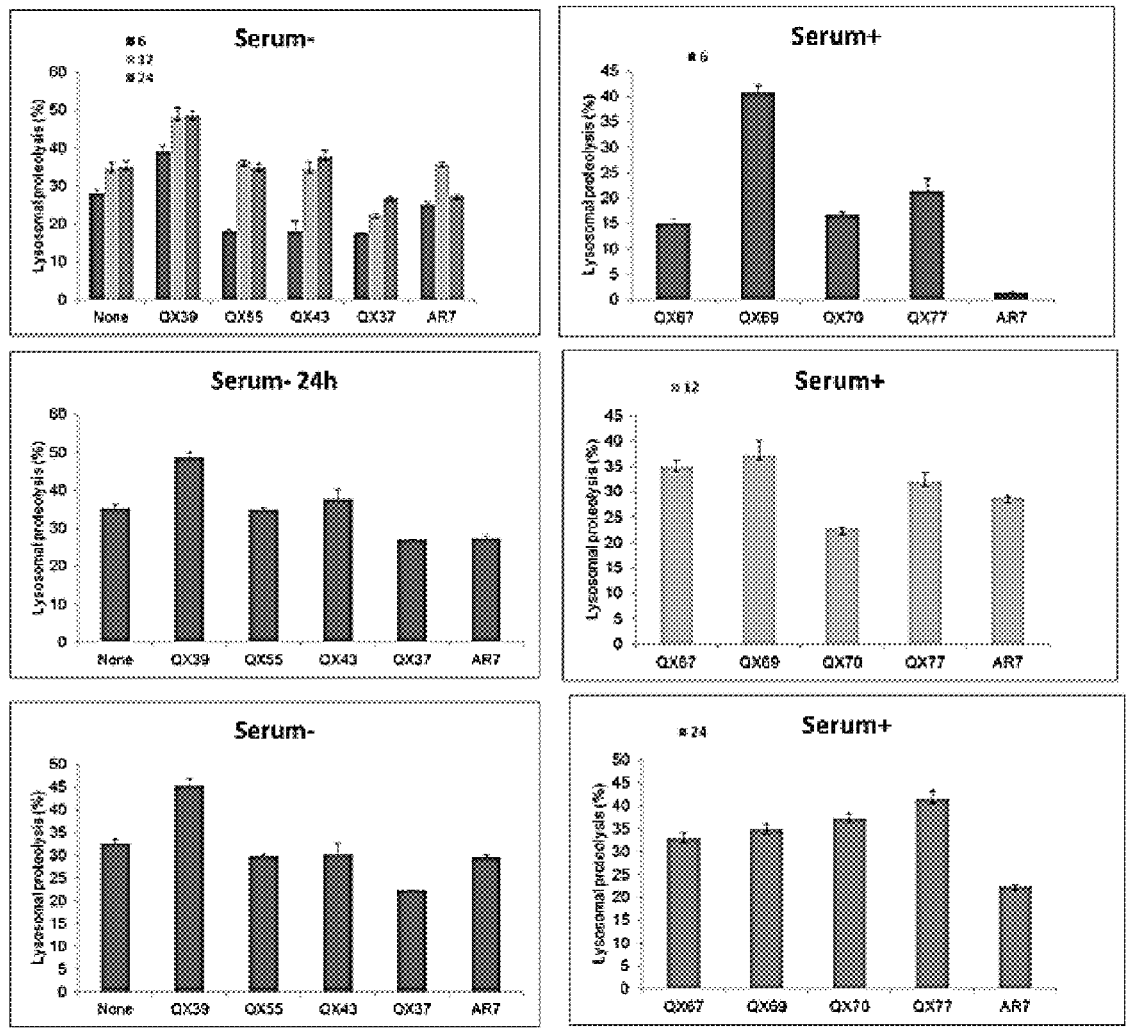

FIG. 8 illustrates the specificity of compounds GR1, GR2 and AR7 toward CMA and the absence of effect on other autophagic pathways (macroautophagy shown here). Contrary to the commercially available retinoic acid antagonists that have a profound inhibitory effect on macroautophagy, it is shown here by measuring LC3 flux that the present compounds do not inhibit macroautophagy.

Protective Effect of the Novel CMA Activators Against Proteotoxicity.

Figure 7A:
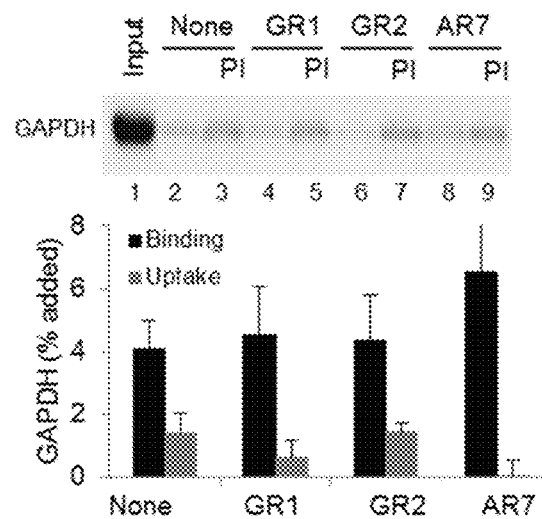
FIG. 7A-7F. Effect of the novel retinoid derivatives over different CMA components and in the cellular response against different stressors. (a) Rat liver lysosomes treated or not with lysosomal protease inhibitors (PI) were incubated with Glyceraldehyde-3-phosphate dehydrogenase (GAPDH) alone (None) or in the presence of 20 μM of the indicated compounds. Immunoblot of samples collected by centrifugation (top) and quantification of the amount of GAPDH bound and taken up by each group of lysosomes (bottom). (n=3). (b) Immunoblot for the indicated proteins in homogenates (Hom) and same lysosomes (Lys) as in a. (c) mRNA levels of LAMP-2A in mouse fibroblasts control (Ctr) or knocked-down (−) for RARα and subjected to the indicated treatments. Values are corrected for actin and are expressed as folds control untreated cells. Differences with untreated samples (*) are significant for p<0.01. (n=4-5). (d) Top: Cellular viability of control mouse fibroblasts exposed to 2 mM PQ or LAMP-2A(−) exposed to 0.5 mM PA and treated with the indicated compounds for 12 h before or after the PQ treatment. Bottom: Cellular viability of mouse fibroblasts knocked down for LAMP-2A and treated with 0.5 mM PQ in the presence of the indicated compounds. (n=3). (e) Viability of mouse fibroblasts transfected with the indicated concentrations of a plasmid coding for α-synuclein and left untreated (none) or treated with 1 mM PQ alone or in the presence of 20 μM AR7. Differences with untreated cells (*) or with cells treated only with PQ (§) were significant for p<0.001. (n=3). (f) Immunoblot for α-synuclein and actin in cells transfected or not with α-synuclein, as labeled, and left untreated (none) or treated with PQ or PQ and AR7. Top: higher exposure blot to highlight oligomeric species. * non specific band. M: monomer; Oligo: oligomers). All values are mean+S.E.
Figure 7B:
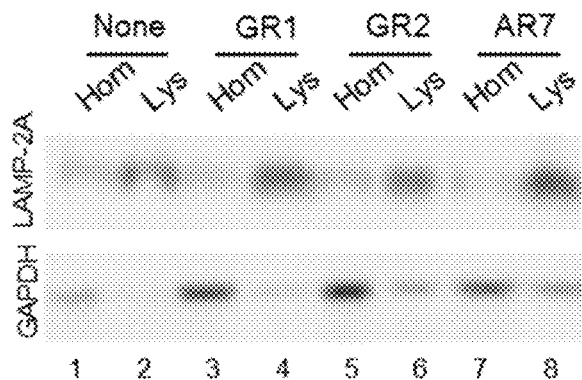

To gain insights on the mechanism by which the new retinoid derivates activate CMA, their effect on the cellular oxidative status was analyzed. Retinoic acid has been shown to exert anti-oxidant effects in a variety of cellular settings[34]. It is thus plausible that inhibition of RARα signaling could result in enhanced oxidative stress, a condition known to activate CMA[35]. Immunoblot with an antibody against carbonylated groups to detect oxidized proteins in cell lysates revealed no differences between cells untreated or after treatment with the different retinoid derivatives. These results make it unlikely that activation of CMA in the treated cells was reactive to an increase in oxidative stress on those cells. It was also analyzed whether the compounds may exert their stimulatory effect on CMA by directly acting on the lysosomal compartment. Pretreatment of intact lysosomes isolated from rat liver with the different retinoid derivates did not increase binding or uptake of the well-characterized CMA substrate glyceraldhehyde-3-phoshpate dehydrogenase (GADPH) in these lysosomes when subjected to a standard in vitro assay for CMA (FIG. 7a). In contrast to this lack of lysosomal effect in vitro, analysis of lysosomes isolated from cells treated with the different retinoid derivatives revealed a higher content of the endogenous substrate GAPDH in this compartment, supportive of enhanced CMA and further supporting that the compounds activate CMA through RARα signaling and not directly by interacting with CMA components in lysosomes (FIG. 7b).

No significant differences were observed on the ability of RARα to translocate to the nucleus in response to ATRA in the presence of the retinoic derivatives disproving a possible inhibitory effect at this level. In fact, addition of AR7 was sufficient to stimulate some relocation of cytosolic RARα to the nucleus. Treatment with the transcriptional repressor Actinomycin D partially reduced the stimulatory effect of AR7 on CMA, supporting contribution of transcriptional changes to the upregulation of CMA.

Figure 7C:
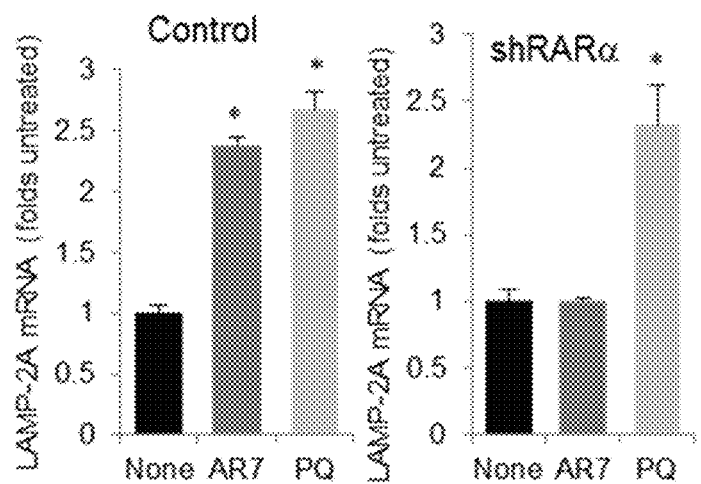

In the search for CMA targets modulated by the retinoid derivatives, the lysosomal receptor LAMP-2A was focused on, as its levels are limiting for CMA. Higher levels of this receptor were found in the lysosomes from the treated cells (FIG. 7b), along with a discrete but significant transcriptional activation of LAMP-2A in these cells, comparable to that previously described in conditions of maximal activation of CMA such as paraquat-induced oxidative stress (FIG. 7c). This transcriptional upregulation was not observed for other lysosomal membrane proteins. LAMP-1 was partially inhibited by treatment with Actinomycin D and was no longer observed in the absence of the RARα (FIG. 7c). No changes in LAMP-2A mRNA levels were found upon stimulation of RARα activity with ATRA under basal conditions, in agreement with the lack of effect of ATRA treatment on basal CMA. However, a significant decrease in LAMP-2A mRNA was found when ATRA was added to cells deprived of serum, a condition in which ATRA treatment reduced CMA activity.

Figure 7D:
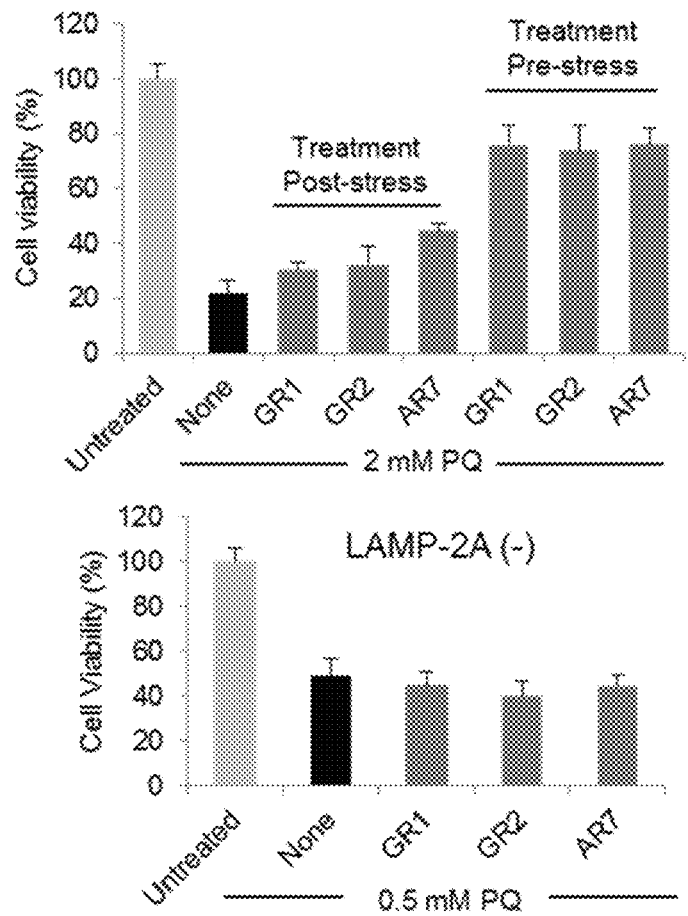

Lastly, the possible beneficial effect of chemical enhancement of CMA with the new retinoid derivatives in cellular homeostasis and its resistance to stress were investigated. To this end, a comparison was made of the sensitivity to the pro-oxidant compound paraquat (PQ) of cells treated with the retinoid derivatives before or right after the oxidative insult. As shown in FIG. 7d, addition of retinoid derivatives to cells exposed to PQ for 4 hours had only a very discrete positive effect on cellular viability. In contrast, when the compounds were added before inducing oxidative stress, a marked improvement in cellular viability was observed (FIG. 7d, top). The enhanced resistance to the oxidative insult in retinoid-treated cells was mainly due to their stimulatory effect on CMA, because their protective effect was completely abolished in cells unable to carry out CMA (knocked-down for LAMP-2A) (FIG. 7d, bottom). Note that the high sensitivity of CMA-incompetent cells to oxidative stress required use in these cells of one-fourth of the concentration of PQ used in control cells.

Figure 7E:
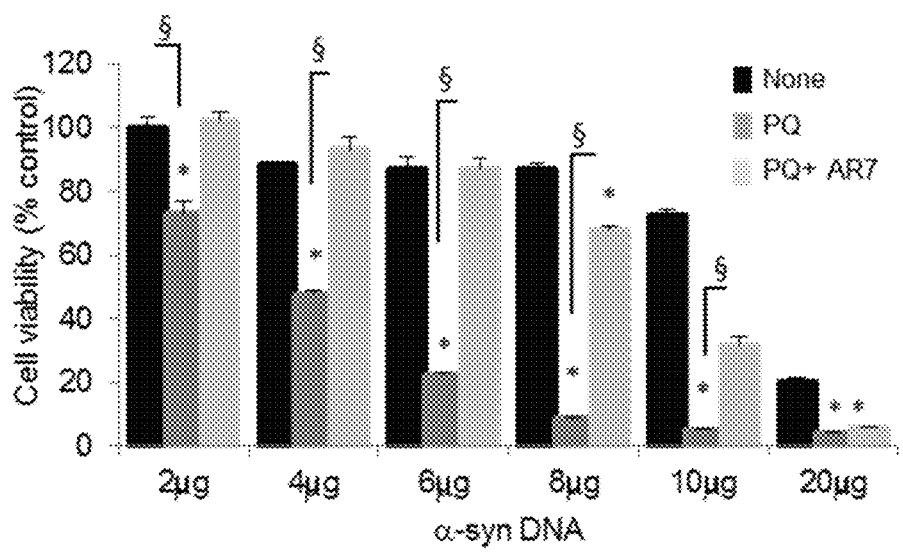
Figure 7F:
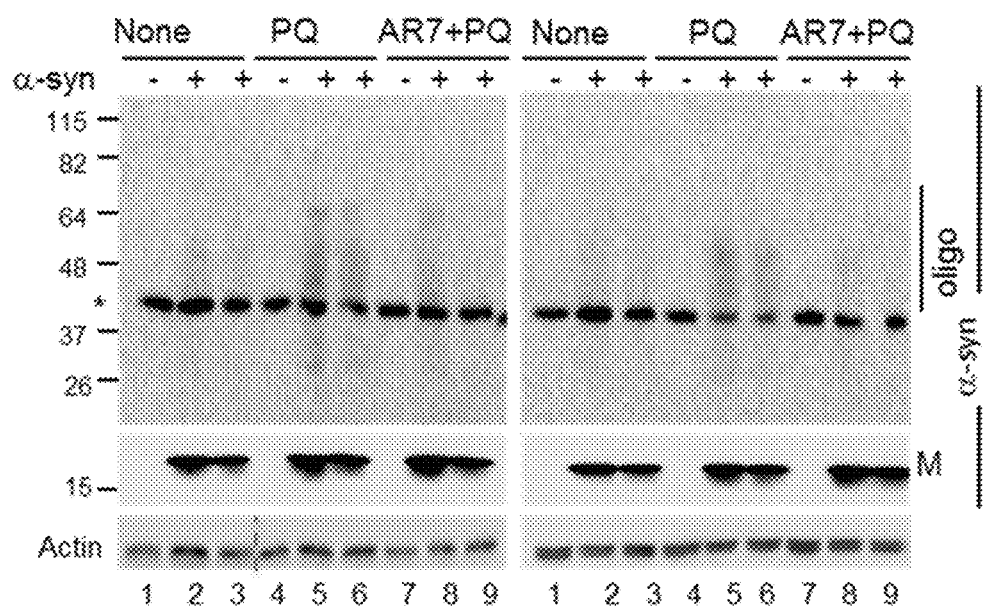

Maintained chronic oxidation is a common feature of aging and an aggravating factor in multiple degenerative disorders. To model the detrimental effect of oxidative stress on proteotoxicity and analyze the possible beneficial effect of enhancing CMA activity in these conditions, cells were transfected with α-synuclein, the protein that accumulates in the form of intracellular aggregates in Parkinson's disease (PD) and previously identified as a bonafide CMA substrate[9,10]. Although mutations in this protein have been associated to the familial forms of the disease, in more than 98% of PD patients the protein that accumulates in the protein inclusions is wild type. Consequently, different intracellular factors and aggressors, including oxidative stress, have been proposed to contribute to the idiopathic forms of this pathology. In the present experimental conditions, transfection of cultured cells with increasing concentrations of cDNA coding for α-synuclein did not result in toxicity until concentrations above 10 μg were used (FIG. 7e). Although the presence of α-synuclein alone was not toxic for these cells, the toxicity of a fixed concentration of PQ was clearly dependent on the concentration of this protein present in the cell. The concentration of PQ added to these cells was adjusted so that in cells expressing low levels of α-synuclein, its toxic effect was limited to no more than 20% reduction in cellular viability. However, the same concentrations of PQ resulted in reductions of up to 80% in cellular viability in cells expressing higher concentrations of α-synuclein (FIG. 7e). The toxic effect in the experimental paradigm resulted from the combination of the oxidative stress and the proteotoxicity associated to α-synuclein, rather than to DNA toxicity, because the effect of PQ remained constant in cells transfected with increasing concentrations of an empty plasmid. Activation of CMA, by pre-treatment of α-synuclein-transfected cells with the novel retinoid derivatives (compound AR7 shown in FIG. 7e) before addition of PQ, resulted in significant increases in cellular viability, even in cells expressing very high levels of α-synuclein. Pre-treatment with the compounds also reduced the formation of oligomeric species of α-synuclein observed in the cells expressing α-synuclein and treated with PQ (FIG. 7f).

These results support the beneficial effect that upregulation of CMA has in the cellular defense against oxidative stress and proteotoxicity and confirm the efficacy of the novel retinoid derivatives to activate CMA even under pathological conditions.

DISCUSSION

The recently gained appreciation for the importance of selective forms of autophagy, such as CMA, in the maintenance of cellular homeostasis and the contribution of their malfunctioning to human disease, has resulted in a growing interest in development of chemical modulators of these pathways. Despite recent findings supporting a direct compromise of CMA in neurodegenerative diseases, diabetes and lysosomal storage disorders[9,11,12], and the pronounced beneficial effect observed when the age-dependent decline of this pathway is prevented[15], chemical modulators of CMA were for the most part lacking until now. One of the main limitations for the development of CMA activators and inhibitors has been the absence of chemical targets for this pathway. Most of the key components for this pathway are multifunctional proteins that participate in many other cellular processes, which would make their chemical targeting for modulation of CMA very nonspecific. LAMP-2A, the most unique component for CMA, is also a difficult target due to its high homology (almost 85% identity) with the other spliced variants of the lamp2 gene, known to participate in other cellular functions such as macroautophagy, lysosomal biogenesis and cholesterol trafficking[36].

The present work identified a novel regulator of CMA activity amenable for chemical targeting. Signaling through the RARα receptor was found to exert an inhibitory effect on CMA. Although complete disruption of signaling through this receptor by knock-down of the receptor protein is effective in attaining maximal CMA activation, this intervention leads to inhibition of macroautophagy. Using structure-based chemical design, it was possible to dissociate the opposite effects of RARα on macroautophagy and CMA and to generate compounds capable of antagonizing only the RARα inhibitory effect on CMA, without affecting macroautophagy. The protective effect of the upregulation of CMA mediated by these compounds against oxidative stress and proteotoxicity were also demonstrated.

Figure 4D:
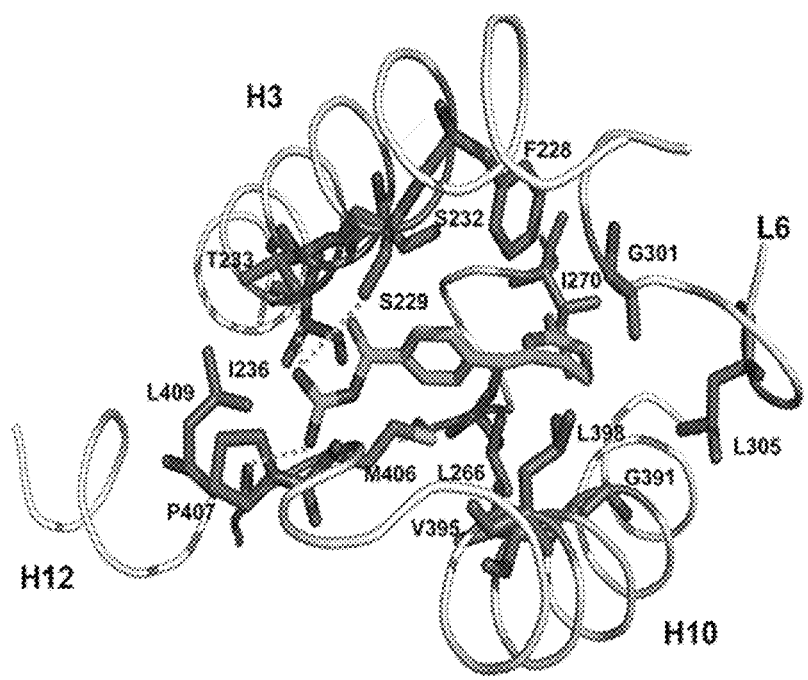

The high antagonistic effect of the novel retinoid derivatives likely results from the combination of tight binding to RARα (favored by the multiplicity of contact sites within the binding pocket) and high stability (obtained by protecting the sites in retinoids usually amenable to intracellular modification). For example, in GR1 and GR2, the polyene linker and the hydrophobic ring are predominantly surrounded by hydrophobic side chains that protect this region, and the interaction with RARα residues Thr233, Ser229 and Pro407 may contribute to the resonance stabilization of the guanidine type polar moiety (FIGS. 4d and 4f). Similarly, in the case of AR7, the bulky aromatic rings offer excellent interaction contacts with the surrounding hydrophobic RARα residues such as Met406, Leu266, Leu398 and Ile270 (FIG. 4c).

Reciprocal cross-talk between macroautophagy and CMA has been previously reported and it is behind the compensatory activation of one of these pathways when the other malfunctions[5]. The present findings support that RARα signaling could be one of the mechanisms that modulate the cross-talk between both autophagic pathways, judging by its opposite effect on them. In practice, implementation of treatments aimed at upregulating CMA by targeting RARα signaling requires dissociating this effect from the one observed on macroautophagy, as otherwise upregulation of CMA will lead to undesired reduction in macroautophagic activity. Both gene activation and gene repression have been described to occur through the complex family of RARs, and examples of redundant and type-specific functions for each of the members of this family have been reported[17]. This functional diversity suggests that the interaction of RAR molecules with their targets is probably modulated by multiple factors, including unique characteristics of the binding of ligands to this receptor. This last property and been exploited to introduce chemical modifications in the ligands to favor the effect of RARα on a particular subset of targets that in turn leads to the selective activation of CMA.

Activation of CMA by the novel retinoid derivatives generated in this study is not reactive to blockage of macroautophagy or to a higher oxidative intracellular environment. Instead, upregulation of CMA occurs selectively, and in contrast to the receptor-independent effects described for ATRA on macroautophagy, it depends on a functional RARα. Evidence is presented that LAMP-2A is one of the downstream targets of this pathway. The fact that the LAMP-2A gene does not contain a recognizable retinoic acid response element region and that the retinoid derivatives suppressed rather than activate a reporter with that sequence, suggest that transcriptional activation of LAMP-2A is under negative control by RARα. It is noteworthy to point out that although most lysosomal proteins are under a common transcriptional program controlled by TFEB[37], LAMP-2A is one of the few exceptions. RARα signaling is thus the first signaling mechanism shown to regulate this lysosomal receptor. Interestingly, ChIP-Seq analysis have revealed that one of the two largest functional classes of RAR target genes was related to proteolysis[38]. The present study contributes to further reinforce the importance of RAR signaling in protein degradation.

The protective effect against oxidation and proteotoxicity observed of the new retinoid derivatives supports the therapeutic potential of these and related compounds in chronic age-related diseases. Maintenance of protein homeostasis is achieved through a tightly coordinated balance between chaperones and proteolytic systems. It is essential thus, to develop interventions that can separately affect one of these processes without compromising the functionality of the other cellular quality control mechanisms. The efficient upregulation of CMA observed with the retinoid derivatives and their lack of noticeable effects on macroautophagy makes them suitable for the selective modulation of CMA in those conditions in which this pathway is primarily compromised such as neurodegeneration and in aging.

TABLE 1

Synthesis and properties of the four groups of retinoid derivatives generated for this study Atypical Retinoids TABLE 1-continued Synthesis and properties of the four groups of retinoid derivatives generated for this study

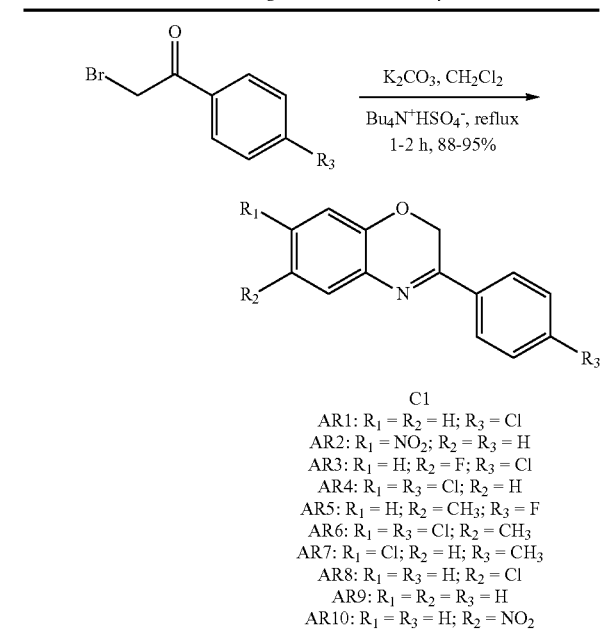

C1
AR1: $R_1 = R_2 = H$; $R_3 = Cl$
AR2: $R_1 = NO_2$; $R_2 = R_3 = H$
AR3: $R_1 = H$; $R_2 = F$; $R_3 = Cl$
AR4: $R_1 = R_3 = Cl$; $R_2 = H$
AR5: $R_1 = H$; $R_2 = CH_3$; $R_3 = F$
AR6: $R_1 = R_3 = Cl$; $R_2 = CH_3$
AR7: $R_1 = Cl$; $R_2 = H$; $R_3 = CH_3$
AR8: $R_1 = R_3 = H$; $R_2 = Cl$
AR9: $R_1 = R_2 = R_3 = H$
AR10: $R_1 = R_3 = H$; $R_2 = NO_2$

NMR (Ref 33)

Guanidine Retinoids

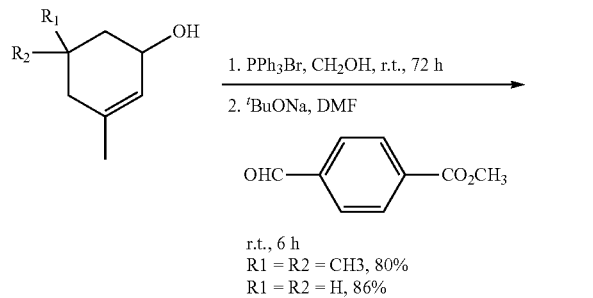

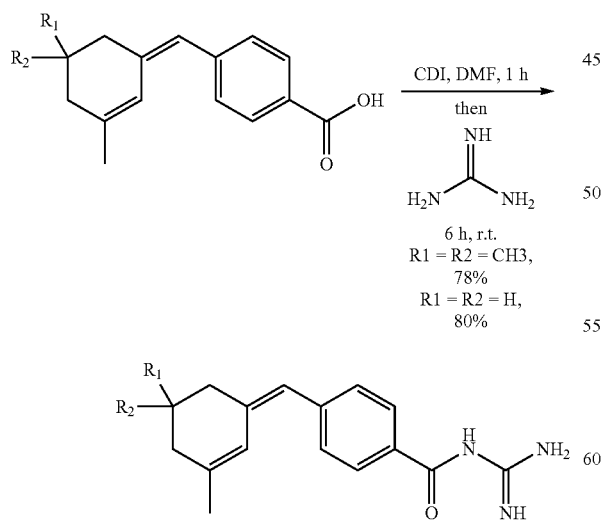

C2 GR1: $R_1 = R_2 = CH_3$
C3 GR2: $R_1 = R_2 = H$

NMR (Ref 32)

α-Aminonitrile Retinoids

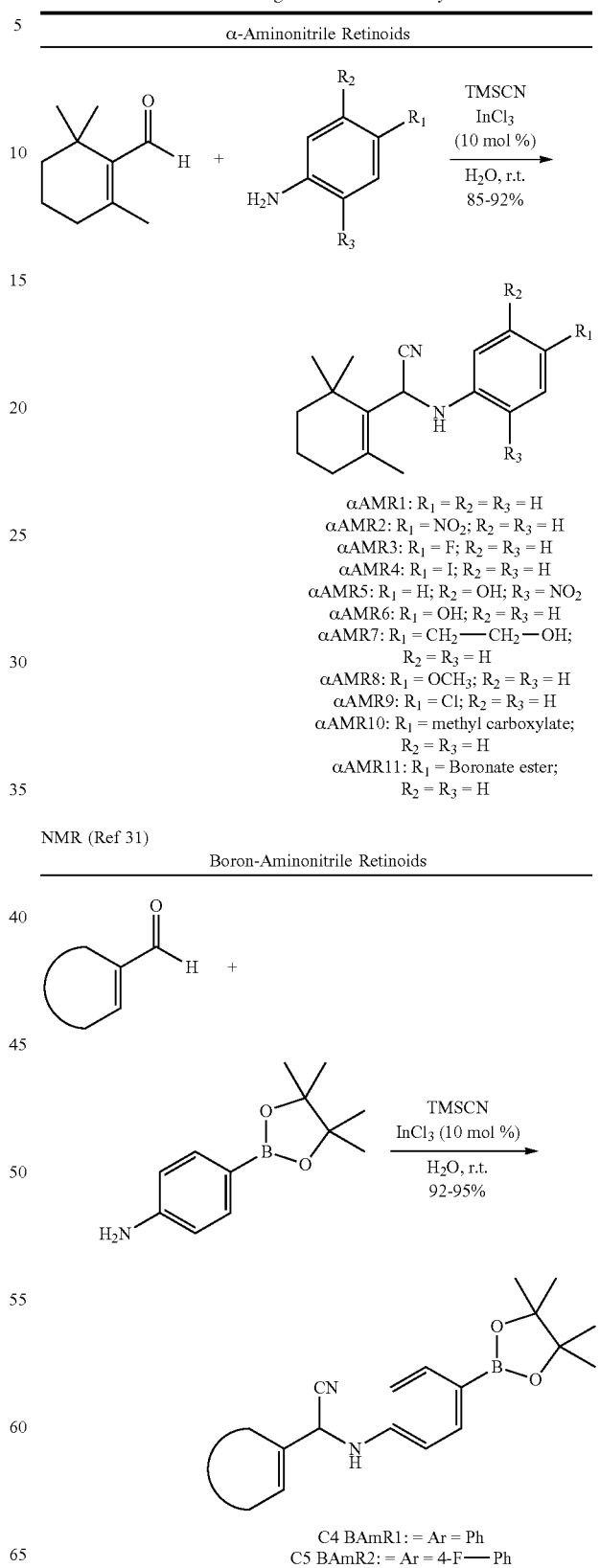

αAMR1: $R_1 = R_2 = R_3 = H$
αAMR2: $R_1 = NO_2$; $R_2 = R_3 = H$
αAMR3: $R_1 = F$; $R_2 = R_3 = H$
αAMR4: $R_1 = I$; $R_2 = R_3 = H$
αAMR5: $R_1 = H$; $R_2 = OH$; $R_3 = NO_2$
αAMR6: $R_1 = OH$; $R_2 = R_3 = H$
αAMR7: $R_1 = CH_2—CH_2—OH$; $R_2 = R_3 = H$
αAMR8: $R_1 = OCH_3$; $R_2 = R_3 = H$
αAMR9: $R_1 = Cl$; $R_2 = R_3 = H$
αAMR10: $R_1 = $ methyl carboxylate; $R_2 = R_3 = H$
αAMR11: $R_1 = $ Boronate ester; $R_2 = R_3 = H$ NMR (Ref 31)

Boron-Aminonitrile Retinoids

C4 BAmR1: = Ar = Ph
C5 BAmR2: = Ar = 4-F—Ph

TABLE 1-continued

Synthesis and properties of the four groups of retinoid derivatives generated for this study

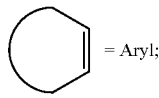 = Aryl;

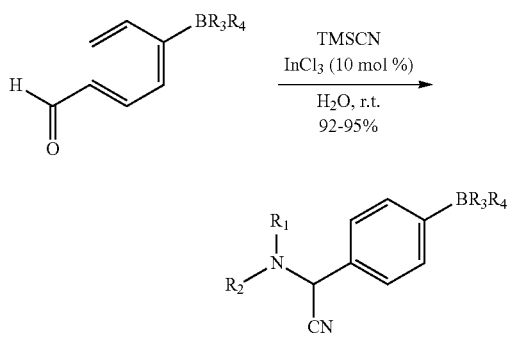

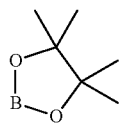

Boronate ester

Example B

Overview

Chaperone-mediated autophagy (CMA) contributes to cellular quality control and the cellular response to stress through the selective degradation of cytosolic proteins in lysosomes. Pathogenic proteins of common neurodegenerative disorders such as Parkinson's and Huntington's disease or frontotemporal dementia have been shown to undergo degradation via CMA. A decrease in CMA occurs in aging and therefore may contribute to accelerate the course of age related disorders. There are very limited options for the chemical modulation of CMA. CMA is inhibited by signaling from the nuclear retinoic acid receptor α (RARα). In Example A, RARα antagonists (AR7, GR1 and GR2) were described that can selectively activate CMA without affecting other cellular clearance pathways. A structure-based drug design and medicinal chemistry, based on the AR7 scaffold, have now been applied to increase the CMA activation potency. Using a photoactivatable fluorescent CMA reporter, the CMA activation potency of these new compounds was determined in cultured cells. Compared with AR7, most of the new compounds showed similar to better activity. Compound QX39 showed 2-3 fold higher potency than AR7, and in contrast to the parent molecule that only activated basal CMA. Several compounds including compound QX39 activated both basal and stress-induced CMA. The effect of these compounds in protein degradation has been demonstrated using metabolic labeling in cultured cells. Several of the new compounds demonstrated better stimulatory effect on lysosomal degradation and protective effect on cell viability upon induction of oxidative stress, proteotoxicity and lipotoxicity in mouse embryo fibriblasts or neuronal cell lines.

Design and Synthesis of Example Compounds

Example 1

3-([1,1'-biphenyl]-4-yl)-7-chloro-2H-benzo[b][1,4]oxazine (A-1)

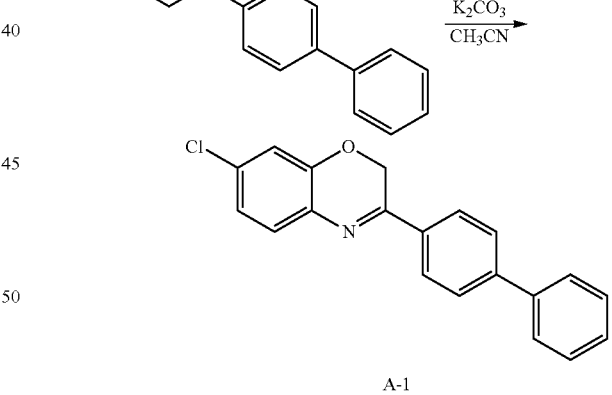

A-1

To 2-amino-5-chlorophenol (143.6 mg, 1 mmol) in acetonitrile (10 mL) was added $K_2CO_3$ (0.27 g, 2 mmol). Into this, 1-([1,1'-biphenyl]-4-yl)-2-bromoethan-1-one (280 mg, 1.1 mmol) in acetonitrile (15 mL) was added dropwise at room temperature. The reaction was then stirred overnight under reflux. Then the solvent was evaporated and the residue was dissolved in dichloromethane (20 mL). The organic layer was washed with water, brine and dried over $Na_2SO_4$. The desired compound was isolated through silica gel chromatography. Recrystallization with hot ethanol gave a light yellow powder (A-1, 80 mg, 25%). MS (ESI) M+H$^+$=320.09.

Example 2

3-([1,1'-biphenyl]-4-yl)-7-methyl-2H-benzo[b][1,4]oxazine (A-2)

(QX43)

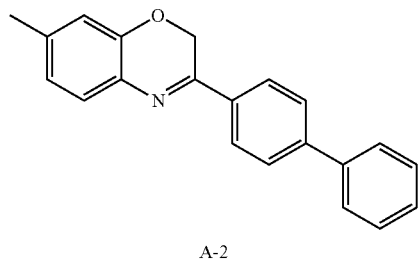

A-2

To 2-amino-5-methylphenol (123.2 mg, 1 mmol) in dichloromethane (10 mL) was added K₂CO₃ (0.27 g, 2 mmol), tetrabutylammonium bisulfate (17 mg, 0.05 mmol). Into this, 1-([1,1'-biphenyl]-4-yl)-2-bromoethan-1-one (280 mg, 1.1 mmol) in dichloromethane (15 mL) was added dropwise at room temperature. The reaction was then stirred overnight under reflux. The reaction was washed with water, brine and dried over Na₂SO₄. The desired compound was isolated through silica gel chromatography. Recrystallization with hot ethanol gave a light yellow powder (A-2, 57 mg, 19%). MS (ESI) M+H⁺=300.13.

Example 3

3-([1,1'-biphenyl]-4-yl)-7-(trifluoromethyl)-2H-benzo[b][1,4]oxazine (A-3)

(QX69)

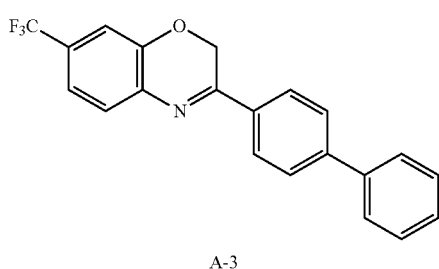

A-3

Following a procedure analogous to the procedure described in example 2 using 2-amino-5-(trifluoromethyl)phenol (97.4 mg, 0.55 mmol) and 1-([1,1'-biphenyl]-4-yl)-2-bromoethan-1-one (137.5 mg, 0.5 mmol). The desired compound was obtained as white solid (A-3, 41.5 mg, 24.5%). MS (ESI) M+H⁺=354.24.

Example 4

3-([1,1'-biphenyl]-4-yl)-7-(trifluoromethyl)-2H-benzo[b][1,4]oxazine (A-4)

(QX70)

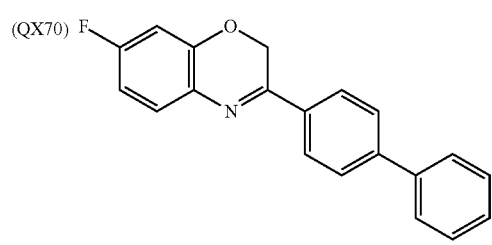

A-4

Following a procedure analogous to the procedure described in example 2 using 2-amino-5-fluorophenol (69.9 mg, 0.55 mmol) and 1-([1,1'-biphenyl]-4-yl)-2-bromoethan-1-one (137.5 mg, 0.5 mmol). The desired compound was obtained as white solid (A-4, 39 mg, 25.7%). MS (ESI) M+H⁺=304.16.

Example 5

7-chloro-3-(4-(pyridin-4-yl)phenyl)-2H-benzo[b][1,4]oxazine (A-5): (QX 136)

Step 1

3-(4-bromophenyl)-7-chloro-2H-benzo[b][1,4]oxazine (intermediate 1)

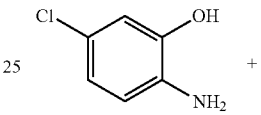

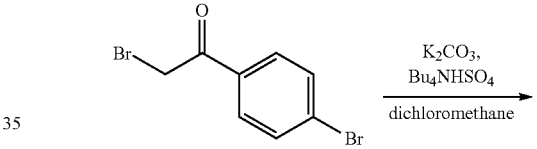

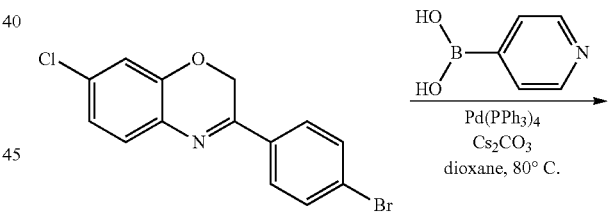

intermediate 1

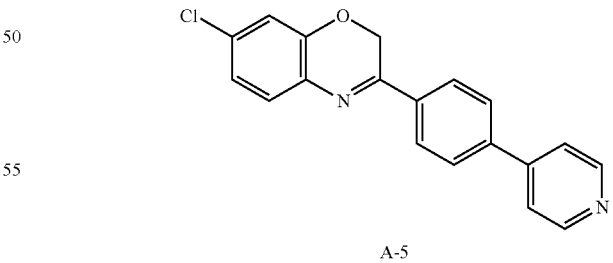

A-5

Following a procedure analogous to the procedure described in example 2 using 2-amino-5-chlorophenol (287.14 mg, 2 mmol) and 2-bromo-1-(4-bromophenyl)ethan-1-one (555.9 mg, 2 mmol). The desired compound was obtained as white solid (intermediate 1, 333 mg, 51.6%). MS (ESI) M+H⁺=322.95.

Step 2: 7-chloro-3-(4-(pyridin-4-yl)phenyl)-2H-benzo[b][1,4]oxazine (A-5): A nitrogen flushed vessel was filled with 3-(4-bromophenyl)-7-chloro-2H-benzo[b][1,4]oxazine (intermediate 1, 50 mg, 0.15 mmol), pyridin-4-ylboronic acid (22.7 mg, 0.185 mmol) and $Cs_2CO_3$ (97.7 mg, 0.3 mmol, 2N in water). The vessel was flushed with nitrogen for a second time and Tetrakis(triphenylphosphine)palladium(0) (17.3 mg, 0.015 mmol) was added. Then solvent dioxane (15 mL) was added and the reaction was degassed and protected with nitrogen, and stirred at 80° C. overnight. Then the solvent was evaporated and the residue was dissolved in dichloromethane (25 mL). The organic layer was washed with water, brine and dried over $Na_2SO_4$. The desired compound was isolated through silica gel chromatography. Recrystallization with hot ethanol gave a light yellow powder (A-5, 43 mg, 89%). MS (ESI) M+H$^+$=320.07.

Example 6

7-chloro-3-(4-(isoquinolin-4-yl)phenyl)-2H-benzo[b][1,4]oxazine (A-6)

(QX138)

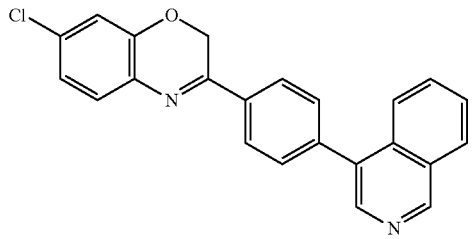

A-6

Following a procedure analogous to the procedure described in step 2 of example 5, using 3-(4-bromophenyl)-7-chloro-2H-benzo[b][1,4]oxazine (intermediate 1, 100 mg, 0.3 mmol) and isoquinolin-4-ylboronic acid (62.3 mg, 0.36 mmol). The desired compound was obtained as off-white powder (A-6, 81.3 mg, 73.1%). MS (ESI) M+H$^+$=371.13.

Example 7

1-(3-(4-(7-chloro-2H-benzo[b][1,4]oxazin-3-yl)phenyl)thiophen-2-yl)ethan-1-one (A-7)

(QX139)

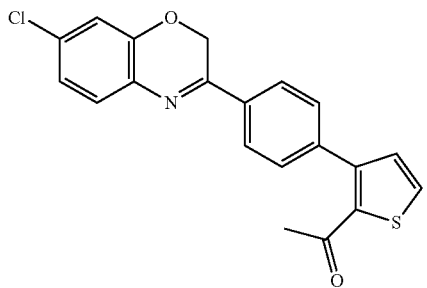

A-7

Following a procedure analogous to the procedure described in step 2 of example 5, using 3-(4-bromophenyl)-7-chloro-2H-benzo[b][1,4]oxazine (intermediate 1, 100 mg, 0.3 mmol) and (2-acetylthiophen-3-yl)boronic acid (61.2 mg, 0.36 mmol). The desired compound was obtained as off-white powder (A-7, 68.2 mg, 61.8%). MS (ESI) M+H$^+$=368.43.

Example 8 methyl 4'-(7-chloro-2H-benzo[b][1,4]oxazin-3-yl)-6-methyl-[1,1'-biphenyl]-3-carboxylate (A-8)

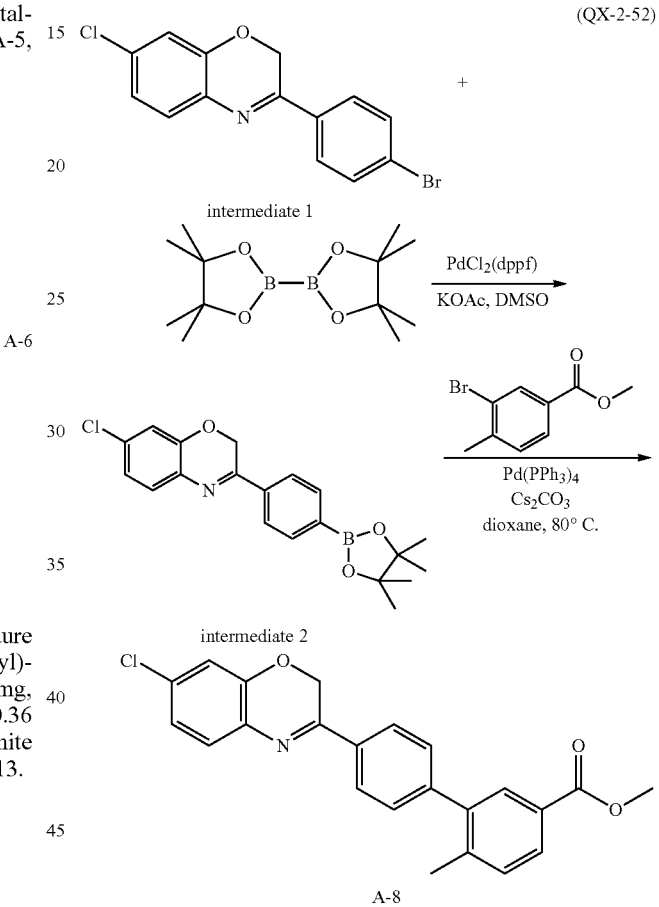

Step 1: 7-chloro-3-(4-(4,4,5,5-tetramethyl-1,3,2-dioxaborolan-2-yl)phenyl)-2H-benzo[b][1,4]oxazine (intermediate 2): A nitrogen flushed vessel was filled with 3-(4-bromophenyl)-7-chloro-2H-benzo[b][1,4]oxazine (intermediate 1, 800 mg, 2.48 mmol), 4,4,4',4',5,5,5',5'-octamethyl-2,2'-bi(1,3,2-dioxaborolane) (756 mg, 2.98 mmol) and potassium acetate (730.2 mg, 7.44 mmol). The vessel was flushed with nitrogen for second time and [1,1'-Bis(diphenylphosphino)ferrocene]dichloropalladium(II) (204.16 mg, 0.25 mmol) was added. Then solvent dimethyl sulfoxide (50 mL) was added and the reaction was degassed and protected with nitrogen, and stirred at 80° C. for 2 hours. Then the reaction solution was filtered and the filtrate was diluted with acetate ester (200 mL). The organic layer was washed with water, brine and dried over $Na_2SO_4$. The desired compound was isolated through silica gel chromatography to give a pink powder (intermediate 2, 500 mg, 54.5%). MS (ESI) M+H$^+$=370.14.

Step 2: methyl 4'-(7-chloro-2H-benzo[b][1,4]oxazin-3-yl)-6-methyl-[1,1'-biphenyl]-3-carboxylate (A-8): Following a procedure analogous to the procedure described in step 2 of example 5, using 7-chloro-3-(4-(4,4,5,5-tetramethyl-1,3,2-dioxaborolan-2-yl)phenyl)-2H-benzo[b][1,4]oxazine (intermediate 2, 120 mg, 0.32 mmol) and methyl 3-bromo-4-methylbenzoate (89.2 mg, 0.39 mmol). The desired compound was obtained as white powder (A-8, 104 mg, 82.9%). MS (ESI) M+H$^+$=392.30.

Example 9

7-chloro-3-(4'-chloro-[1,1'-biphenyl]-4-yl)-2H-benzo[b][1,4]oxazine (A-9)

(QX-2-85)

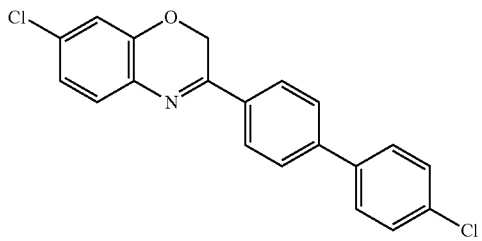

Following a procedure analogous to the procedure described in step 2 of example 5, using 3-(4-bromophenyl)-7-chloro-2H-benzo[b][1,4]oxazine (intermediate 1, 100 mg, 0.3 mmol) and (4-chlorophenyl)boronic acid (56.3 mg, 0.36 mmol) in water/ethanol/toluene (1.5/2.5/10, 14 mL). The desired compound was obtained as white powder (A-9, 30 mg, 28.2%). MS (ESI) M+H$^+$=354.04.

Example 10

4-(7-chloro-2H-benzo[b][1,4]oxazin-3-yl)benzonitrile (A-10)

(QX37)

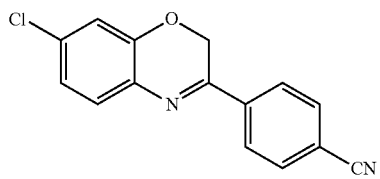

Following a procedure analogous to the procedure described in example 2, using 2-amino-5-chlorophenol (143.6 mg, 1 mmol) and 4-(2-bromoacetyl)benzonitrile (246.5 mg, 1.1 mmol). The desired compound was obtained as white powder (A-10, 42 mg, 16%). MS (ESI) M+H$^+$=269.31.

Example 11

4-(7-methyl-2H-benzo[b][1,4]oxazin-3-yl)benzonitrile (A-11)

(QX41)

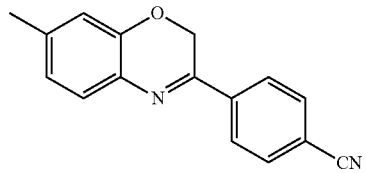

Following a procedure analogous to the procedure described in example 2, using 2-amino-5-methylphenol (123.2 mg, 1 mmol) and 4-(2-bromoacetyl)benzonitrile (246.5 mg, 1.1 mmol). The desired compound was obtained as yellow crystal (A-11, 108 mg, 43.5%). MS (ESI) M+H$^+$=249.14.

Example 12

4-(7-fluoro-2H-benzo[b][1,4]oxazin-3-yl)benzonitrile (A-12)

(QX73)

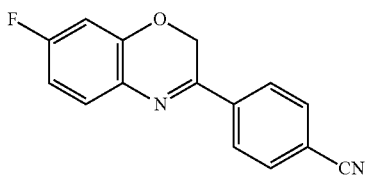

Following a procedure analogous to the procedure described in example 2, using 2-amino-5-fluorophenol (168 mg, 0.75 mmol) and 4-(2-bromoacetyl)benzonitrile (104.9 mg, 0.825 mmol). The desired compound was obtained (A-12, 81 mg, 42.8%). MS (ESI) M+H$^+$=253.06.

Example 13

4-(7-(trifluoromethyl)-2H-benzo[b][1,4]oxazin-3-yl)benzonitrile (A-13)

(QX71)

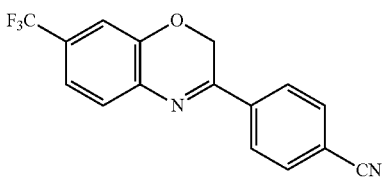

Following a procedure analogous to the procedure described in example 2, using 2-amino-5-(trifluoromethyl)phenol (97.4 mg, 0.55 mmol) and 1-([1,1'-biphenyl]-4-yl)-

2-bromoethan-1-one (137.5 mg, 0.5 mmol). The desired compound was obtained as white solid (A-13, 128 mg, 56.5%). MS (ESI) M+H⁺=303.09.

Example 14

7-methyl-3-(4-(trifluoromethyl)phenyl)-2H-benzo[b][1,4]oxazine (A-14)

(QX48)

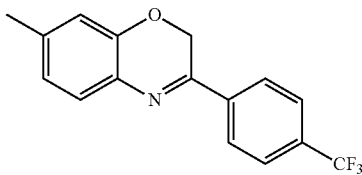

A-14

Following a procedure analogous to the procedure described in example 2, using 2-amino-5-methylphenol (123.2 mg, 1 mmol) and 2-bromo-1-(4-(trifluoromethyl)phenyl)ethan-1-one (320.5 mg, 1.2 mmol). The desired compound was obtained as flake solid (A-14, 136 mg, 46.6%). MS (ESI) M+H⁺=292.08.

Example 15

7-chloro-3-(4-(trifluoromethyl)phenyl)-2H-benzo[b][1,4]oxazine (A-15)

(QX61)

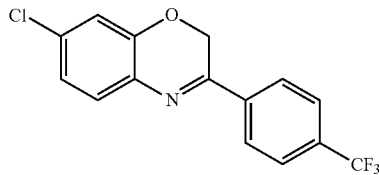

A-15

Following a procedure analogous to the procedure described in example 2, using 2-amino-5-chlorophenol (143.6 mg, 1 mmol) and 2-bromo-1-(4-(trifluoromethyl)phenyl)ethan-1-one (293.7 mg, 1.1 mmol). The desired compound was obtained as flake solid (A-15, 103 mg, 48.6%). MS (ESI) M+H⁺=312.23.

Example 16

7-methyl-3-(4-(trifluoromethoxy)phenyl)-2H-benzo[b][1,4]oxazine (A-16)

(QX49)

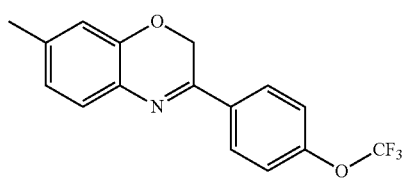

A-16

Following a procedure analogous to the procedure described in example 2, using 2-amino-5-methylphenol (61.6 mg, 0.5 mmol) and 2-bromo-1-(4-(trifluoromethoxy)phenyl)ethan-1-one (155.6 mg, 0.6 mmol). The desired compound was obtained as flake solid (A-16, 40 mg, 26.1%). MS (ESI) M+H⁺=308.08.

Example 17 methyl 4-(7-methyl-2H-benzo[b][1,4]oxazin-3-yl)benzoate (A-17)

(QX59)

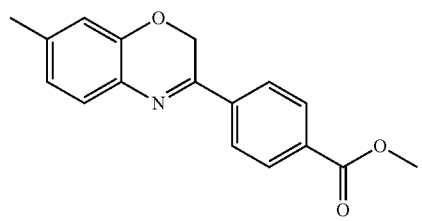

A-17

Following a procedure analogous to the procedure described in example 2, using 2-amino-5-methylphenol (47 mg, 0.38 mmol) and methyl 4-(2-bromoacetyl)benzoate (108 mg, 0.42 mmol). The desired compound was obtained as flake solid (A-17, 74.1 mg, 69%). MS (ESI) M+H⁺= 282.23.

Example 18

4-(7-methyl-2H-benzo[b][1,4]oxazin-3-yl)benzoic acid (A-18)

(QX81)

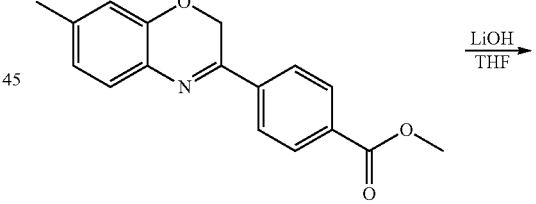

A-17

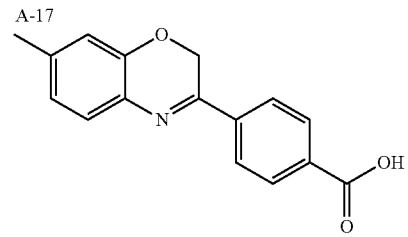

A-18

A-17 (35 mg, 0.124 mmol) was dissolved in THF (4 mL). 1 M LiOH (1.24 mmol, 1.24 mL) was added and the resulting mixture was stirred at room temperature overnight. Then dichloromethane (15 mL) was added to the reaction. 1N HCl (5 mL) was added and stirred for 5 minutes. The organic layer was washed with brine and dried over Na₂SO₄.

The desired compound was isolated through silica gel chromatography to afford yellow powder (A-18, 23 mg, 69%). MS (ESI) (M−H)⁻=266.46.

Example 19 methyl 4-(7-chloro-2H-benzo[b][1,4]oxazin-3-yl)benzoate (A-19)

(QX67)

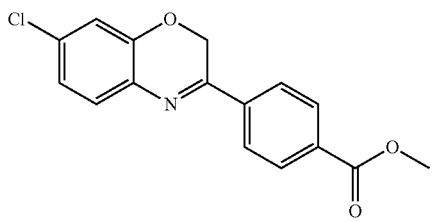

Following a procedure analogous to the procedure described in example 2, using 2-amino-5-chlorophenol (25.8 mg, 0.18 mmol) and methyl 4-(2-bromoacetyl)benzoate (41.1 mg, 0.16 mmol). The desired compound was obtained as white solid (A-19, 31 mg, 64.2%). MS (ESI) M+H⁺= 302.57.

Example 20

N-(4-(7-methyl-2H-benzo[b][1,4]oxazin-3-yl)phenyl)acetamide (A-20)

(QX51)

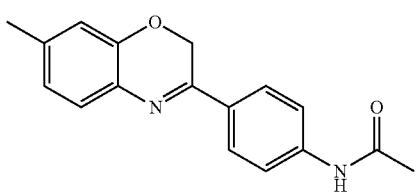

Following a procedure analogous to the procedure described in example 1, using 2-amino-5-methylphenol (61.58 mg, 0.5 mmol) and N-(4-(2-bromoacetyl)phenyl)acetamide (154 mg, 0.6 mmol). The desired compound was obtained as white solid (A-20, 33 mg, 24%). MS (ESI) M+H⁺=281.24.

Example 21

N-(4-(7-chloro-2H-benzo[b][1,4]oxazin-3-yl)phenyl)acetamide (A-21)

(QX77)

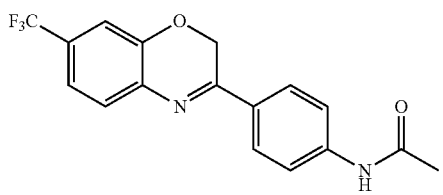

Following a procedure analogous to the procedure described in example 1, using 2-amino-5-chlorophenol (71.7 mg, 0.5 mmol) and N-(4-(2-bromoacetyl)phenyl)acetamide (154 mg, 0.6 mmol). The desired compound was obtained as white solid (A-21, 46 mg, 30.6%). MS (ESI) M+H⁺=301.57.

Example 22

N-(4-(7-methyl-2H-benzo[b][1,4]oxazin-3-yl)phenyl)acetamide (A-22)

(QX79)

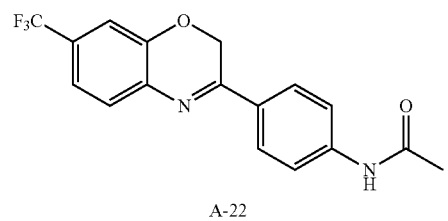

Following a procedure analogous to the procedure described in example 1, using 2-amino-5-(trifluoromethyl)phenol (88.6 mg, 0.55 mmol) and N-(4-(2-bromoacetyl)phenyl)acetamide (154 mg, 0.6 mmol). The desired compound was obtained as white solid (A-22, 75.5 mg, 22.6%). MS (ESI) M+H⁺=335.38.

Example 23

4-(7-chloro-2H-benzo[b][1,4]oxazin-3-yl)benzoic acid (A-23): (QX90)

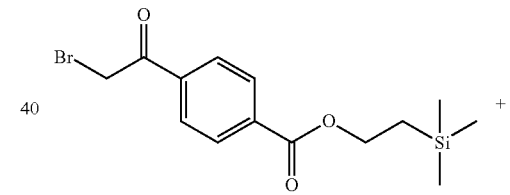

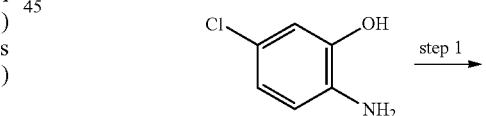

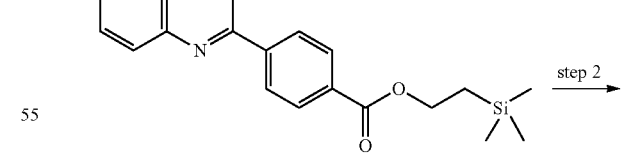

intermediate 3

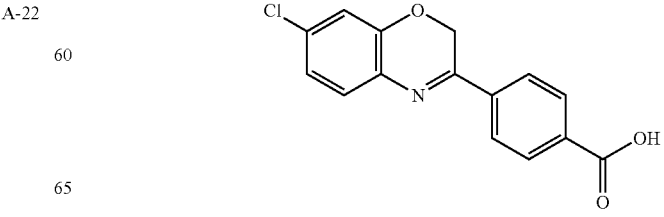

Step 1: 2-(trimethylsilyl)ethyl 4-(7-chloro-2H-benzo[b][1,4]oxazin-3-yl)benzoate (intermediate 3): Following a procedure analogous to the procedure described in example 2, using 2-amino-5-chlorophenol (71.8 mg, 0.5 mmol) and 2-(trimethylsilyl)ethyl 4-(2-bromoacetyl)benzoate (WO 2009112615) (188 mg, 0.55 mmol). The desired compound was obtained as white powder (intermediate 3, 130 mg, 67%). MS (ESI) M+H$^+$=388.78.

Step 2: 4-(7-chloro-2H-benzo[b][1,4]oxazin-3-yl)benzoic acid (A-23): To a solution of 2-(trimethylsilyl)ethyl 4-(7-chloro-2H-benzo[b][1,4]oxazin-3-yl)benzoate (intermediate 3, 100 mg, 0.26 mmol) in THF (20 mL), Tetrabutylammonium fluoride hydrate (TBAF, 202 mg, 0.77 mmol) was added. The resulting solution was stirred for 1 hour at room temperature. Then the solvent was evaporated and the residue was dissolved in dichloromethane (30 mL). 1N HCl (5 mL) was added and stirred. Then the organic layer was washed with water, brine and dried over Na$_2$SO$_4$. The desired compound was isolated through silica gel chromatography. Recrystallization with hot ethanol/hexanes gave a solid (A-23, 43 mg, 40.4%). MS (ESI) (M−H)$^−$=286.67.

Example 24

4-(7-fluoro-2H-benzo[b][1,4]oxazin-3-yl)benzoic acid (A-24)

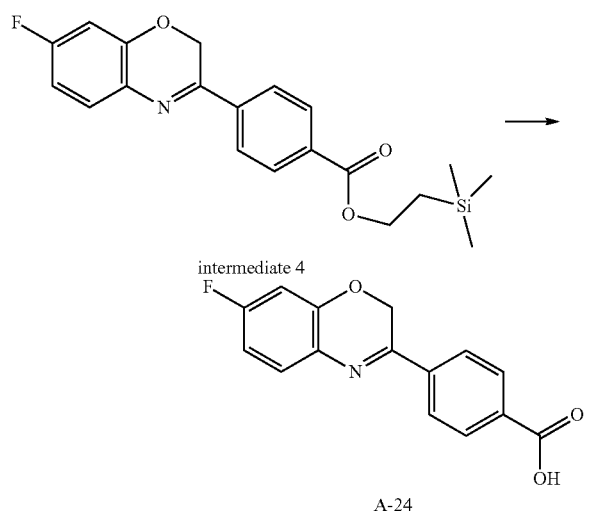

Step 1. 2-(trimethylsilyl)ethyl 4-(7-fluoro-2H-benzo[b][1,4]oxazin-3-yl)benzoate (intermediate 4): Following a procedure analogous to the procedure described in example 2, using 2-amino-5-fluorophenol (63.5 mg, 0.5 mmol) and 2-(trimethylsilyl)ethyl 4-(2-bromoacetyl)benzoate (WO 2009112615) (171.6 mg, 0.5 mmol). The desired compound was obtained as white powder (intermediate 4, 112 mg, 60.3%). MS (ESI) M+H$^+$=372.40.

Step 2: 3-(7-fluoro-2H-benzo[b][1,4]oxazin-3-yl)benzoic acid (A-24): Following a procedure analogous to the procedure described in step 2 of example 23, the desired compound was obtained as white powder (A-24, 32 mg, 35.7%). MS (ESI) (M−H)$^−$=270.05.

Example 25

3-(7-fluoro-2H-benzo[b][1,4]oxazin-3-yl)benzoic acid (A-25)

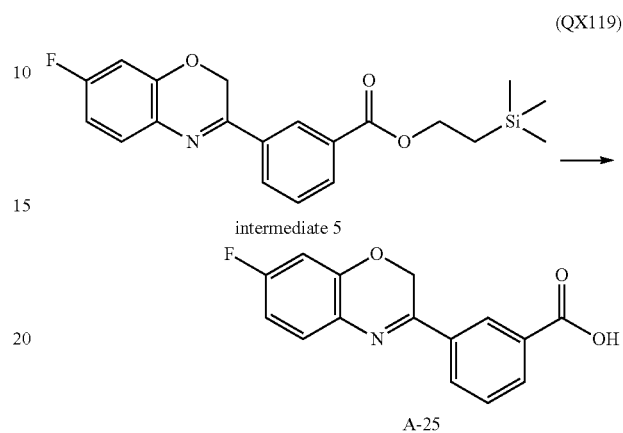

Step 1: 2-(trimethylsilyl)ethyl 3-(7-fluoro-2H-benzo[b][1,4]oxazin-3-yl)benzoate (intermediate 5): Following a procedure analogous to the procedure described in example 2, using 2-amino-5-fluorophenol (91.5 mg, 0.7 mmol) and 2-(trimethylsilyl)ethyl 3-(2-bromoacetyl)benzoate (247 mg, 0.7 mmol). The desired compound was obtained as white powder (intermediate 5, 135 mg, 47.4%). MS (ESI) M+H$^+$=372.40.

Step 2: 3-(7-fluoro-2H-benzo[b][1,4]oxazin-3-yl)benzoic acid (A-25): Following a procedure analogous to the procedure described in step 2 of example 23, the desired compound was obtained as white powder (A-25, 32 mg, 35.7%). MS (ESI) (M−H)$^−$=270.06.

Example 26

4-(7-chloro-2H-benzo[b][1,4]oxazin-3-yl)benzoic acid (A-26)

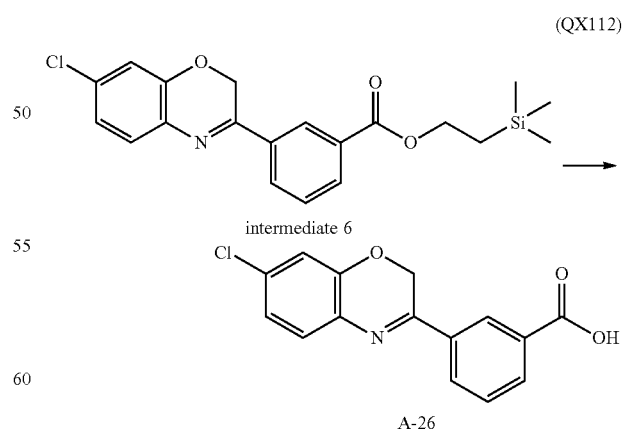

Step 1: 2-(trimethylsilyl)ethyl 3-(7-chloro-2H-benzo[b][1,4]oxazin-3-yl)benzoate (intermediate 6): Following a procedure analogous to the procedure described in example 2, using 2-amino-5-chlorophenol (71.5 mg, 0.5 mmol) and 2-(trimethylsilyl)ethyl 3-(2-bromoacetyl)benzoate (171.6 mg, 0.5 mmol). The desired compound was obtained as pink powder (intermediate 6, 172 mg, 88.6%). MS (ESI) M+H$^+$=388.76.

Step 2: 3-(7-chloro-2H-benzo[b][1,4]oxazin-3-yl)benzoic acid (A-26): Following a procedure analogous to the procedure described in step 2 of example 23, the desired compound was obtained as white powder (A-26, 58 mg, 45.8%). MS (ESI) M+H$^+$=288.29.

Example 27

3-(4-(6-chloro-2H-benzo[b][1,4]oxazin-3-yl)phenyl)prop-2-yn-1-ol (A-27)

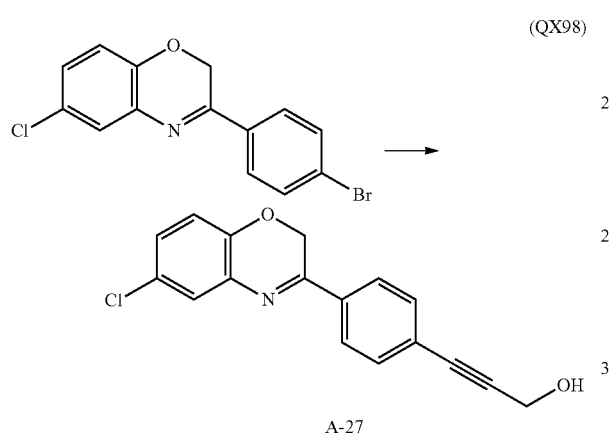

A-27

A nitrogen flushed vessel was filled with 3-(4-bromophenyl)-6-chloro-2H-benzo[b][1,4]oxazine (Nat. Chem. Bio, 2013, 9, 374-382, 70 mg, 0.22 mmol) and prop-2-yn-1-ol (37 uL, 0.65 mmol) in the solvent triethylamine (3 mL)/dioxane (anhydrous, 3 mL). The vessel was flushed with nitrogen for a second time. Bis(triphenylphosphine)palladium(II) dichloride (7 mg, 0.01 mmol) and CuI (1.9 mg, 0.01 mmol) were added and the reaction was degassed, protected with nitrogen and stirred at 70° C. overnight. Then the reaction was diluted with dichloromethane (25 mL). The organic layer was washed with water, brine and dried over Na$_2$SO$_4$. The desired compound was isolated through silica gel chromatography to give a solid (A-27, 39 mg, 60.4%). MS (ESI) M+H$^+$=298.07.

Example 28

3-(4-(7-chloro-2H-benzo[b][1,4]oxazin-3-yl)phenyl)prop-2-yn-1-ol (A-28)

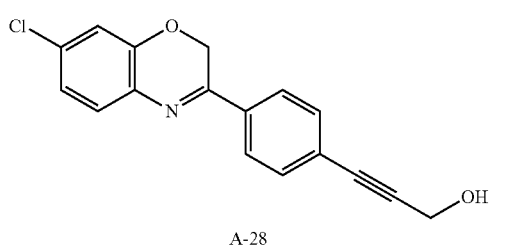

A-28

Following a procedure analogous to the procedure described in example 27, using 3-(4-bromophenyl)-7-chloro-2H-benzo[b][1,4]oxazine (intermediate 1, 120 mg, 0.37 mmol) and prop-2-yn-1-ol (32.5 uL, 0.65 mmol). The desired compound was obtained (A-28, 53 mg, 48.1%). MS (ESI) M+H$^+$=298.07.

Example 29

3-(4-(7-fluoro-2H-benzo[b][1,4]oxazin-3-yl)phenyl)prop-2-yn-1-ol (A-29): (QX134)

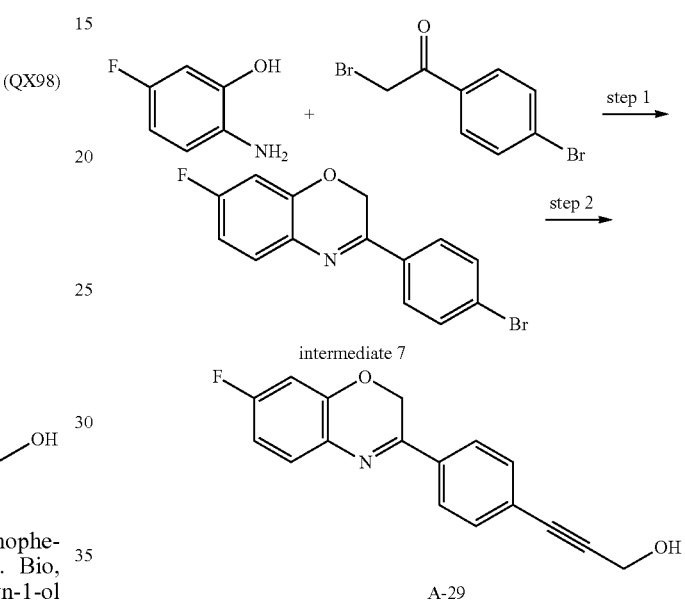

A-29

Step 1: 3-(4-bromophenyl)-7-fluoro-2H-benzo[b][1,4]oxazine (intermediate 7):): Following a procedure analogous to the procedure described in example 2, using 2-amino-5-fluorophenol (254.2 mg, 2 mmol) and 2-bromo-1-(4-bromophenyl)ethan-1-one (555.9 mg, 2 mmol). The desired compound was obtained as white solid (intermediate 1, 367.4 mg, 60%). MS (ESI) M+H$^+$=307.65.

Step 2: Following a procedure analogous to the procedure described in example 27, using 3-(4-bromophenyl)-7-fluoro-2H-benzo[b][1,4]oxazine (intermediate 7, 113.2 mg, 0.37 mmol) and prop-2-yn-1-ol (65 uL, 1.11 mmol). The desired compound was obtained (A-29, 48 mg, 46.1%). MS (ESI) M+H$^+$=282.01.

High Content Microscopy Assay

CMA activity in mouse fibroblasts in culture was measured using a new version of a previously developed photoswitchable (PS) CMA fluorescent reporter[30] generated by addition of a CMA targeting motif to the PS-dendra protein (KFERQ-PS-dendra). Briefly, cells transduced with lentivirus carrying the reporter were photoactivated 24 h after transduction by exposure to a 3.5 mA (current constant), and 90V light emitting diode (LED: Norlux, 405 nm) for 9 min. Cells were plated in 96 well plates, subjected to the desired treatments and at the end of the experiment fixed in 4% paraformaldehyde. Images were captured with a high content microscope (Opperetta system, Perkin Elmer) and quantification was performed with the instrument software in a minimum of 200 cells or 9 fields.

Cell Viability

Cells were plated in 96-well flat bottom plates (BD biosystems), in 100 μl volume of media, and after the indicated treatments, cell viability was measured using the CellTiterBlue® cell viability assay reagent (Promega) as changes in the fluorescence (excitation 540 nm, emission 590 nm) according to the manufacturer's instructions. Fluorescence intensity values were normalized to values of untreated wells. Treatment with paraquat or oleic-acid at the indicated concentrations were performed by directly adding the agents to the culture media 12 h after addition of the QX compounds or simultaneously added with the compounds. Viability was measured at 24 h after addition of the stressors.

Results

Examples of results are described in FIGS. 9-16.

REFERENCES

1. Mizushima, N., Levine, B., Cuervo, A. M. & Klionsky, D. J. Autophagy fights disease through cellular self-digestion. *Nature* 451, 1069-75 (2008).
2. Yang, Z. & Klionsky, D. J. An overview of the molecular mechanism of autophagy. *Curr Top Microbiol Immunol* 335, 1-32 (2009).
3. Mizushima, N. Autophagy in Protein and Organelle Turnover. *Cold Spring Harb Symp Quant Biol* (2011).
4. Wong, E. & Cuervo, A. M. Autophagy gone awry in neurodegenerative diseases. *Nature Neuroscience* 13, 805-811 (2010).
5. Arias, E. & Cuervo, A. M. Chaperone-mediated autophagy in protein quality control. *Curr Opin Cell Biol* 23, 184-9 (2010).
6. Dice, J. F. Peptide sequences that target cytosolic proteins for lysosomal proteolysis. *Trends Biochem Sci* 15, 305-309 (1990).
7. Chiang, H., Terlecky, S., Plant, C. & Dice, J. F. A role for a 70-kilodalton heat shock protein in lysosomal degradation of intracellular proteins. *Science* 246, 382-385 (1989).
8. Bandyopadhyay, U., Kaushik, S., Varticovski, L. & Cuervo, A. M. The chaperone-mediated autophagy receptor organizes in dynamic protein complexes at the lysosomal membrane. *Mol Cell Biol* 28, 5747-63 (2008).
9. Cuervo, A. M., Stefanis, L., Fredenburg, R., Lansbury, P. T. & Sulzer, D. Impaired degradation of mutant alpha-synuclein by chaperone-mediated autophagy. *Science* 305, 1292-5 (2004).
10. Mak, S. K., McCormack, A. L., Manning-Bog, A. B., Cuervo, A. M. & Di Monte, D. A. Lysosomal degradation of alpha-synuclein in vivo. *J Biol Chem* 285, 13621-9 (2010).
11. Wang, Y. et al. Tau fragmentation, aggregation and clearance: the dual role of lysosomal processing. *Hum Mol Genet* 18, 4153-70 (2009).
12. Sooparb, S., Price, S. R., Shaoguang, J. & Franch, H. A. Suppression of chaperone-mediated autophagy in the renal cortex during acute diabetes mellitus. *Kidney Int* 65, 2135-44 (2004).
13. Venugopal, B. et al. Chaperone-mediated autophagy is defective in mucolipidosis type IV. *J Cell Physiol* 219, 344-353 (2009).
14. Cuervo, A. M. & Dice, J. F. Age-related decline in chaperone-mediated autophagy. *J Biol Chem* 275, 31505-31513 (2000).
15. Zhang, C. & Cuervo, A. M. Restoration of chaperone-mediated autophagy in aging liver improves cellular maintenance and hepatic function. *Nat Med* 14, 959-65 (2008).
16. Finn, P., Mesires, N., Vine, M. & Dice, J. F. Effects of small molecules on chaperone-mediated autophagy. *Autophagy* 1, 141-145 (2005).
17. Duong, V. & Rochette-Egly, C. The molecular physiology of nuclear retinoic acid receptors. From health to disease. *Biochim Biophys Acta* 1812, 1023-31 (2011).
18. Kon, M. et al. Chaperone-mediated autophagy is required for tumor growth. *Sci. Trans. Med.* 3, 109ra117 (2011).
19. Frolik, C. A., Roller, P. P., Roberts, A. B. & Sporn, M. B. In vitro and in vivo metabolism of all-trans- and 13-cis-retinoic acid in hamsters. Identification of 13-cis-4-oxoretinoic acid. *J Biol Chem* 255, 8057-62 (1980).
20. Rochette-Egly, C. & Germain, P. Dynamic and combinatorial control of gene expression by nuclear retinoic acid receptors (RARs). *Nucl Recept Signal* 7, e005 (2009).
21. de Lera, A. R., Bourguet, W., Altucci, L. & Gronemeyer, H. Design of selective nuclear receptor modulators: RAR and RXR as a case study. *Nat Rev Drug Discov* 6, 811-20 (2007).
22. Njar, V. C. et al. Retinoic acid metabolism blocking agents (RAMBAs) for treatment of cancer and dermatological diseases. *Bioorg Med Chem* 14, 4323-40 (2006).
23. Das, B. C. et al. Design and Synthesis of 3,5-Disubstituted 1,2,4-Oxadiazole Containing Retinoids from a Retinoic Acid Receptor Agonist. *Tetrahedron Lett* 52, 2433-2435 (2011).
24. Das, B. C., McCartin, K., Liu, T. C., Peterson, R. T. & Evans, T. A forward chemical screen in zebrafish identifies a retinoic acid derivative with receptor specificity. *PLoS One* 5, e10004 (2010).
25. Isakson, P., Bjoras, M., Boe, S. O. & Simonsen, A. Autophagy contributes to therapy-induced degradation of the PML/RARA oncoprotein. *Blood* 116, 2324-31 (2010).
26. Wang, Z. et al. Autophagy regulates myeloid cell differentiation by p62/SQSTM1-mediated degradation of PML-RARalpha oncoprotein. *Autophagy* 7, 401-11 (2011).
27. Trocoli, A. et al. ATRA-induced upregulation of Beclin 1 prolongs the life span of differentiated acute promyelocytic leukemia cells. *Autophagy* 7, 1108-14 (2011).
28. Rajawat, Y., Hilioti, Z. & Bossis, I. Retinoic acid induces autophagosome maturation through redistribution of the cation-independent mannose-6-phosphate receptor. *Antioxid Redox Signal* 14, 2165-77 (2011).
29. Tanida, I., Minematsu-Ikeguchi, N., Ueno, T. & Kominami, E. Lysosomal Turnover, but Not a Cellular Level, of Endogenous LC3 is a Marker for Autophagy. *Autophagy* 1, 84-91 (2005).
30. Koga, H., Martinez-Vicente, M., Verkhusha, V. V. & Cuervo, A. M. A photoconvertible fluorescent reporter to track chaperone-mediated autophagy. *Nat. Comm.* 2, 386 (2011).
31. le Maire, A. et al. A unique secondary-structure switch controls constitutive gene repression by retinoic acid receptor. *Nat Struct Mol Biol* 17, 801-7 (2010).
32. Das, B. C., Anguiano, J. & Mahalingam, S. M. Design and Synthesis of α-Aminonitrile Functionalized Novel Retinoids. *Tetrahedron Lett.* 50, 5670-5672 (2009).

33. Massey, A. C., Kaushik, S., Sovak, G., Kiffin, R. & Cuervo, A. M. Consequences of the selective blockage of chaperone-mediated autophagy. *Proc Nat Acad Sci USA* 103, 5905-5910 (2006).
34. Ahlemeyer, B. et al. Retinoic acid reduces apoptosis and oxidative stress by preservation of SOD protein level. *Free Radic Biol Med* 30, 1067-77 (2001).
35. Kiffin, R., Christian, C., Knecht, E. & Cuervo, A. Activation of chaperone-mediated autophagy during oxidative stress. *Mol Biol Cell* 15, 4829-4840 (2004).
36. Eskelinen, E. et al. Role of LAMP-2 in lysosome biogenesis and autophagy. *Mol Biol Cell.* 13, 3355-68 (2002).
37. Sardiello, M. et al. A gene network regulating lysosomal biogenesis and function. *Science* 325, 473-7 (2009).
38. Delacroix, L. et al. Cell-specific interaction of retinoic acid receptors with target genes in mouse embryonic fibroblasts and embryonic stem cells. *Mol Cell Biol* 30, 231-44 (2010).
39. Kaushik, S. & Cuervo, A. M. Methods to monitor chaperone-mediated autophagy. *Methods Enzymol* 452, 297-324 (2009).
40. Klionsky, D. J. et al. Guidelines for the use and interpretation of assays for monitoring autophagy. *Autophagy* 8, 445-544 (2012).
41. Cuervo, A. M., Dice, J. F. & Knecht, E. A population of rat liver lysosomes responsible for the selective uptake and degradation of cytosolic proteins. *J Biol Chem* 272, 5606-15 (1997).
42. Shridhar, D. R., Reddy, C. V., Sastry, O. P., Bansal, O. P. & Rao, P. P. A convenient one-step synthesis of 3-Aryl-2H-1,4-benzoxazines. *Synthesis* 1981, 912-913 (1981).
43. Friesner, R. A. et al. Extra precision glide: docking and scoring incorporating a model of hydrophobic enclosure for protein-ligand complexes. *J Med Chem* 49, 6177-96 (2006).
44. Halgren, T. A. et al. Glide: a new approach for rapid, accurate docking and scoring. 2. Enrichment factors in database screening. *J Med Chem* 47, 1750-9 (2004).
45. Friesner, R. A. et al. Glide: a new approach for rapid, accurate docking and scoring. 1. Method and assessment of docking accuracy. *J Med Chem* 47, 1739-49 (2004).
46. Shivakumar, D. et al. Prediction of Absolute Solvation Free Energies using Molecular Dynamics Free Energy Perturbation and the OPLS Force Field. *J. Chem. Theory Comput.* 6, 1509-1519 (2010).
47. Guo, Z. et al. Probing the alpha-helical structural stability of stapled p53 peptides: molecular dynamics simulations and analysis. *Chem Biol Drug Des* 75, 348-59 (2010).
48. Bowers, K. et al. Scalable Algorithms for Molecular Dynamics Simulations on Commodity Clusters. in *ACM/IEEE Conference on Supercomputing* (SC06) Vol. November 11-17 (Tampa, Fla., 2006).
49. Auteri, J. S., Okada, A., Bochaki, V. & Dice, J. F. Regulation of intracellular protein degradation in IMR-90 human diploid fibroblasts. *J Cell Physiol* 115, 159-166 (1983).
50. Das, B. C., Madhukumar, A. V., Anguiano, J. & Mani, S. Design, synthesis and biological evaluation of 2H-benzo[b][1,4]oxazine derivatives as hypoxia targeted compounds for cancer therapeutics. *Bioorg Med Chem Lett* 19, 4204-6 (2009).

---

What is claimed is:

1. A method of selectively activating chaperone-mediated autophagy (CMA) in a subject in need thereof comprising administering to the subject a compound of formula (II), or a combination of any compounds thereof, in an amount effective to activate CMA, wherein the subject has Parkinson's Disease, Huntington's Disease, frontotemporal dementia, retinal degeneration, multiple sclerosis, diabetes, a lysosomal storage disorder, a retinal disease, a cardiovascular disease, myocardial infarction, cardiac hypertrophy or a cardiomyopathy, and wherein formula (II) is

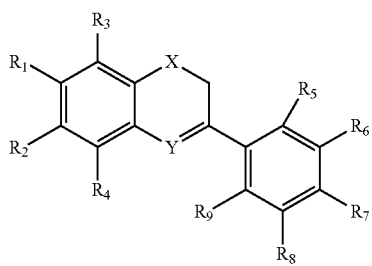

wherein
R1, R2, R3, R4, R5, R6, R8 and R9 of formula (II) are independently H, hydroxyl, halogen, SH, $NO_2$, $CF_3$, COOH, COOR10, CHO, CN, $NH_2$, NHR10, $NHCONH_2$, NHCONHR10, NHCOR10, $NHSO_2R10$, OCR10, COR10, $CH_2R10$, CON(R10,R11), CH=N—OR10, CH=NR10, OR10, SR10, SOR10, $SO_2R10$, COOR10, $CH_2N$(R10,R11), N(R10,R11), or optionally substituted lower alkyl, alkenyl, alkynyl, cycloalkyl, heterocycloalky, aryl, heteroaryl, aralkyl, or heteroaralkyl; wherein the optional substituent is one or more of F, Cl, Br, I, OH, SH, $NO_2$, COOH, COOR10, R10, CHO, CN, $NH_2$, NHR10, $NHCONH_2$, NHCONHR10, NHCOR10, $NHSO_2R10$, HOCR10, COR10, $CH_2R10$, CON (R10, R11), CH=N—OR10, CH=NR10, OR10, SR10, SOR10, $SO_2R10$, COOR10, $CH_2N$(R10, R11), N(R10, R11);
R7 of formula (II) is H, hydroxyl, halogen, $CF_3$, CN, $OCF_3$, COOH, $COOCH_3$, COOR10, $COO(CH_2)_2Si(CH_3)_3$, $COOR10Si(CH_3)_3$, $NHCOCH_3$, C≡C—$CH_2OH$, C≡C—R10-OH or optionally substituted alkyl, aryl, heteroaryl, aralkyl, heteroaralkyl, cyclic or heterocyclic; wherein the optional substituent is one or more of F, Cl, Br, I, OH, SH, $NO_2$, $CH_3$, R10, COOH, COOR10, CHO, CN, $NH_2$, NHR10, $NHCONH_2$, NHCONHR10, NHCOR10, $NHSO_2R10$, HOCR10, COR10, $CH_2R10$, CON(R10, R11), CH=N—OR10, CH=NR10, OR10, SR10, SOR10, $SO_2R10$, COOR10, $CH_2N$(R10, R11), N(R10, R11);
R10 and R11 are independently H or C1-C6 alkyl; and
X is O; and Y is N;
or a pharmaceutically acceptable salt thereof.

2. The method of claim 1, wherein the subject has reduced CMA compared to a normal subject prior to administering the compound.

3. The method of claim 1, wherein the compound does not affect macroautophagy.

4. The method of claim 1, wherein the compound has the structure

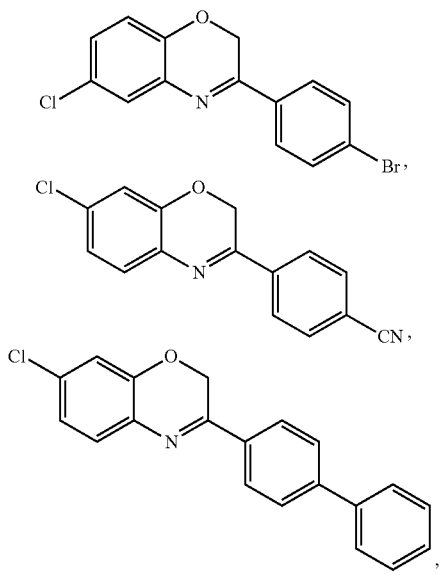

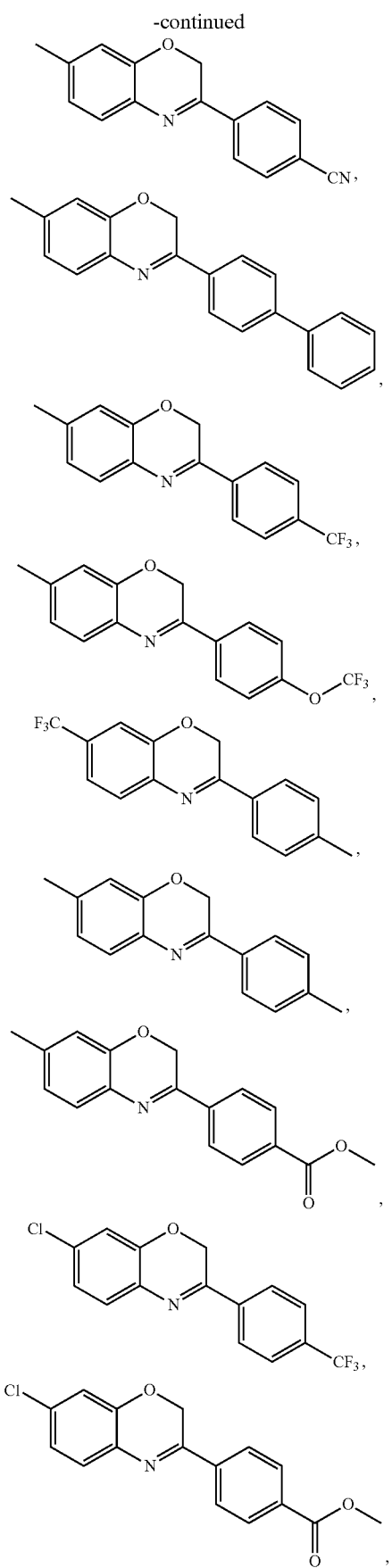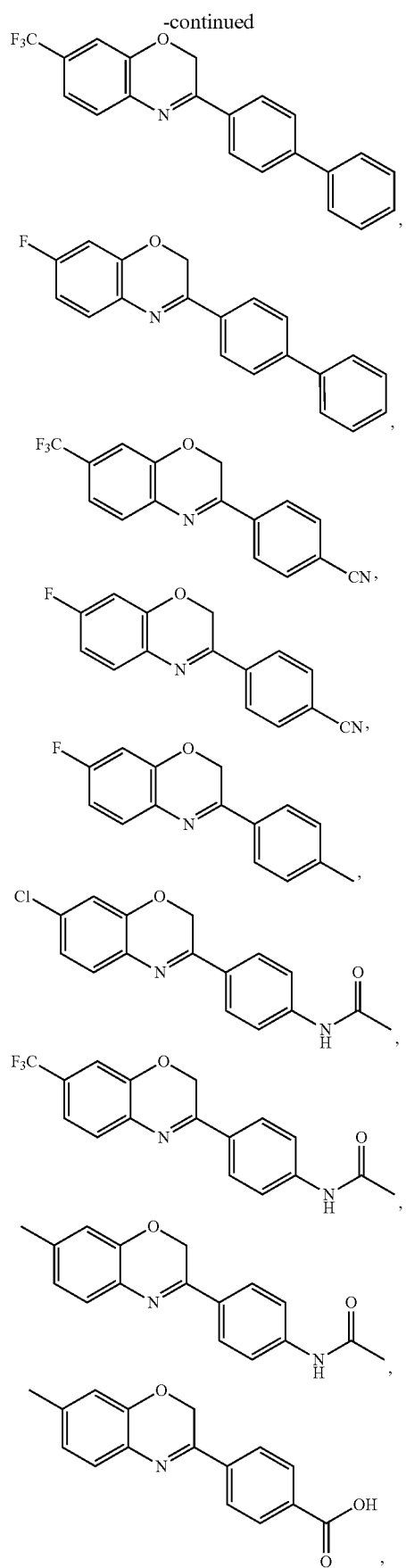

-continued
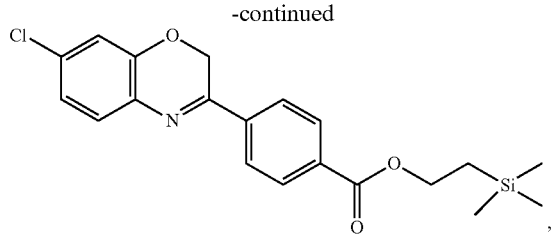
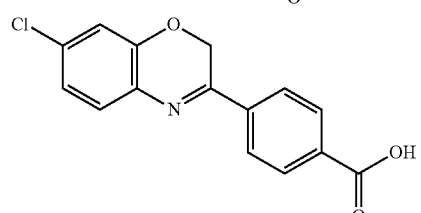
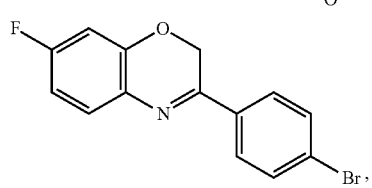
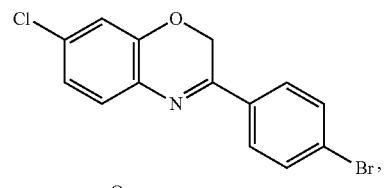
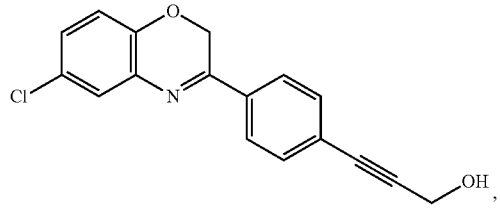
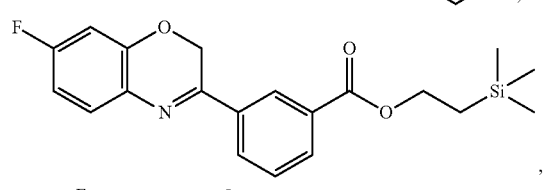
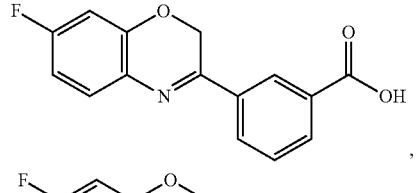
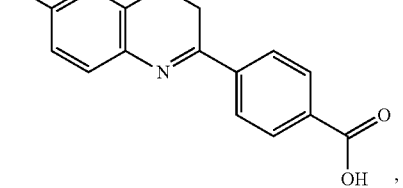
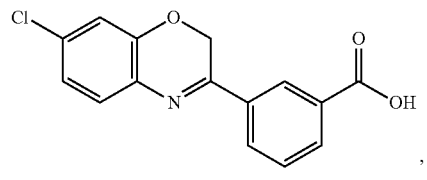
-continued
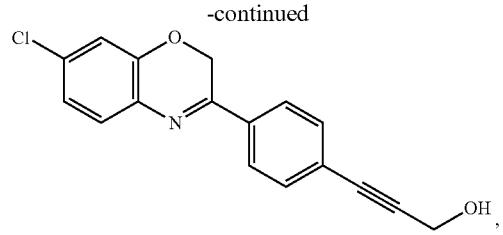
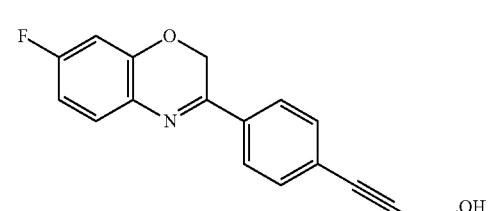
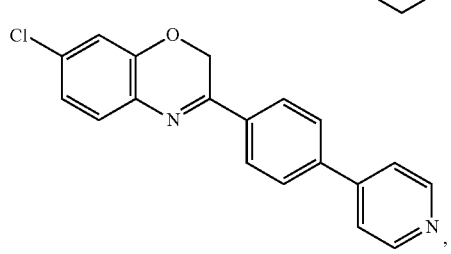
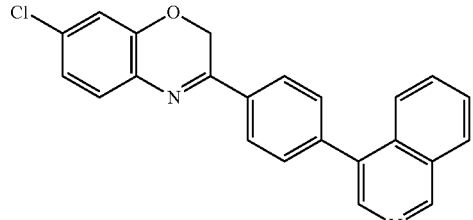
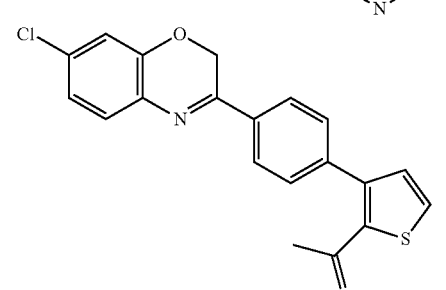
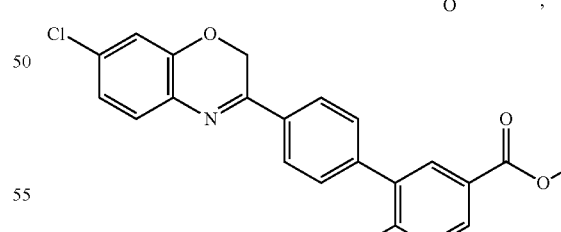, or
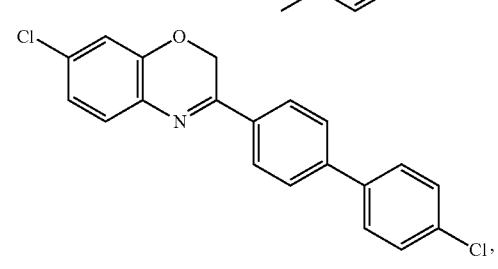

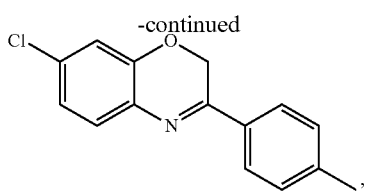

or a combination thereof, or a pharmaceutically acceptable salt thereof.

5. The method of claim 1, wherein any one or more halogen is Br, Cl, F or I independently of any other halogen.

6. The method of claim 1, wherein the optionally substituted aryl or heteroaryl is

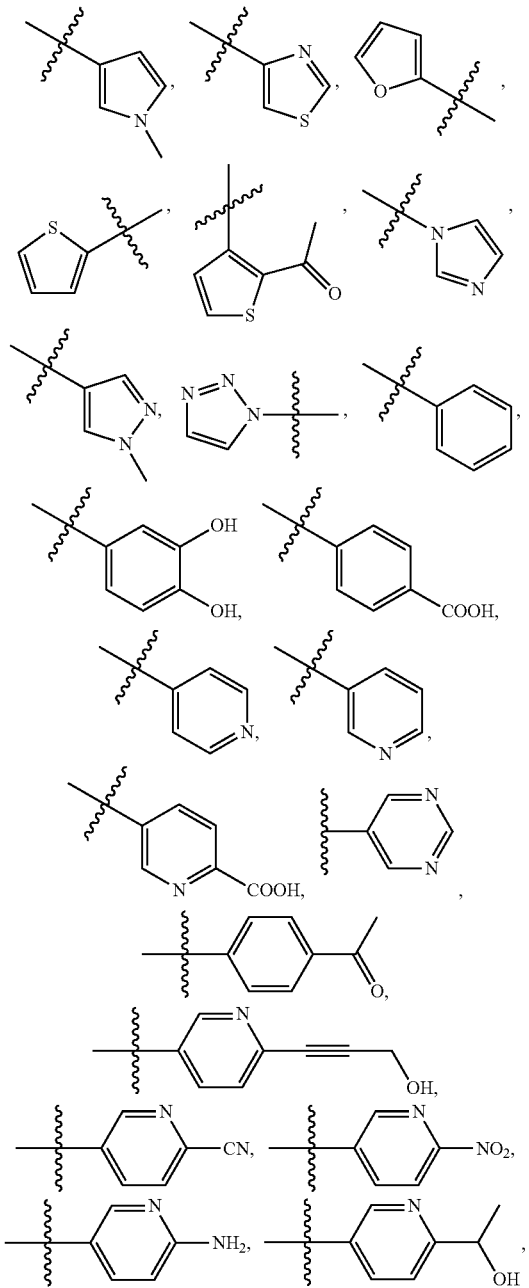

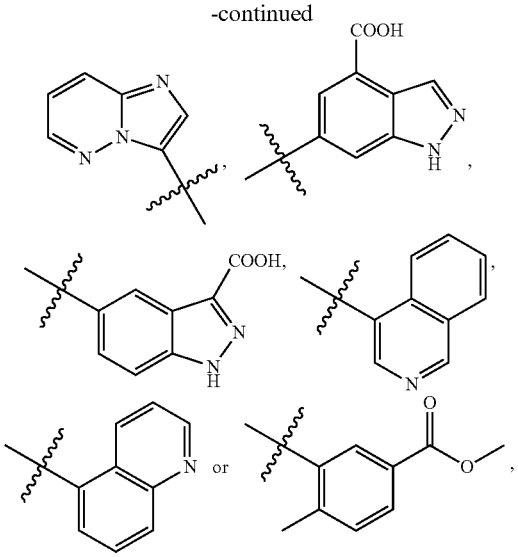

where the wavy line

indicates the point of attachment of the optionally substituted aryl or heteroaryl to the main structure.

7. A method of protecting cells from oxidative stress, proteotoxicity and/or lipotoxicity in a subject in need thereof comprising administering to the subject a compound of formula (II), or a combination of any compounds thereof, in an amount effective to protect cells from oxidative stress, proteotoxicity and/or lipotoxicity, wherein the subject has Parkinson's Disease, Huntington's Disease, frontotemporal dementia, retinal degeneration, multiple sclerosis, diabetes, a lysosomal storage disorder, a retinal disease, a cardiovascular disease, myocardial infarction, cardiac hypertrophy or a cardiomyopathy, and wherein formula (II) is

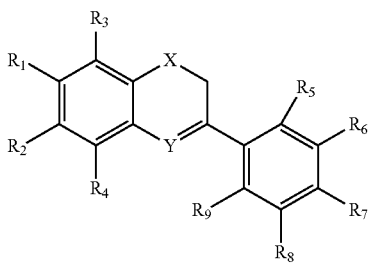

wherein

R1, R2, R3, R4, R5, R6, R8 and R9 of formula (II) are independently H, hydroxyl, halogen, SH, $NO_2$, $CF_3$, COOH, COOR10, CHO, CN, $NH_2$, NHR10, $NHCONH_2$, NHCONHR10, NHCOR10, $NHSO_2R10$, OCR10, COR10, $CH_2R10$, CON(R10,R11), CH=N—OR10, CH=NR10, OR10, SR10, SOR10, $SO_2R10$, COOR10, $CH_2N(R10,R11)$, N(R10,R11), or optionally substituted lower alkyl, alkenyl, alkynyl, cycloalkyl, heterocycloalky, aryl, heteroaryl, aralkyl, or heteroaralkyl; wherein the optional substituent is one or more of F, Cl, Br, I, OH, SH, NO$_2$, COOH, COOR10, R10, CHO, CN, NH$_2$, NHR10, NHCONH$_2$, NHCONHR10, NHCOR10, NHSO$_2$R10, HOCR10, COR10, CH$_2$R10, CON (R10, R11), CH=N—OR10, CH=NR10, OR10, SR10, SOR10, SO$_2$R10, COOR10, CH$_2$N(R10, R11), N(R10, R11);

R7 of formula (II) is H, hydroxyl, halogen, CF$_3$, CN, OCF$_3$, COOH, COOCH$_3$, COOR10, COO(CH$_2$)$_2$Si(CH$_3$)$_3$, COOR10Si(CH$_3$)$_3$, NHCOCH$_3$, C≡C—CH$_2$OH, C≡C—R10-OH or optionally substituted alkyl, aryl, heteroaryl, aralkyl, heteroaralkyl, cyclic or heterocyclic; wherein the optional substituent is one or more of F, Cl, Br, I, OH, SH, NO$_2$, CH$_3$, R10, COOH, COOR10, CHO, CN, NH$_2$, NHR10, NHCONH$_2$, NHCONHR10, NHCOR10, NHSO$_2$R10, HOCR10, COR10, CH$_2$R10, CON(R10, R11), CH=N—OR10, CH=NR10, OR10, SR10, SOR10, SO$_2$R10, COOR10, CH$_2$N(R10, R11), N(R10, R11);

R10 and R11 are independently H or C1-C6 alkyl; and X is O; and Y is N;

or a pharmaceutically acceptable salt thereof.

8. The method of claim 7, wherein the cells being protected comprise cardiac cells, liver cells, neurons, myocytes, fibroblasts and/or immune cells.

9. The method of claim 7, wherein any one or more halogen is Br, Cl, F or I independently of any other halogen.

10. The method of claim 7, wherein any one or more alkyl is C1-C3 alkyl independently of any other alkyl.

11. The method of claim 7, wherein any one or more aralkyl contains C1-C3 alkyl independently of any other aralkyl.

12. The method of claim 7, wherein the compound selectively activates chaperone-mediated autophagy (CMA).

13. The method of claim 7, wherein the compound does not affect macroautophagy.

14. The method of claim 7, wherein the compound antagonizes activity of retinoic acid receptor alpha (RARα).

15. The method of claim 7, wherein the optionally substituted aryl or heteroaryl is

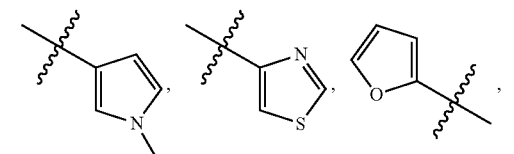

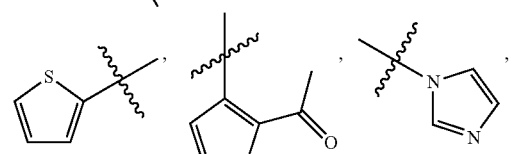

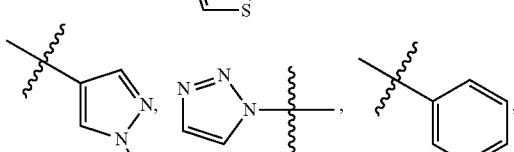

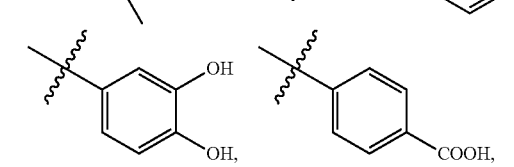

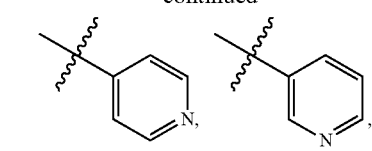

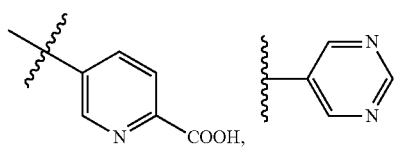

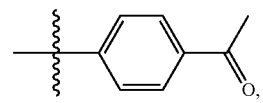

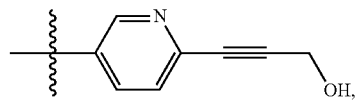

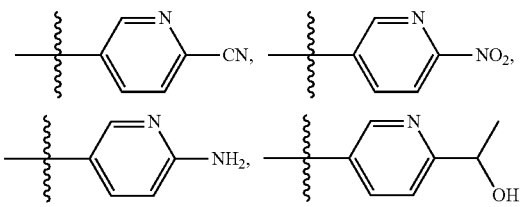

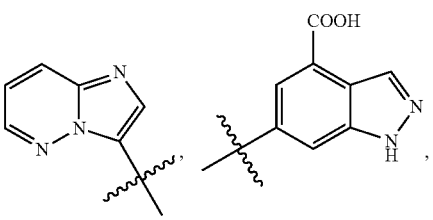

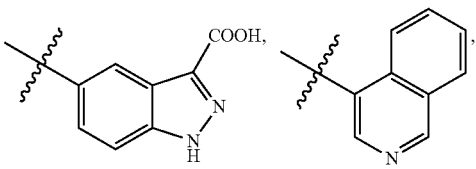

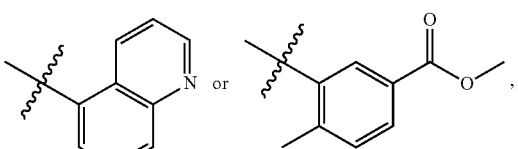

where the wavy line

indicates the point of attachment of the optionally substituted aryl or heteroaryl to the main structure.

16. The method of claim 7, wherein the compound has the structure
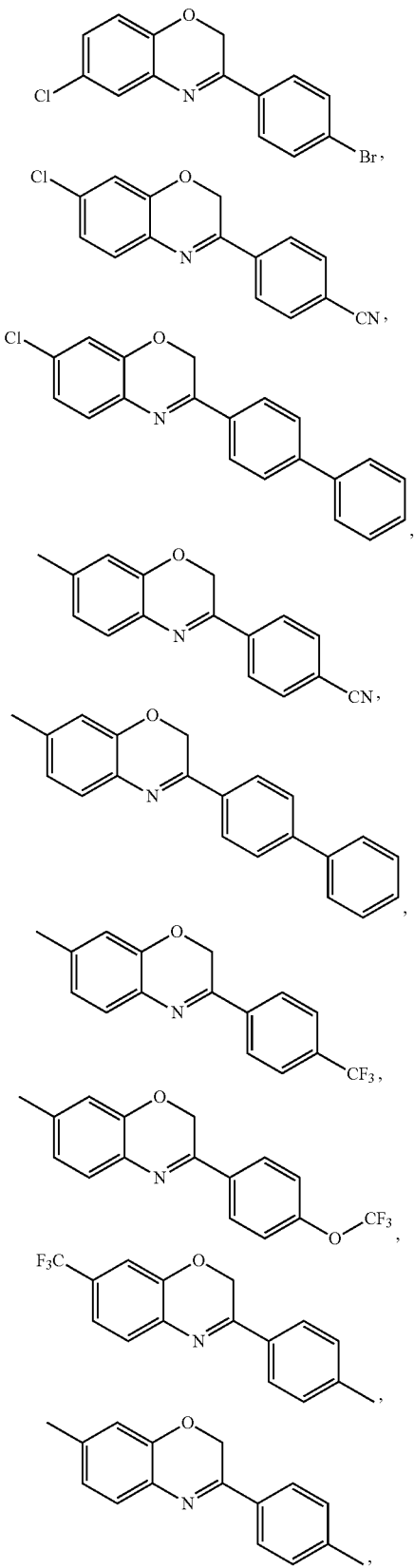
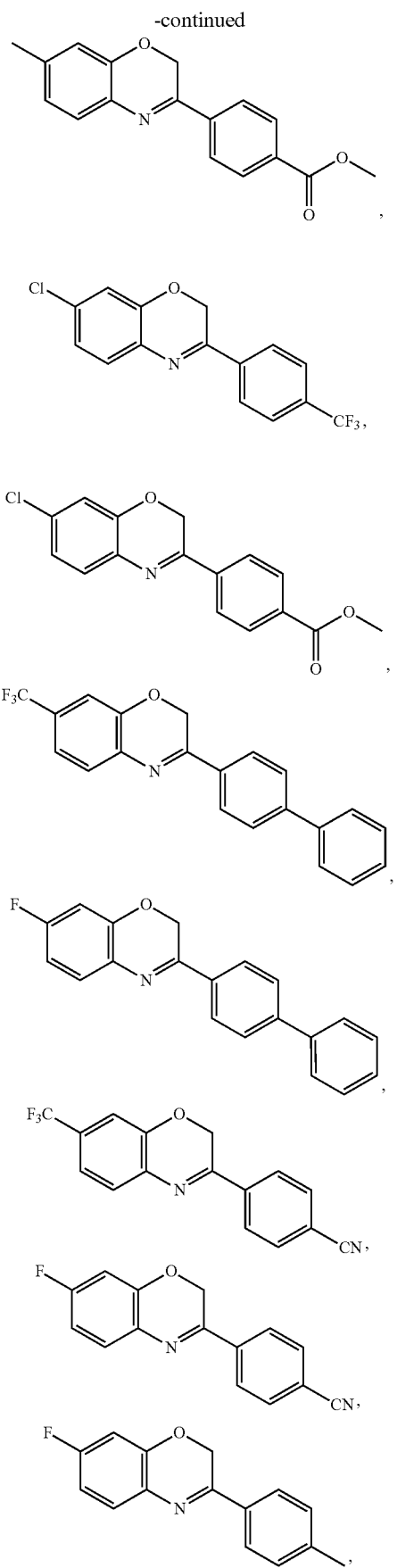

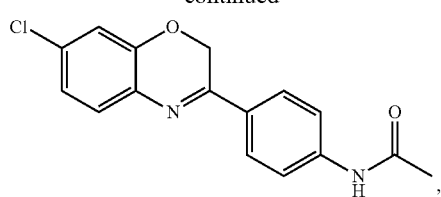
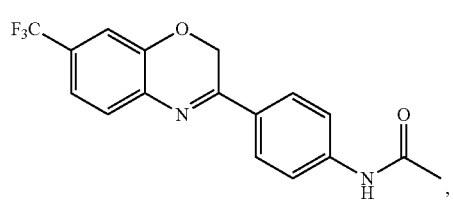
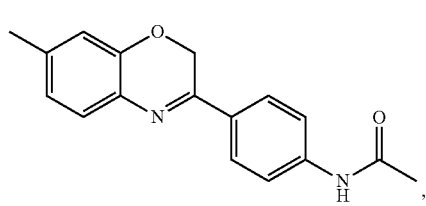
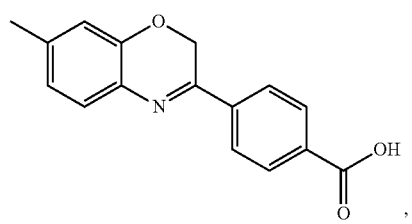
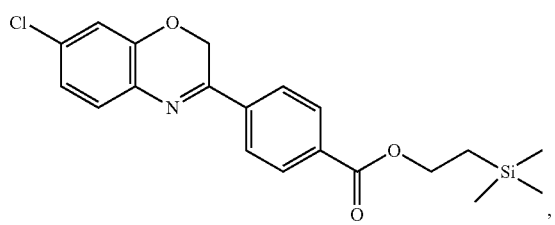
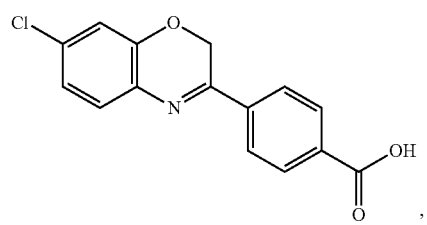
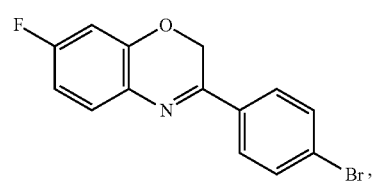
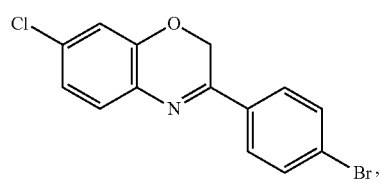
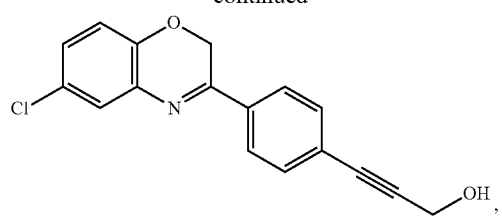
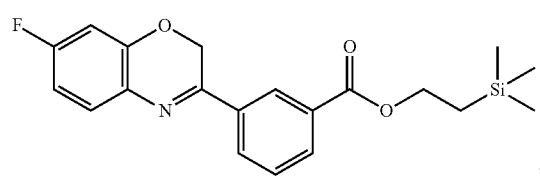
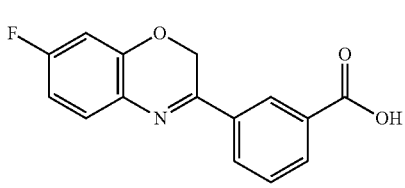
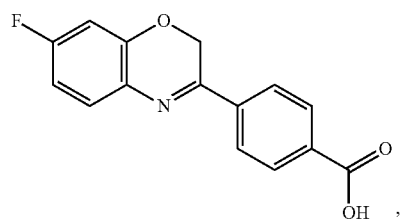
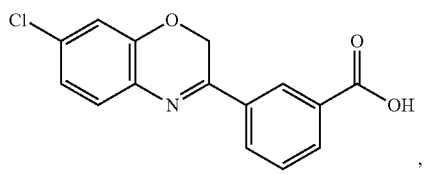
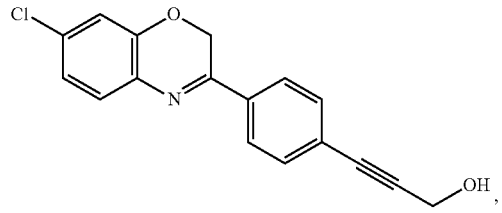
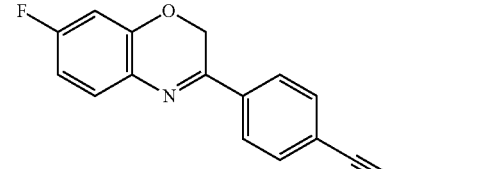
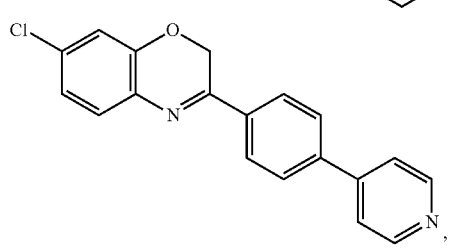

-continued

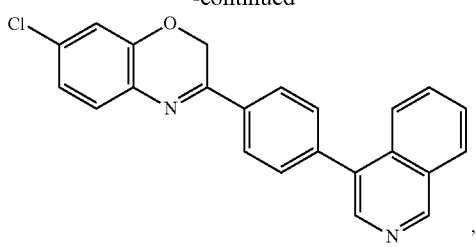

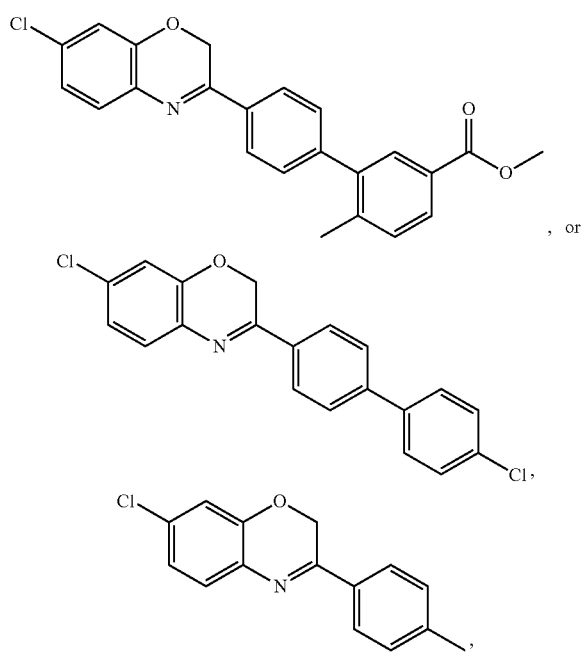

or a combination thereof, or a pharmaceutically acceptable salt thereof.

17. A method of antagonizing activity of retinoic acid receptor alpha (RARα) in a subject in need thereof comprising administering to the subject a compound of formula (II), or a combination of any compounds thereof, in an amount effective to act as a RARα antagonist, wherein the subject has Parkinson's Disease, Huntington's Disease, frontotemporal dementia, retinal degeneration, multiple sclerosis, diabetes, a lysosomal storage disorder, a retinal disease, a cardiovascular disease, myocardial infarction, cardiac hypertrophy or a cardiomyopathy, and wherein formula (II) is

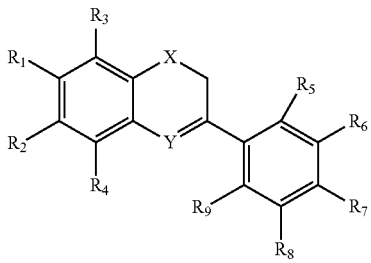

wherein

R1, R2, R3, R4, R5, R6, R8 and R9 of formula (II) are independently H, hydroxyl, halogen, SH, $NO_2$, $CF_3$, COOH, COOR10, CHO, CN, $NH_2$, NHR10, $NHCONH_2$, NHCONHR10, NHCOR10, $NHSO_2R10$, OCR10, COR10, $CH_2R10$, CON(R10,R11), CH=N—OR10, CH=NR10, OR10, SR10, SOR10, $SO_2R10$, COOR10, $CH_2N$(R10,R11), N(R10,R11), or optionally substituted lower alkyl, alkenyl, alkynyl, cycloalkyl, heterocycloalky, aryl, heteroaryl, aralkyl, or heteroaralkyl; wherein the optional substituent is one or more of F, Cl, Br, I, OH, SH, $NO_2$, COOH, COOR10, R10, CHO, CN, $NH_2$, NHR10, $NHCONH_2$, NHCONHR10, NHCOR10, $NHSO_2R10$, HOCR10, COR10, $CH_2R10$, CON(R10, R11), CH=N—OR10, CH=NR10, OR10, SR10, SOR10, $SO_2R10$, COOR10, $CH_2N$(R10, R11), N(R10, R11);

R7 of formula (II) is H, hydroxyl, halogen, $CF_3$, CN, $OCF_3$, COOH, $COOCH_3$, COOR10, $COO(CH_2)_2Si(CH_3)_3$, $COOR10Si(CH_3)_3$, $NHCOCH_3$, C≡C—$CH_2OH$, C≡C—R10-OH or optionally substituted alkyl, aryl, heteroaryl, aralkyl, heteroaralkyl, cyclic or heterocyclic; wherein the optional substituent is one or more of F, Cl, Br, I, OH, SH, $NO_2$, $CH_3$, R10, COOH, COOR10, CHO, CN, $NH_2$, NHR10, $NHCONH_2$, NHCONHR10, NHCOR10, $NHSO_2R10$, HOCR10, COR10, $CH_2R10$, CON(R10, R11), CH=N—OR10, CH=NR10, OR10, SR10, SOR10, $SO_2R10$, COOR10, $CH_2N$(R10, R11), N(R10, R11);

R10 and R11 are independently H or C1-C6 alkyl; and X is O; and Y is N;

or a pharmaceutically acceptable salt thereof.

18. The method of claim 17, wherein the compound has the structure

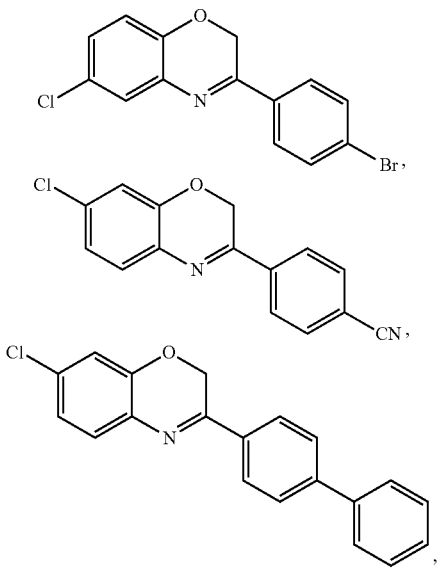

-continued

-continued

-continued

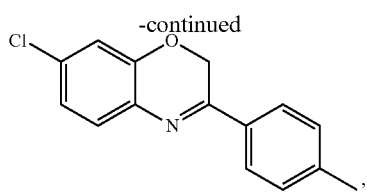

or a combination thereof, or a pharmaceutically acceptable salt thereof.

19. The method of claim 17, wherein any one or more halogen is Br, Cl, F or I independently of any other halogen.

20. The method of claim 17, wherein the optionally substituted aryl or heteroaryl is

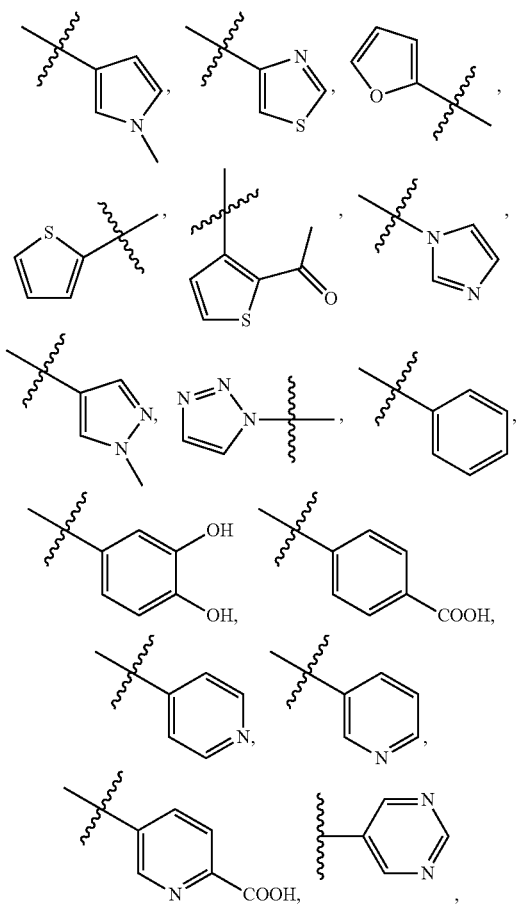

-continued

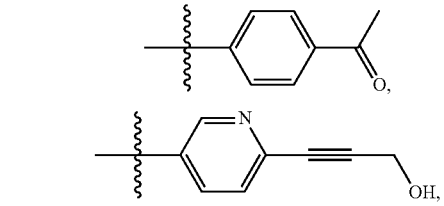

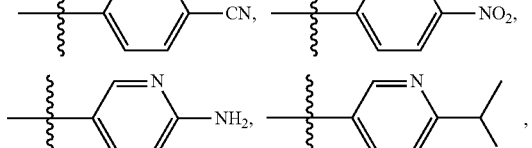

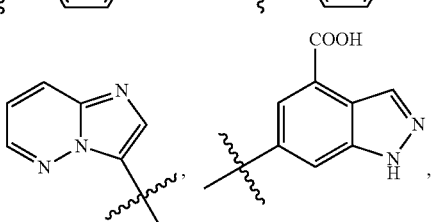

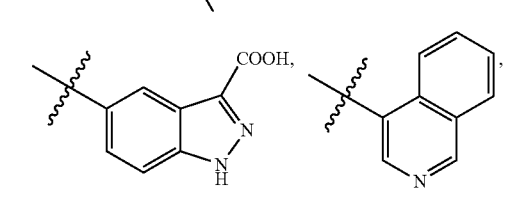

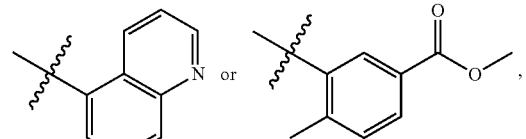

where the wavy line

indicated the point of attachment of the optionally substituted aryl or heteroaryl to the main structure.

* * * * *

SEQUENCE LISTING

<160> NUMBER OF SEQ ID NOS: 5

<210> SEQ ID NO 1
<211> LENGTH: 24
<212> TYPE: PRT
<213> ORGANISM: Homo sapiens

<400> SEQUENCE: 1

Asp Ile Asp Leu Trp Asp Lys Phe Ser Glu Leu Ser Thr Lys Cys Ile
1               5                   10                  15

Ile Lys Thr Val Glu Phe Ala Lys
            20

<210> SEQ ID NO 2
<211> LENGTH: 21
<212> TYPE: PRT
<213> ORGANISM: Homo sapiens

<400> SEQUENCE: 2

Asp Leu Arg Ser Ile Ser Ala Lys Gly Ala Glu Arg Val Ile Thr Leu
1               5                   10                  15

Lys Met Glu Ile Pro
            20

<210> SEQ ID NO 3
<211> LENGTH: 13
<212> TYPE: PRT
<213> ORGANISM: Homo sapiens

<400> SEQUENCE: 3

```
Gly Ser Met Pro Pro Leu Ile Gln Glu Met Leu Glu Asn
1               5                   10
```

```
<210> SEQ ID NO 4
<211> LENGTH: 19
<212> TYPE: DNA
<213> ORGANISM: Homo sapiens

<400> SEQUENCE: 4
gaaagtctac gtccggaaa                                              19

<210> SEQ ID NO 5
<211> LENGTH: 19
<212> TYPE: DNA
<213> ORGANISM: Homo sapiens

<400> SEQUENCE: 5
gcagcagttc cgaagagat                                              19
```